US009527832B2

(12) United States Patent
Konetzki et al.

(10) Patent No.: US 9,527,832 B2
(45) Date of Patent: Dec. 27, 2016

(54) SUBSTITUTED CONDENSED PYRIMIDINE COMPOUNDS

(71) Applicant: GRÜNENTHAL GMBH, Aachen (DE)

(72) Inventors: Ingo Konetzki, Aachen (DE); Florian Jakob, Aachen (DE); Tobias Craan, Aachen (DE); Christian Hesslinger, Zoznegg (DE); Paul Ratcliffe, Aachen (DE); Antonio Nardi, Herzogenrath (DE)

(73) Assignee: GRÜNENTHAL GMBH, Aachen (DE)

(*) Notice: Subject to any disclaimer, the term of this patent is extended or adjusted under 35 U.S.C. 154(b) by 0 days.

(21) Appl. No.: 14/883,986

(22) Filed: Oct. 15, 2015

(65) Prior Publication Data

US 2016/0031857 A1 Feb. 4, 2016

Related U.S. Application Data

(63) Continuation of application No. PCT/EP2014/001013, filed on Apr. 15, 2014.

(30) Foreign Application Priority Data

Apr. 16, 2013 (EP) ..................................... 13001993

(51) Int. Cl.
*C07D 413/04* (2006.01)
*C07D 403/04* (2006.01)
*C07D 495/04* (2006.01)

(52) U.S. Cl.
CPC ........... *C07D 403/04* (2013.01); *C07D 413/04* (2013.01); *C07D 495/04* (2013.01)

(58) Field of Classification Search
USPC ................. 514/210.08, 234.5, 252.16, 260.1
See application file for complete search history.

(56) References Cited

U.S. PATENT DOCUMENTS

| | | | |
|---|---|---|---|
| 2006/0293343 A1 | 12/2006 | Naganuma et al. | |
| 2008/0070896 A1 | 3/2008 | Yonetoku et al. | |
| 2011/0046096 A1 | 2/2011 | Pouzet et al. | |
| 2015/0344496 A1* | 12/2015 | Konetzki .............. | C07D 409/04 514/260.1 |

FOREIGN PATENT DOCUMENTS

| | | |
|---|---|---|
| EP | 0 180 371 A2 | 5/1986 |
| WO | 95 01338 A1 | 1/1995 |
| WO | 2005014558 A1 | 2/2005 |

OTHER PUBLICATIONS

Schudt et al., "PDE Isoenzymes as Targets for Anti-Asthma Drugs"; European Respiratory Journal, 1995, vol. 8, pp. 1179-1183.
Mori, et al., "The human area postrema and other nuclei related to the emetic reflex express cAMP phosphodiesterases 4B and 4D"; Journal of Chemical Neuroanatomy, vol. 40, 2010, pp. 36-42.
Press, et al., "2 PDE4 Inhibitors—A review of the current field"; Progress in Medicinal Chemistry, vol. 47, 2009, pp. 37-74.
Robichaud, et al., "Deletion of phosphodiesterase 4D in mice shortens alpha2-adrenoceptor-mediated anesthesia, a behavioral correlate of emesis"; Journal of Clinical Investigation, vol. 110, No. 7, 2002, pp. 1045-1052.
Lee, et al., "Dynamic Regulation of Cystic Fibrosis Transmembrane Conductance Regulator by Competitive Interactions of Molecular Adaptors"; the Journal of Biological Chemistry, vol. 282, No. 14, Apr. 6, 2007, pp. 10414-10422.
Giembycz, "4D or not 4D—the emetogenic basis of PDE4 inhibitors uncovered?"; TRENDS in Pharmacological Sciences, vol. 23, No. 12, Dec. 2002, pp. 548.
Naganuma, et al., "Discovery of selective PDE4B inhibitors"; Bioorganic & Medicinal Chemistry Letters 19, 2009, pp. 3174-3176.
Saldou, et al.; "Comparison of Recombinant Human PDE4 Isoforms: Interaction with Substrate and Inhibitors"; Cell. Signal. vol. 10, No. 6, 1998, pp. 427-440.
Chakraborti et al., "3D-QSAR Studies on Thieno[3,2-d]pyrimidines as Phosphodiesterase IV Inhibitors"; Bioorganic & Medicinal Chemistry Letters 13, 2003, pp. 1403-1408.
"Remington's Pharmaceutical Sciences", Ed. A.R. Gennaro, 17th edition, Mack Publishing Company, Easton PA (1985), chapters 76.
"Remington's Pharmaceutical Sciences", Ed. A.R. Gennaro, 17th edition, Mack Publishing Company, Easton PA (1985), chapters 77.
"Remington's Pharmaceutical Sciences", Ed. A.R. Gennaro, 17th edition, Mack Publishing Company, Easton PA (1985), chapters 78.
"Remington's Pharmaceutical Sciences", Ed. A.R. Gennaro, 17th edition, Mack Publishing Company, Easton PA (1985), chapters 79.
"Remington's Pharmaceutical Sciences", Ed. A.R. Gennaro, 17th edition, Mack Publishing Company, Easton PA (1985), chapters 80.
"Remington's Pharmaceutical Sciences", Ed. A.R. Gennaro, 17th edition, Mack Publishing Company, Easton PA (1985), chapters 81.

(Continued)

*Primary Examiner* — Sudhakar Katakam
*Assistant Examiner* — Pancham Bakshi
(74) *Attorney, Agent, or Firm* — Norris McLaughlin & Marcus, P.A.

(57) ABSTRACT

The invention relates to novel substituted condensed pyrimidine compounds of general formula (I)

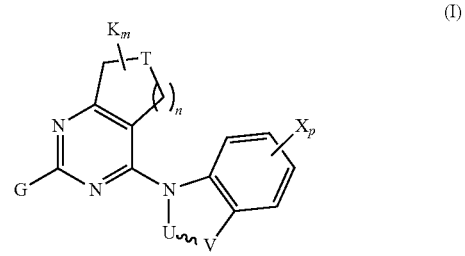

in which the chemical groupings, substituents and indices are as defined in the description, and to their use as medicaments, in particular as medicaments for the treatment of conditions and diseases that can be treated by inhibition of the PDE4 enzyme.

10 Claims, No Drawings

(56) References Cited

OTHER PUBLICATIONS

"Remington's Pharmaceutical Sciences", Ed. A.R. Gennaro, 17th edition, Mack Publishing Company, Easton PA (1985), chapters 82.
"Remington's Pharmaceutical Sciences", Ed. A.R. Gennaro, 17th edition, Mack Publishing Company, Easton PA (1985), chapters 83.
"Remington's Pharmaceutical Sciences", Ed. A.R. Gennaro, 17th edition, Mack Publishing Company, Easton PA (1985), chapters 84.
"Remington's Pharmaceutical Sciences", Ed. A.R. Gennaro, 17th edition, Mack Publishing Company, Easton PA (1985), chapters 85.
"Remington's Pharmaceutical Sciences", Ed. A.R. Gennaro, 17th edition, Mack Publishing Company, Easton PA (1985), chapters 86.
"Remington's Pharmaceutical Sciences", Ed. A.R. Gennaro, 17th edition, Mack Publishing Company, Easton PA (1985), chapters 87.
"Remington's Pharmaceutical Sciences", Ed. A.R. Gennaro, 17th edition, Mack Publishing Company, Easton PA (1985), chapters 88.
"Remington's Pharmaceutical Sciences", Ed. A.R. Gennaro, 17th edition, Mack Publishing Company, Easton PA (1985), chapters 89.
"Remington's Pharmaceutical Sciences", Ed. A.R. Gennaro, 17th edition, Mack Publishing Company, Easton PA (1985), chapters 90.
"Remington's Pharmaceutical Sciences", Ed. A.R. Gennaro, 17th edition, Mack Publishing Company, Easton PA (1985), chapters 91.
"Remington's Pharmaceutical Sciences", Ed. A.R. Gennaro, 17th edition, Mack Publishing Company, Easton PA (1985), chapters 92.
"Remington's Pharmaceutical Sciences", Ed. A.R. Gennaro, 17th edition, Mack Publishing Company, Easton PA (1985), chapters 93.

* cited by examiner

SUBSTITUTED CONDENSED PYRIMIDINE COMPOUNDS

This application is a continuation of International Patent Application No. PCT/EP2014/001013, filed Apr. 15, 2014, which claims foreign priority benefit under 35 U.S.C. §119 of European Patent Application No. 13001993.8 filed Apr. 16, 2013, the disclosures of which are incorporated herein by reference.

The present invention relates to novel substituted, condensed pyrimidine compounds, and to their use as pharmaceuticals (medicaments).

Pharmaceutically active substituted pyrimidine compounds are known (cf. US 2008/070896 A, (which is also published as EP180371 A, or WO2005/014558).

It is also known that certain pyrimidine compounds are suitable for inhibiting specific phosphodiesterases (abbreviated as PDEs). Phosphodiesterases, or more accurately 3',5'-cyclonucleotide phosphodiesterases, are enzymes that catalyse the hydrolysis of the second messengers cAMP (cyclic adenosine monophosphate) and cGMP (cyclic guanosine monophosphate) to 5'-AMP (5'-adenosine monophosphate) and 5'-GMP (5'-guanosine monophosphate). Inhibition of phosphodiesterases thus represents a mechanism for modulating cellular processes and can be used to alleviate or cure disease conditions.

WO 95/01338 A1, for example, describes how suitable PDE inhibitors can be used to treat inflammatory respiratory diseases, dermatoses, and other proliferative, inflammatory and allergic skin diseases. WO 95/01338 A1 proposes, moreover, that such PDE inhibitors can find application in the treatment of diseases that are based on an excess release of TNF and leukotrienes, for example diseases from the arthritis spectrum (rheumatoid arthritis, rheumatoid spondylitis, osteoarthritis and other arthritic conditions). The international publication proposes, furthermore, the use of suitable PDE inhibitors as medicaments for diseases of the immune system (e.g. AIDS), symptoms of shock, as well as generalised inflammations in the gastrointestinal system (e.g. Crohn's disease and ulcerative colitis), diseases based on allergic and/or chronic, immunological adverse reactions in the upper respiratory tract (lateral pharyngeal space, nose) and adjacent regions (sinuses, eyes), such as for example allergic rhinitis/sinusitis, chronic rhinitis/sinusitis, allergic conjunctivitis and nasal polyps, but also diseases of the heart that can be treated by PDE inhibitors, such as for example heart failure, or diseases that can be treated because of the tissue-relaxing effect of PDE inhibitors, such as for example renal and ureteric colic in conjunction with kidney stones.

Phosphodiesterases are a group of enzymes encompassing 11 gene families (PDE1-11), which differ inter alia through their affinity to cAMP and cGMP.

The inhibition of the individual gene families with suitable substances is the subject of wide-ranging research. A known PDE5 inhibitor is sildenafil, which is commercially available under the trade name Viagra™ and which is used primarily for the treatment of erectile dysfunction.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is roflumilast for example (known under the trade name Daxas®), which was approved as a medicament for the treatment of COPD (chronic obstructive pulmonary disease). In addition to the desired anti-inflammatory effect of roflumilast, however, side-effects such as for example nausea, diarrhoea and headaches are observed, which limit the dose in humans.

Undesired side-effects in humans were observed with other PDE4 inhibitors too, so the therapeutic range (therapeutic window) of such medicaments is relatively narrow. The provision of PDE4 inhibitors having side-effects and a better therapeutic window would therefore be desirable.

Phosphodiesterase 4 (PDE4) is cAMP-specific and encompasses 4 different subtypes (PDE4A, PDE4B, PDE4C and PDE4D). As described below, efforts are being made to find subtype-selective PDE4 inhibitors, above all PDE4B-selective inhibitors, that have less severe or no side-effects, such that the therapeutic range of these compounds is increased significantly.

The inhibition of PDE4D is associated with the occurrence of undesired side-effects, such as for example diarrhoea, vomiting and nausea (see in this regard Mori, F. et al. (2010). The human area postrema and other nuclei related to the emetic reflex express cAMP phosphodiesterases 4B and 4D. *Journal of Chemical Neuroanatomy* 40, 36-42; Press, N.J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

In an article entitled "Discovery of selective PDE4B inhibitors" published in Bioorganic & Medicinal Chemistry Letters 19 (2009) p. 3174-3176, Kenji et al. disclose thirty-five pyrimidine compounds that exhibit PDE4B selectivity. Some of the compounds listed are said to show a 10-times or even higher inhibitory activity against PDE4B than against PDE4D.

The compounds examined by Kenji et al. are substantially encompassed by the general formula described in US 2006/0293343A1. US 2006/0293343A1 discloses specific pharmaceutically effective PDE4-inhibiting pyrimidine compounds having an anti-inflammatory effect, of the following general formula:

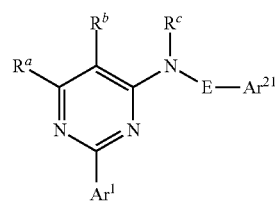

in which
Ar¹ is optionally substituted furyl, thienyl, triazolyl, thiazolyl, oxazolyl or benzothiazolyl;
E is a single bond or methylene;
Ar²¹ is an optionally substituted phenyl or naphthyl;
$R^a$ and $R^b$ in each case independently of one another is hydrogen or alkyl, alkenyl, alkynyl, alkoxy, thioalkyl, alkyl sulfinyl, alkyl sulfonyl, each of which can optionally be substituted; and $R^c$ is hydrogen or optionally substituted alkyl.

In the article by Kenji et al. the authors describe the examination of various structure-activity relationships, discussing inter alia the influence of the substituents at the 5- and 6-position on the pyrimidine ring (the substituent at the 5-position corresponds to $R^b$ in the general structural formula above, which was taken from US 2006/0293343A1, and the substituent at the 6-position corresponds to $R^a$). It can be inferred from the article that when an allyl, ethyl, cyano or formyl radical is bound at the 5-position of the pyrimidine ring, highly effective, selective PDE4B compounds were obtained. If, however, a larger radical is present at the same position, the inhibitory activity of the tested compounds decreases. With regard to possible modifications of the substituents at the 6-position of the pyrimidine ring, the authors ascertain that if methyl is replaced with ethyl at this position, the activity of the compound increases and the selectivity is lowered. Thus the authors reason that changes at the 5- and/or 6-position of the pyrimidine ring influence the activity and the selectivity of the pyrimidine compound. The authors allude to steric effects, without however giving any further information as to how the selectivity can be influenced without losing inhibitory activity.

Based on this prior art the object was now to find compounds that are preferably PDE4B-selective (i.e. to find active compounds that with a particular amount of active ingredient inhibit PDE4B but without inhibiting or only weakly inhibiting the PDE4D subtype). The advantage of such a PDE4B selectivity, as mentioned above, is that various side-effects do not (should not) occur or occur only to a small extent and that therefore a greater therapeutic range (=therapeutic window) of the pharmaceutical active ingredient is (should be) obtained. The therapeutic range of a pharmaceutical active ingredient or medicament describes the gap between its therapeutic dose and a dose that would lead to a toxic or undesired effect. The greater the therapeutic range, the rarer or more unlikely the occurrence of certain toxic or undesired side-effects and hence the safer and more tolerable the pharmaceutical active ingredient or medicament. The therapeutic range is often also referred to as the therapeutic window or therapeutic index. These names are used synonymously in the present application.

The inventors have now found pyrimidine compounds that display the desired inhibiting and PDE4B-selective property and are superior to the corresponding pyrimidine compounds of the prior art. They are therefore particularly suitable for the treatment of diseases and conditions in which inhibition of the PDE4 enzyme, in particular the PDE4B enzyme, is advantageous.

The invention thus relates to pyrimidine compounds of the following general formula (I)

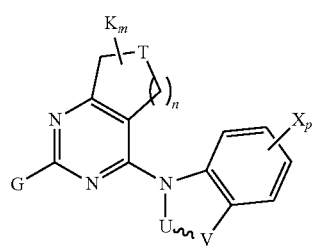

(I)

in which

G is a phenyl optionally substituted with at least one substituent Z or a 5- or 6-membered aromatic heterocycle optionally substituted with at least one substituent Z, wherein said phenyl or said aromatic heterocycle may be condensed with a 4-, 5-, 6- or 7-membered ring, being carbocyclic or heterocyclic, wherein said condensed ring may be saturated, partially unsaturated or aromatic and may be substituted with at least one substituent Z; G preferably is selected from thienyl, furanyl, thiazolyl, isothiazolyl, oxazolyl, isooxazolyl, pyridinyl, pyrimidinyl, phenyl, benzothiophenyl, benzofuranyl, benzodioxolyl, indolyl, quinolinyl, isoquinolinyl (preferably from thienyl, furanyl, thiazolyl, pyridinyl, pyrimidinyl, phenyl, benzothiophenyl, benzofuranyl, benzodioxolyl, indolyl, quinolinyl, isoquinolinyl), wherein each of aforementioned groups may be substituted with at least one substituent Z; G is preferably selected from one of the following optionally substituted groups G1 to G47

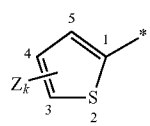
G1

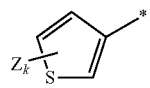
G2

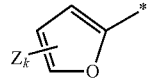
G3

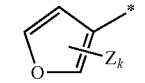
G4

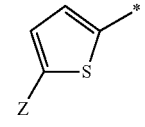
G5

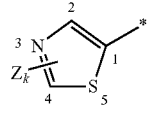
G6

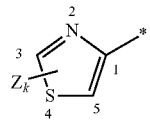
G7

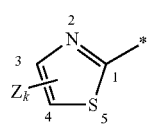
G8

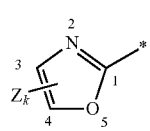
G9

-continued
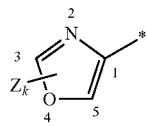 G10
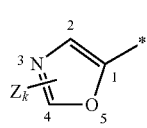 G11
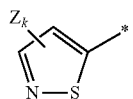 G12
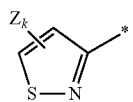 G13
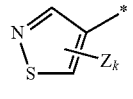 G14
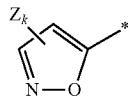 G15
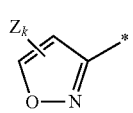 G16
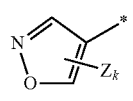 G17
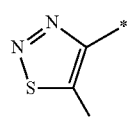 G18
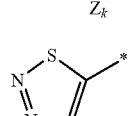 G19
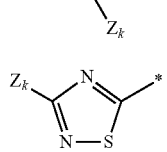 G20
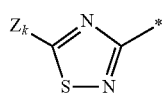 G21
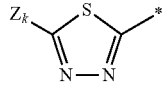 G22
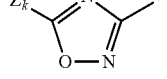 G23
-continued
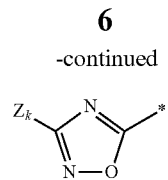 G24
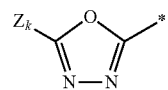 G25
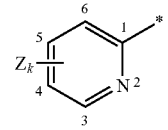 G26
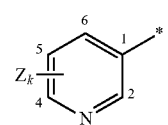 G27
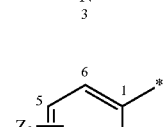 G28
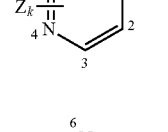 G29
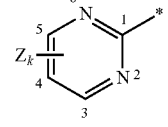 G30
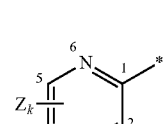 G31
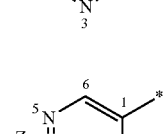 G32
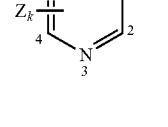 G33

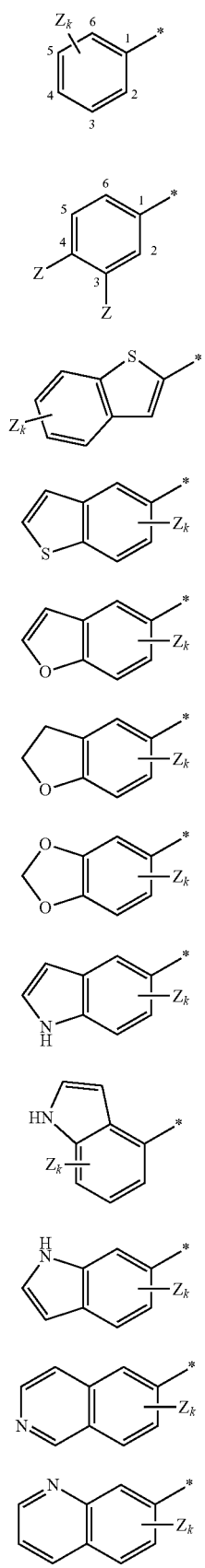

in which the site marked with an asterisk (*) indicates the binding site at position 2 of the pyrimidine ring;

G particularly preferably is selected from G1, G2, G3, G4, G5, G6, G7, G8, G9, G10, G11, G12, G13, G14, G15, G16, G17, G26, G27, G28, G29, G30, G31, G34, G35, G36, G37, G38, G39, G40, G41, G42, G43, G44, G45, G46, and G47; G most particularly preferably is selected from G1, G2, G3, G4, G5, G6, G7, G8, G26, G27, G28, G29, G30, G31, G34, G35, G36, G37, G38, G39, G40, G41, G42, G43, G44, G45, G46, G47; or from G1, G5, G8, G26, G27, G28, G31, G34, and G35;

Z independently of one another is $(C_1-C_6)$ alkyl, $(C_1-C_6)$ hydroxyalkyl, $(C_1-C_6)$ alkoxy, $(C_1-C_6)$ haloalkyl, $(C_1-C_6)$ haloalkoxy, —$S(C_1-C_6)$ alkyl, halogen, hydroxyl or cyano or is $SO_2(C_1-C_6)$alkyl, $CONH_2$, $NHSO_2(C_1-C_6)$alkyl, $NHCO(C_1-C_6)$alkyl wherein aforementioned alkyls are branched or straight-chain and can be substituted; Z preferably independently of one another is $CH_3$, $OCH_3$, $CF_3$, $CHF_2$, $CH_2F$, $OCF_3$, $OCHF_2$, $OCH_2F$, $SCH_3$, Br, Cl, F, OH or CN, or $SO_2CH_3$, $CONH_2$, $NHSO_2CH_3$, or $NHCOCH_3$;

k is 0, 1, 2, 3 or 4; if G is thienyl, furanyl, thiazoly, pyrimidyl, pyrimidinyl, benzothienyl, benzofuranyl, benzodioxolyl, benzopyrrol, benzopyridinyl then k is preferably 0 or 1; if G is a phenyl, then k is preferably 1 or 2;

T is $CR^1R^2$ or $S(O)_x$ or $S(O)=NH$; T preferably is $CH_2$, S, SO, $SO_2$ or $S(O)=NH$;

x is 0, 1 or 2; preferably 1 or 2; most preferably 2;

$R^1$ and $R^2$ independently of one another are hydrogen, $(C_1-C_6)$ alkyl, preferably $(C_1-C_4)$ alkyl, $(C_1-C_6)$ alkoxy, preferably $(C_1-C_4)$ alkoxy, $(C_1-C_6)$ haloalkyl, preferably $(C_1-C_4)$ haloalkyl, halogen, hydroxyl or cyano, wherein the aforementioned alkyl chains are branched or straight-chain and can be substituted; preferably $R^1$ and $R^2$ stand for hydrogen;

n is 1 or 2; preferably 1;

K is $(C_1-C_6)$ alkyl, preferably $(C_1-C_4)$ alkyl, $(C_1-C_6)$ alkoxy, preferably $(C_1-C_4)$ alkoxy, $(C_1-C_6)$ haloalkyl, preferably $(C_1-C_4)$ haloalkyl, halogen, hydroxyl or cyano, wherein the aforementioned alkyl chains are branched or straight-chain and can be substituted;

m is 0, 1, 2, 3 or 4; preferably m is 0;

X independently of one another is $(C_1-C_6)$ alkyl, $(C_3-C_6)$ cycloalkyl, $(C_1-C_6)$ alkoxy, $(C_3-C_6)$ cycloalkoxy, $(C_1-C_6)$ haloalkyl, $(C_1-C_6)$ haloalkoxy, halogen, hydroxyl, cyano, carboxyl, C(O)—$NH_2$, C(O)—NH$(C_1-C_6)$alkyl, C(O)—N$((C_1-C_6)$ alkyl$)_2$, $NH_2$, NH$(C_1-C_6)$alkyl, N$((C_1-C_6)$ alkyl$)_2$, N-pyrrolidinyl, N-piperidinyl, N-morpholinyl, NH—CHO, NH—C(O)—$(C_1-C_6)$alkyl, $S(O)_2$—$NH_2$, $S(C_1-C_6)$alkyl, S(O)—$(C_1-C_6)$alkyl, $S(O)_2$—$(C_1-C_6)$alkyl, O—$(C_1-C_4)$ alkyl-CN (preferably $OCH_2CN$), O—$(C_1-C_4)$alkyl-NH—CHO, O—$(C_1-C_4)$alkyl-NH—C(O)—$(C_1-C_6)$alkyl (preferably O$(CH_2)_2NCH_3)_3$), or O—$(C_1-C_4)$ alkyl-N$((C_1-C_6)$ alkyl$)_2$, or is O—$(C_1-C_4)$alkyl-O—$(C_1-C_4)$alkyl (preferably O$(CH_2)_2OCH_3$), wherein the aforementioned alkyl chains are branched or straight-chain and can be substituted, or is a chemical grouping L—CO$_2$R$^3$ or O—(C$_1$-C$_4$)alkyl-CO—R$^4$ (preferably O—CH$_2$—COR$^4$) or LCONR$^4$;

R$^3$ is hydrogen, branched or straight-chain (C$_1$-C$_6$) alkyl, preferably (C$_1$-C$_4$)alkyl; R$^3$ is preferably hydrogen or methyl;

R$^4$ is NH$_2$, NHR$^5$, NR$^5$R$^6$, (C$_1$-C$_6$) alkoxy;

R$^5$ and R$^6$ independently of one another is (C$_1$-C$_6$) alkyl, (C$_1$-C$_6$) hydroxyalkyl, (C$_3$-C$_6$) cycloalkyl (preferably as cyclopropyl), (C$_1$-C$_6$)alkyl(C$_3$-C$_6$)cycloalkyl (preferably CH$_2$-cyclopropyl), (C$_3$-C$_6$) heterocycloalkyl (such as oxetanyl, tetrahydrofuran), or R$^5$ and R$^6$, together with the nitrogen atom to which they are bound form a saturated 3- to 6-membered heterocycle, optionally substituted with branched or straight-chain (C$_1$-C$_6$) alkyl or hydroxyl groups, which heterocycle can optionally have at least one further heteroatom selected from O, S, and N; preferably R$^5$ and R$^6$, together with the nitrogen atom to which they are bound, form azetidinyl, piperazinyl, morpholinyl, pyrrolidinyl which may be optionally substituted;

preferably R$^4$ is NH$_2$, NHCH$_3$, N(CH$_3$)$_2$, NHC$_2$H$_5$, NHCH(CH$_3$)$_2$, NHCH$_2$CH$_2$OH, OCH$_3$ or one of the following groups

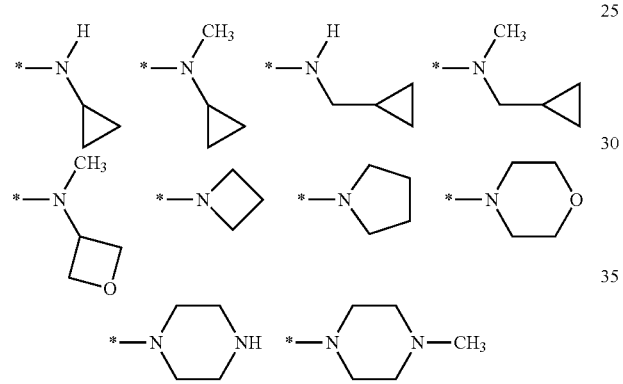

L is a bond, (C$_1$-C$_6$) alkylene, (C$_2$-C$_6$) alkenylene, —O—(C$_1$-C$_4$) alkylene, —NH—(C$_1$-C$_4$) alkylene, or —NR$^3$—(C$_1$-C$_4$) alkylene, wherein aforementioned alkylenes or alkenylenes can each be substituted with one or more halogen atoms (in particular fluorine) or wherein aforementioned alkylenes or alkenylenes can be substituted with one or more (C$_1$-C$_6$) alkyl groups (preferably methyl or ethyl), or wherein in aforementioned alkylenes or alkenylenes a CH$_2$ unit can be replaced by an oxygen atom; L preferably is a bond or methylene, wherein the methylene can be substituted with one or two halogen atoms (in particular fluorine);

P is 1, 2, 3 or 4;

U~V is a chemical grouping wherein ~stands for a single or double bond, U stands for a substituted or unsubstituted carbon atom, a substituted or unsubstituted nitrogen atom or a carbonyl group, and V stands for a substituted or unsubstituted carbon atom, a substituted or unsubstituted nitrogen atom, or an oxygen atom, preferably and in particular, the chemical grouping U~V is selected from CR$^7$R$^8$—CR$^7$R$^8$; CR$^7$=CR$^7$, N=CR$^7$, CR$^7$=N, N=N, C(=O)—CR$^7$R$^8$, and C(=O)—O; preferably is selected from CH$_2$-CH$_2$, CH=CH, N=CH, CH=N, N=N, C(=O)—CH$_2$, and C(=O)—O;

R$^7$ and R$^8$ independently of one another are hydrogen, (C$_1$-C$_4$) alkyl, (C$_1$-C$_4$) alkoxy, (C$_1$-C$_4$) haloalkyl (preferably CHF, CH$_2$F or CF$_3$), (C$_1$-C$_4$) hydroxyalkyl, halogen (preferably F, Cl, Br), hydroxyl or cyano, as well as pharmacologically tolerable salts, diastereomers, enantiomers, racemates, hydrates or solvates thereof.

Preferred compounds according to the invention have the following general formula (I-A) wherein p' is 0, 1, 2 or 3 and all substituents, chemical groupings and indices are as defined for the compounds according to formula (I)

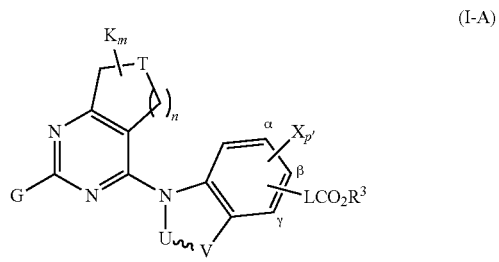

(I-A)

In principal, the group LCO$_2$R$^3$ can be bound at any position at the aromatic carbocycle. The positions marked as α, β, and γ are, however, preferred. If LCO$_2$R$^3$ is bound to the β-position, then the following general formula (I-A-1) can be drafted.

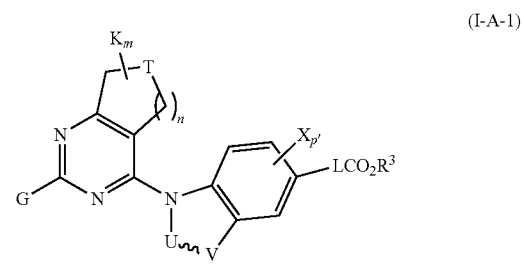

(I-A-1)

Among the compounds according to the inventions having the general formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for CH$_2$ or S(O)$_x$ with x being 0, 1 or 2, preferably 1 or 2, and the chemical grouping U~V stands for CR$^7$R$^8$—CR$^7$R$^8$ (preferably CH$_2$-CH$_2$).

Among the compounds according to the inventions having the general formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for CH$_2$ or S(O)$_x$ with x being 0, 1 or 2, preferably 1 or 2, and the chemical grouping U~V stands for CR$^7$=CR$^7$ (preferably CH=CH).

Among the compounds according to the inventions having the general formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for CH$_2$ or S(O)$_x$ with x being 0, 1 or 2, preferably 1 or 2, and the chemical grouping U~V stands for N=CR$^7$ (preferably N=CH) or CR$^7$=N (preferably N=CH).

Among the compounds according to the inventions having the generals formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for $CH_2$ or $S(O)_x$ with x being 0, 1 or 2, preferably 1 or 2, and the chemical grouping U~V stands for N=N.

Among the compounds according to the inventions having the generals formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for $CH_2$ or $S(O)_x$ with x being 0, 1 or 2, preferably 1 or 2, and the chemical grouping U~V stands for $C(=O)-CR^7R^8$ (preferably $C(=O)-CH_2$).

Among the compounds according to the inventions having the generals formula (I-A) or (I-A-1), compounds are preferred wherein L is a bond or a methylene group, G stands for optionally substituted G1, G2, G5 and G6 or substituted G34 or G35 (preferably G stands for G5 or G35) and wherein T stands for $CH_2$ or $S(O)_x$ with x being 0, 1 or 2, preferably 1 or 2, and the chemical grouping U~V stands for $C(=O)-O$.

Further preferred compounds according to the invention have the following general formula (I-B) wherein p' is 0, 1, 2 or 3 and all substituents, chemical groupings and indices are as defined for the compounds according to formula (I)

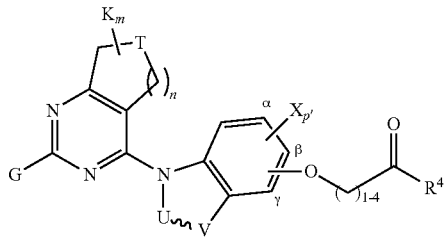

(I-B)

In principal the group $O-(C_1-C_4)$ alkyl-$COR^4$ can be bound at any position at the aromatic carbocycle. The positions marked as α, β, and γ are, however, preferred. A certain preference is given to the α- or γ-position.

In an [embodiment 1], compounds according to the inventions having the general formula (I-B) are preferred wherein G stands for optionally substituted G1, G2, G5 and G6, substituted G34 or G35 (preferably G stands for G5 or G35) or stands for one of the following groups thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, and wherein all other chemical groupings and indices including those for $R^4$ from the chemical grouping $-O-(C_1-C_4)$ alkyl-$CO-R^4$ have the definitions as described in connection with general formula (I).

Among the compounds of [embodiment 1] compounds having the following formula (I-B-1) are preferred:

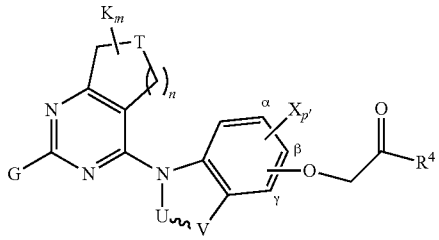

(I-B-1)

Among the compounds of formula (I-B-1) compounds are preferred wherein, the group $O-(C_1-C_4)$ alkyl-$COR^4$ can be bound at any position at the aromatic carbocycle. The positions marked as α, β, and γ are, however, preferred. A certain preference is given to the α- or γ-position.

In an [embodiment 2], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group $O-(C_1-C_4)$ alkyl-$COR^4$ or $LCO_2R^3$, or X being the group $O-(C_1-C_4)$alkyl-CN (preferably $OCH_2CN$), $O-(C_1-C_4)$ alkyl-NH—C(O)—$(C_1-C_6)$alkyl (preferably $O(CH_2)_2NCH_3)_3$), $O-(C_1-C_4)$alkyl-$O-(C_1-C_4)$alkyl (preferably $O(CH_2)_2OCH_3$), wherein the aforementioned alkyl chains are branched or straight-chain and can be substituted, or is a chemical grouping $LCONR^4$, and wherein the group X is bound at the α-, β-, or γ-position (preferably if X stands for the group $O-(C_1-C_4)$ alkyl-$COR^4$, this group is bound to the α- or γ-position, and if X stands for the $LCO_2R^3$, this group is bound to the β-position), and wherein the chemical grouping U~V stands for $CR^7R^8-CR^7R^8$ (preferably $CH_2-CH_2$) and wherein all other chemical groupings and indices have the definitions as described in connection with general formula (I).

Among the compounds of [embodiment 2], compounds are preferred wherein X is $-CO_2H$, $-CH_2CO_2H$, or $-OCH_2CON(CH_3)_2$ and wherein T stands for $CH_2$ or $S(O)_x$ with x being 1 or 2, preferably 2.

In an [embodiment 3], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group $O-(C_1-C_4)$ alkyl-$COR^4$ or $LCO_2R^3$, or X being the group $O-(C_1-C_4)$alkyl-CN (preferably $OCH_2CN$), $O-(C_1-C_4)$ alkyl-NH—C(O)—$(C_1-C_6)$alkyl (preferably $O(CH_2)_2NCH_3)_3$), $O-(C_1-C_4)$alkyl-$O-(C_1-C_4)$alkyl (preferably $O(CH_2)_2OCH_3$), wherein the aforementioned alkyl chains are branched or straight-chain and can be substituted, or is a chemical grouping $LCONR^4$, and wherein the group X is bound at the α-, β-, or γ-position (preferably if X stands for the group $O-(C_1-C_4)$ alkyl-$COR^4$, this group is bound to the α- or γ-position, and if X stands for the $LCO_2R^3$, this group is bound to the β-position), and wherein the chemical grouping U~V stands for $CR^7=CR^7$ (preferably CH=CH) and wherein all other chemical groupings and indices have the definitions as described in connection with general formula (I).

Among the compounds of [embodiment 3], compounds are preferred wherein X is $-CO_2H$, $-CH_2CO_2H$, or $-OCH_2CON(CH_3)_2$ and wherein T stands for $CH_2$ or $S(O)_x$ with x being 1 or 2, preferably 2.

In an [embodiment 4], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group O—$(C_1$-$C_4)$ alkyl-COR$^4$ or LCO$_2$R$^3$, or X being the group O—$(C_1$-$C_4)$alkyl-CN (preferably OCH$_2$CN), O—$(C_1$-$C_4)$ alkyl-NH—C(O)—$(C_1$-$C_6)$alkyl (preferably O(CH$_2)_2$NCH$_3)_3$), O—$(C_1$-$C_4)$alkyl-O—$(C_1$-$C_4)$alkyl (preferably O(CH$_2)_2$OCH$_3$), wherein the aforementioned alkyl chains are branched or straight-chain and can be substituted, or is a chemical grouping LCONR$^4$, and wherein the group X is bound at the α-, β-, or γ-position (preferably if X stands for the group O—$(C_1$-$C_4)$ alkyl-COR$^4$, this group is bound to the α- or γ-position, and if X stands for the LCO$_2$R$^3$, this group is bound to the β-position), and wherein the chemical grouping U~V stands for N=CR$^7$ (preferably N=CH) or CR$^7$=N (preferably N=CH) and wherein all other chemical groupings and indices have the definitions as described in connection with general formula (I).

Among the compounds of [embodiment 4], compounds are preferred wherein X is —CO$_2$H, —CH$_2$CO$_2$H, or —OCH$_2$CON(CH$_3)_2$ and wherein T stands for CH$_2$ or S(O)$_x$ with x being 1 or 2, preferably 2.

In an [embodiment 5], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group O—$(C_1$-$C_4)$ alkyl-COR$^4$ or LCO$_2$R$^3$, or X being the group O—$(C_1$-$C_4)$alkyl-CN (preferably OCH$_2$CN), O—$(C_1$-$C_4)$ alkyl-NH—C(O)—$(C_1$-$C_6)$alkyl (preferably O(CH$_2)_2$NCH$_3)_3$), O—$(C_1$-$C_4)$alkyl-O—$(C_1$-$C_4)$alkyl (preferably O(CH$_2)_2$OCH$_3$), wherein the aforementioned alkyl chains are branched or straight-chain and can be substituted, or is a chemical grouping LCONR$^4$, and wherein the group X is bound at the α-, β-, or γ-position (preferably if X stands for the group O—$(C_1$-$C_4)$ alkyl-COR$^4$, this group is bound to the α- or γ-position, and if X stands for the LCO$_2$R$^3$, this group is bound to the β-position), and wherein the chemical grouping U~V stands for N=N and wherein all other chemical groupings and indices have the definitions as described in connection with general formula (I).

Among the compounds of [embodiment 5], compounds are preferred wherein X is —CO$_2$H, —CH$_2$CO$_2$H, or —OCH$_2$CON(CH$_3)_2$ and wherein T stands for CH$_2$ or S(O)$_x$ with x being 1 or 2, preferably 2.

In an [embodiment 6], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group O—$(C_1$-$C_4)$ alkyl-COR$^4$ or LCO$_2$R$^3$, or X being the group O—$(C_1$-$C_4)$alkyl-CN (preferably OCH$_2$CN), O—$(C_1$-$C_4)$ alkyl-NH—C(O)—$(C_1$-$C_6)$alkyl (preferably O(CH$_2)_2$NCH$_3)_3$), O—$(C_1$-$C_4)$alkyl-O—$(C_1$-$C_4)$alkyl (preferably O(CH$_2)_2$OCH$_3$), wherein the aforementioned alkyl chains are branched or straight-chain and can be substituted, or is a chemical grouping LCONR$^4$, and wherein the group X is bound at the α-, β-, or γ-position (preferably if X stands for the group O—$(C_1$-$C_4)$ alkyl-COR$^4$, this group is bound to the α- or γ-position, and if X stands for the LCO$_2$R$^3$, this group is bound to the β-position), and wherein the chemical grouping U~V stands for C(=O)—CR$^7$R$^8$ (preferably C(=O)—CH$_2$) and wherein all other chemical groupings and indices have the definitions as described in connection with general formula (I).

Among the compounds of [embodiment 6], compounds are preferred wherein X is —CO$_2$H, —CH$_2$CO$_2$H, or —OCH$_2$CON(CH$_3)_2$ and wherein T stands for CH$_2$ or S(O)$_x$ with x being 1 or 2, preferably 2.

In an [embodiment 7], compounds according to the invention having the general formula (I) are preferred wherein G stands for optionally substituted G1, G2, G5 and G6, substituted G34 or G35 (preferably G stands for G5 or G35) or stands for one of the following thienyl, furanyl, thiazolyl, pyridinyl, pyrimidinyl, phenyl, benzothiophenyl, benzofuranyl, benzodioxolyl, indolyl, quinolinyl, isoquinolinyl, which groups can be substituted with at least one substituent K, wherein m is 0, n is 1, p is 1 with X being the group O—$(C_1$-$C_4)$ alkyl-COR$^4$ or LCO$_2$R$^3$, or X being the group O—$(C_1$-$C_4)$alkyl-CN (preferably OCH$_2$CN), O—$(C_1$-$C_4)$ alkyl-NH—C(O)—$(C_1$-$C_6)$alkyl (preferably O(CH$_2)_2$NCH$_3)_3$), O—$(C_1$-$C_4)$alkyl-O—$(C_1$-$C_4)$alkyl (preferably O(CH$_2)_2$OCH$_3$), wherein the aforementioned alkyl chains are branched or straight-chain and can be substituted, or is a chemical grouping LCONR$^4$, and wherein the group X is bound at the α-, β-, or γ-position (preferably if X stands for the group O—$(C_1$-$C_4)$ alkyl-COR$^4$, this group is bound to the α- or γ-position, and if X stands for the LCO$_2$R$^3$, this group is bound to the β-position), and wherein the chemical grouping U~V stands for C(=O)—O and wherein all other chemical groupings and indices have the definitions as described in connection with general formula (I).

Among the compounds of [embodiment 7], compounds are preferred wherein X is —CO$_2$H, —CH$_2$CO$_2$H, or —OCH$_2$CON(CH$_3)_2$ and wherein T stands for CH$_2$ or S(O)$_x$ with x being 1 or 2, preferably 2.

Unless otherwise specified, the term $(C_1$-$C_6)$ alkyl is understood to mean branched and unbranched alkyl groups consisting of 1 to 6 hydrocarbon groups. Examples of $(C_1$-$C_6)$ alkyl radicals are methyl, ethyl, n-propyl, 1-methylethyl (isopropyl), n-butyl, 1-methylpropyl, 2-methylpropyl, 1,1-dimethylethyl (tert-butyl), n-pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. $(C_1$-$C_4)$ alkyl radicals are preferred, $(C_1$-$C_3)$ alkyl radicals being particularly preferred, in particular methyl, ethyl and propyl. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted. Preferred haloalkyl radicals are CHF$_2$, CH$_2$F, CF$_3$, CH$_2$—CH$_2$F, CH$_2$—CHF$_2$, CH$_2$CF$_3$. $(C_1$-$C_6)$ haloalkyl radicals are preferred, with $(C_1$-$C_4)$ haloalkyl radicals being particularly preferred and $(C_1$-$C_3)$ haloalkyl radicals most particularly preferred, in particular CHF$_2$, CH$_2$F, CF$_3$, CH$_2$—CH$_2$F, CH$_2$—CHF$_2$ and CH$_2$CF$_3$.

Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2\text{—}CFH_2$, $OCH_2\text{—}CF_2H$, $OCH_2CF_3$. ($C_1$-$C_6$) haloalkoxy radicals are preferred, with ($C_1$-$C_4$) haloalkoxy radicals being particularly preferred and ($C_1$-$C_3$) haloalkoxy radicals most particularly preferred, in particular $OCHF_2$, $OCH_2F$, $OCF_3$, $OCH_2\text{—}CFH_2$, $OCH_2\text{—}CF_2H$, $OCH_2CF_3$.

Unless otherwise specified, the term ($C_2$-$C_6$) alkenyl is understood to mean branched and unbranched alkyl groups consisting of 2 to 6 hydrocarbon atoms and having at least one double bond. Examples of ($C_2$-$C_6$) alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation ($C_2$-$C_6$) alkenyl includes all possible isomers, i.e. structural isomers (constitutional isomers) and stereoisomers ((Z) and (E) isomers).

Unless otherwise specified, the term carbocycle is understood to mean preferably 3- to 7-membered rings consisting of hydrocarbon groups, which rings may be saturated, partially unsaturated or aromatic.

Unless otherwise specified, the term heterocycle is understood to mean preferably 5- to 7-membered rings consisting of hydrocarbon groups, which can be saturated, partially unsaturated or aromatic and which contain one or more heteroatoms selected from the group comprising nitrogen, oxygen and sulfur, preferably nitrogen and/or oxygen. Examples of saturated heterocycles are 1,4-dioxane, tetrahydrofuran and 1,4-oxathiane. Examples of aromatic or partially unsaturated heterocycles are furan, thiophene, pyridine, pyrimidine, thiazole, isothiazole, oxazole, isoxazole, pyridazine, pyrazine, indole, indazole, quinoline, isoquinoline, phthalazine and quinazoline. Unsaturated aromatic heterocycles are also called heteroaromatics.

Unless otherwise specified, carbocylces and heterocycles may be condensed with a 4-, 5-, 6- or 7-membered ring, being carbocyclic or heterocyclic, wherein said condensed ring may be saturated, partially unsaturated or aromatic. Examples of such condensed ring systems are benzothiophenyl, benzofuranyl, benzodioxolyl, indolyl, quinolinyl and isoquinolinyl Owing to their excellent pharmacological activity, the compounds according to the invention of the general structure of formula (I) and of the substructures of formula (I-A), (I-A-1) (I-B), or (I-B-1) derived from formula (I) are suitable for the treatment of various diseases or conditions in which inhibition of the PDE4 enzyme is advantageous.

Such conditions and diseases are inter alia
inflammatory diseases of the joints, in particular rheumatoid arthritis, psoriatic arthritis, ankylosing spondylitis (Bechterew's disease), gout, osteoarthritis;
inflammatory diseases of the skin, in particular psoriasis, atopic dermatitis, lichen planus;
inflammatory diseases of the eyes, in particular uveitis;
gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;
inflammatory diseases of the internal organs, in particular SLE (systemic lupus erythematosus) including lupus nephritis, chronic prostatitis, interstitial cystitis;
hyperplastic diseases, in particular benign prostatic hyperplasia;
respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;
diseases of the fibrotic spectrum, in particular hepatic fibrosis, systemic sclerosis, scleroderma;
cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;
metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);
psychological disorders, in particular schizophrenia, depression, in particular bipolar or manic depression, dementia, memory loss, generalised anxiety disorder (GAD); and
diseases of the peripheral or central nervous system, in particular Parkinson's disease, multiple sclerosis, Alzheimer's disease, stroke, ALS (amyotrophic lateral sclerosis).

One of the advantages of the compounds according to the invention of the general structure of formula (I) and of a substructure of formula (I-A), (I-A-1) (I-B), or (I-B-1) derived from formula (I) is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

The invention therefore also provides a pharmaceutical composition (medicament) containing at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio.

The invention therefore also provides a compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

The invention also provides a compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

The invention also provides a compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis, PAH (pulmonary arterial hypertension).

The invention also provides a compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of rheumatoid arthritis, psoriatic arthritis, ankylosing spondylitis (Bechterew's disease), psoriasis, COPD (chronic obstructive pulmonary disease), asthma, type 2 diabetes and/or metabolic syndrome.

The invention also provides the use of a compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

Preferred according to the invention is the use of a compound according to the invention of the general structure of formula (I) or of a compound of the general structure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis).

Preferred according to the invention is the use of a compound according to the invention of the general structure of formula (I) or of a compound of the general structure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps.

Preferred according to the invention is the use of a compound according to the invention of the general structure of formula (I) or of a compound of the general structure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of inflammatory diseases of the internal organs, in particular SLE (systemic lupus erythematosus) including lupus nephritis, chronic prostatitis, interstitial cystitis.

Preferred according to the invention is the use of a compound according to the invention of the general structure of formula (I) or of a compound of the general structure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of hyperplastic diseases, in particular benign prostatic hyperplasia.

Preferred according to the invention is the use of a compound according to the invention of the general structure of formula (I) or of a compound of the general structure of formula (I-A), (I-A-1) (I-B), or (I-B-1) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia.

Preferred according to the invention is the use of a compound according to the invention of the general structure of formula (I) or of a compound of the general structure of formula (I-A), (I-A-1) (I-B), or (I-B-1) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the fibrotic spectrum, in particular hepatic fibrosis, systemic sclerosis, scleroderma.

Preferred according to the invention is the use of a compound according to the invention of the general structure of formula (I) or of a compound of the general structure of formula (I-A), (I-A-1) (I-B), or (I-B-1) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas.

Preferred according to the invention is the use of a compound according to the invention of the general structure of formula (I) or of a compound of the general structure of formula (I-A), (I-A-1) (I-B), or (I-B-1) the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension).

Preferred according to the invention is the use of a compound according to the invention of the general structure of formula (I) or of a compound of the general structure of formula (I-A), (I-A-1) (I-B), or (I-B-1) the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of psychological disorders, in particular schizophrenia, depression, in particular bipolar or manic depression, dementia, memory loss, generalised anxiety disorder (GAD).

Preferred according to the invention is the use of a compound according to the invention of the general structure of formula (I) or of a compound of the general structure of formula (I-A), (I-A-1) (I-B), or (I-B-1) the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of diseases of the peripheral or central nervous system, in particular Parkinson's disease, multiple sclerosis, Alzheimer's disease, stroke, ALS (amyotrophic lateral sclerosis).

Particularly preferred is the use of a compound according to the invention of the general structure of formula (I) or of a compound of the general structure of formula (I-A), (I-A-1) (I-B), or (I-B-1) the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of one or more of the following diseases or conditions: rheumatoid arthritis, psoriatic arthritis, ankylosing spondylitis (Bechterew's disease), psoriasis, COPD (chronic obstructive pulmonary disease) and asthma.

The invention also provides a method for the treatment of inflammatory diseases of the joints, in particular rheumatoid arthritis, psoriatic arthritis, ankylosing spondylitis (Bechterew's disease), gout, osteoarthritis; inflammatory diseases of the skin, in particular psoriasis, atopic dermatitis, lichen planus; inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, DLS (amyotrophic lateral sclerosis) in a human, which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the joints (in particular rheumatoid arthritis, psoriatic arthritis, ankylosing spondylitis (Bechterew's disease), gout, osteoarthritis), skin (in particular psoriasis, atopic dermatitis, lichen planus) or eyes (in particular uveitis) in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps, in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of inflammatory diseases of the internal organs, in particular SLE (systemic lupus erythematosus) including lupus nephritis, chronic prostatitis and/or interstitial cystitis, in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of hyperplastic diseases, in particular benign prostatic hyperplasia, in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis and/or pneumonia in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the fibrotic spectrum, in particular hepatic fibrosis, systemic sclerosis and/or scleroderma, in a human is preferred which is characterised in that a therapeutically effective amount of at least one compound according to the invention of the general structure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of metabolic diseases, in particular type 2 diabetes, metabolic syndrome, obesity/adiposity, fatty liver disease (not alcohol-induced), and cardiovascular diseases, in particular arteriosclerosis, PDH (pulmonary arterial hypertension), in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of psychological disorders, in particular schizophrenia, depression, in particular bipolar or manic depression, dementia, memory loss and/or generalised anxiety disorder (GDD), in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of diseases of the peripheral or central nervous system, in particular Parkinson's disease, multiple sclerosis, Alzheimer's disease, stroke and/or ALS (amyotrophic lateral sclerosis), in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

A method for the treatment of one or more of the following diseases or conditions: rheumatoid arthritis, psoriatic arthritis, ankylosing spondylitis (Bechterew's disease), psoriasis, COPD (chronic obstructive pulmonary disease), asthma and also type 2 diabetes and metabolic syndrome in a human is preferred which is characterised in that a therapeutically effective amount of at least one compound according to the invention of the general structure of formula (I) or of a substructure of formula (I-A), (I-A-1) (I-B), or (I-B-1) derived from formula (I) in the presented form or in the form of its acids or bases or in the form of the pharmaceutically safe, in particular physiologically tolerable salts, or in the form of its solvates, in particular hydrates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Generally 0.01 to 500 mg/kg, in particular 0.05 to 50 mg/kg, preferably 0.1 to 25 mg/kg of body weight of at least one compound according to the invention of the general structure of formula (I) or of a substructure of formula (I-A), (I-A-1) (I-B), or (I-B-1) derived from formula (I) are administered.

The compounds according to the invention can be produced in the manner described here or in an analogous manner The compounds according to the invention can be synthesized according to general knowledge in the field of organic chemistry or in a manner as described here (cf. reaction schemes below) or analogously. The reaction conditions in the synthesis routes described herein are known to the skilled person and are for some cases exemplified in the synthesis examples herein.

i) Formation of 4-hydroxypyrimidine compound of formula (IV)

(Reaction scheme 1)

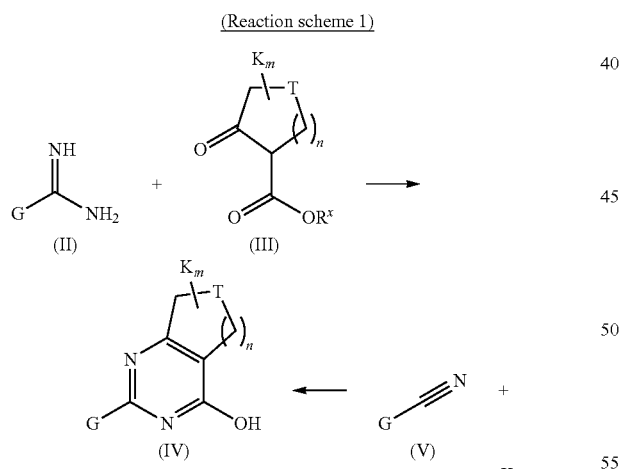

ii) Chlorination of the 4-hydroxypyrimidine compound of formula (IV) with a chlorinating agent to form a compound (VII)

(Reaction scheme 2)

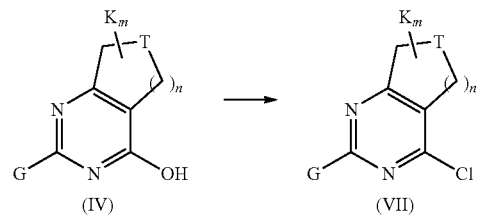

iii) Transition metal catalyzed reaction of the 4-chloropyrimidine compound of formula (VII) with a compound of formula (VIII) to form a compound of formula (IX)

(Reaction scheme 3)

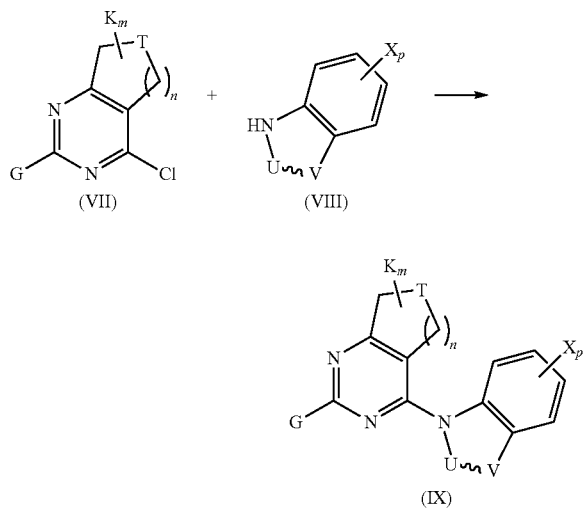

In cases where the chemical grouping U~V stands for $CR^7R^8$—$CR^7R^8$ (e.g. $CH_2$-$CH_2$) or N=$CR^7$ (e.g. N=CH), the so-called Buchwald reaction is employed using a palladium catalyst.

In cases where the chemical grouping U~V stands for $CR^7$=$CR^7$ (e.g. CH=CH) the reaction takes place in the presence of a copper catalyst.

iv) If U~V stands for C(=O)—$CR^7R^8$ (e.g. C(=O)—$CH_2$) the following 2-step process towards the formation of compound of formula (IX) starting from 4-chloropyrimidine compound of formula (VII) can be employed (Reaction scheme 4)

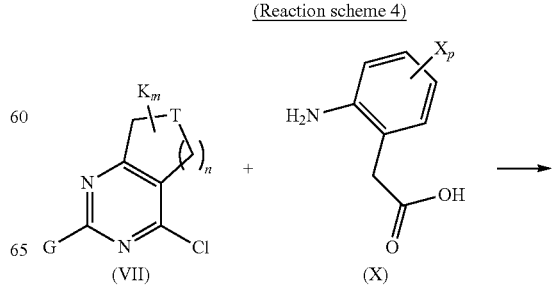

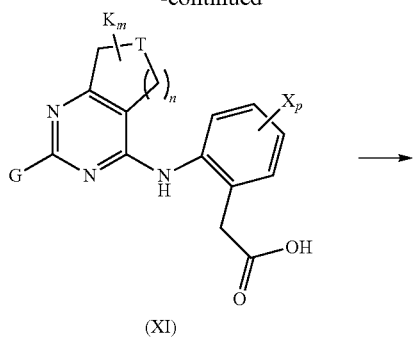

(XI)

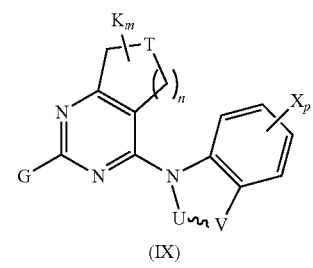

(IX)

Buchwald reaction of the amine compound of formula (X) with the 4-chloropyrimidine compound of formula (VII) followed by an intramolecular amidation reaction (reagents: trifluoroacetic anhydride and a base like diisopropylethylamine)

v) If U~V stands for CR$^7$=N (e.g. CH=N) the following 3-step process towards the formation of compound of formula (IX) starting from 4-chloropyrimidine compound of formula (VII) can be employed (Reaction scheme 5)

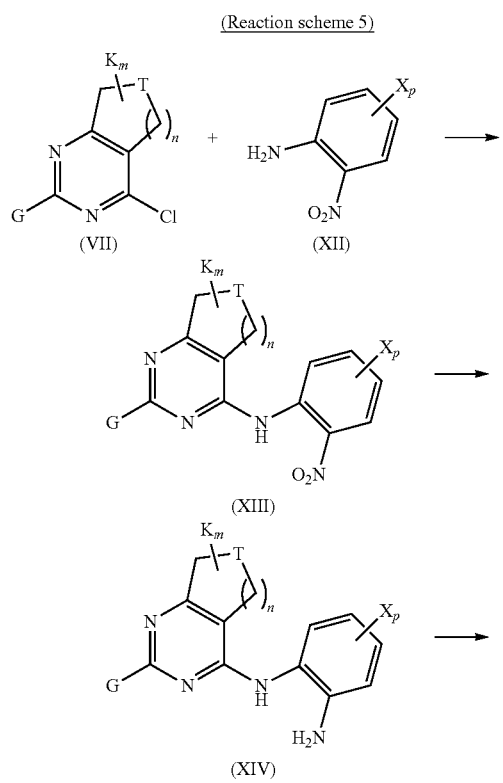

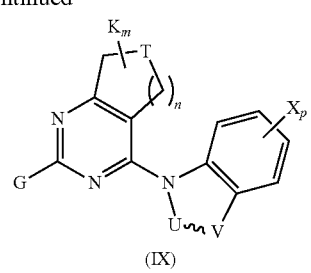

(IX)

Buchwald reaction of the amine compound of formula (XII) with the 4-chloropyrimidine compound of formula (VII). Next, the nitro group in the compound of formula (XIII) is reduced and the product (XIV) is reacted with a formic acid derivate (e.g. triethyl orthoformiate) to afford the compound of formula (IX) wherein U~V stands for CR$_7$=N (CH=N).

vi) If U~V stands for C(=O)—O a 2-step process towards the formation of compound of formula (IX) starting from 4-chloropyrimidine compound of formula (VII) can be employed (Reaction scheme 6)

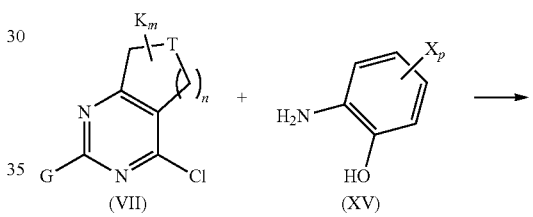

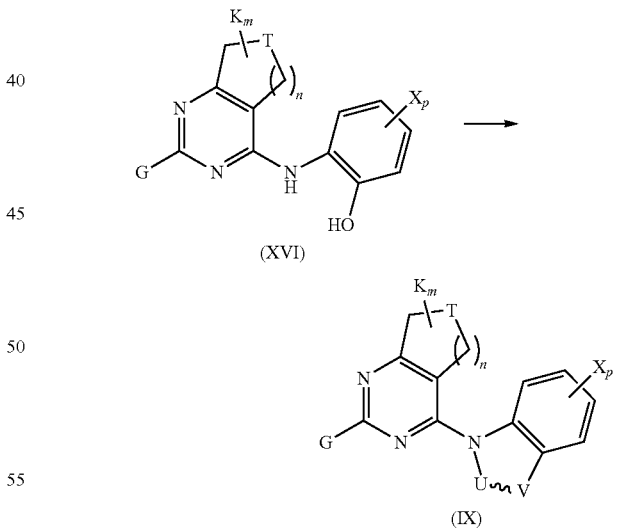

Buchwald reaction of the amine compound of formula (XV) with the 4-chloropyrimidine compound of formula (VII) followed by reaction with a phosgene equivalent like 1,1'-carbonyldiimidazole (CDI) to a compound of formula (IX) where U~V stands for C(=O)—O.

vii) Synthesis of the target compound of formula (XVIII) by acid or basic ester cleavage of the compound of formula (XVII)

(Reaction scheme 7)

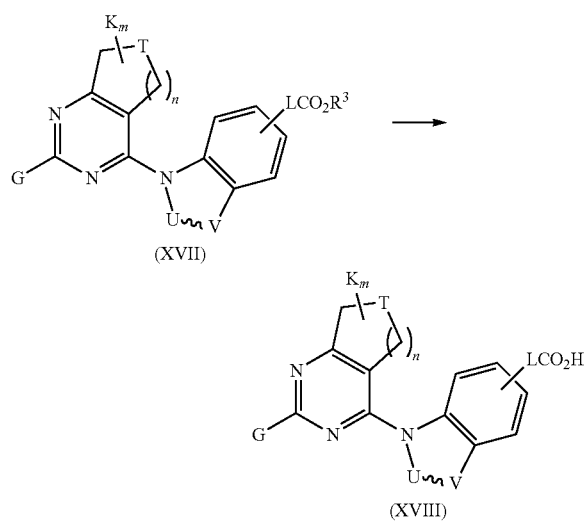

viii) Oxidation of the thioether compound of formula (XIX) towards the corresponding sulfoxide (XX)

(Reaction scheme 8)

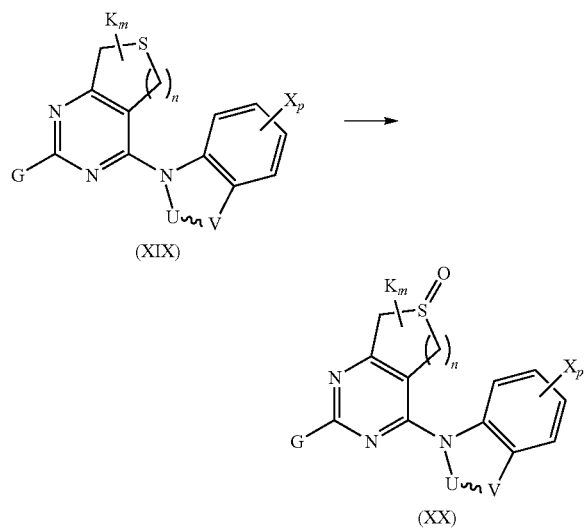

ix) Oxidation of the thioether compound of formula (XIX) towards the corresponding sulfone (XXI)

(Reaction scheme 9)

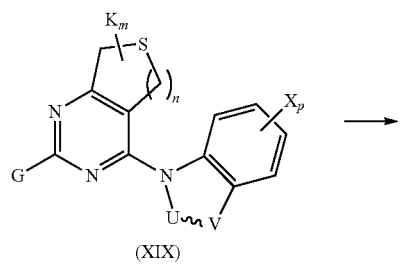

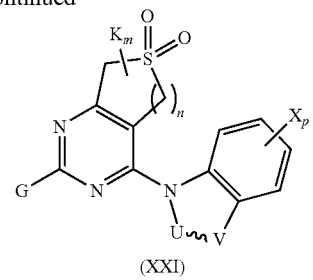

x) Reaction of a compound of formula (XXII) with a compound of formula (VIII) to form a compound of formula (XXIII) wherein U~V stands for $CR^7R^8$—$CR^7R^8$ (e.g. $CH_2$-$CH_2$)

(Reaction scheme 10)

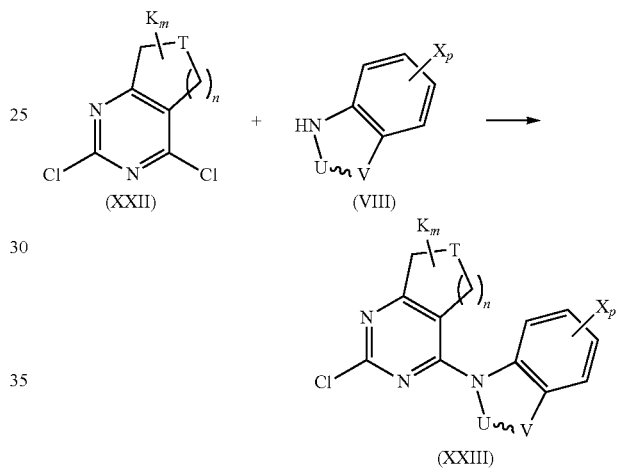

Unless otherwise specified, the radicals $R^x$ in the general formulae of the compounds that are used or reacted in the aforementioned methods are defined as follows:

$R^x$ is ($C_1$-$C_6$) alkyl, preferably methyl.

The compounds according to the invention are specified in the table below, without limiting the invention thereto.

In the tables the following abbreviations were used: Me=methyl, Et=ethyl, site=binding site of the LCO2R3 group (table 1) or the OCH2COR4 group (table 2),

TABLE 1

(I-A-2)

| Cpd. No. | G | Z | U~V | T | site | L | R3 | n |
|---|---|---|---|---|---|---|---|---|
| 1-1 | G34 | 3-F, 4-MeO | CH2—CH2 | CH2 | β | CH2 | H | 1 |
| 1-2 | G34 | 3-Cl, 4-MeO | CH2—CH2 | CH2 | β | CH2 | H | 1 |

TABLE 1-continued (I-A-2)

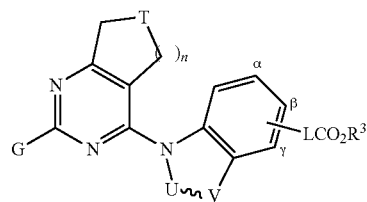 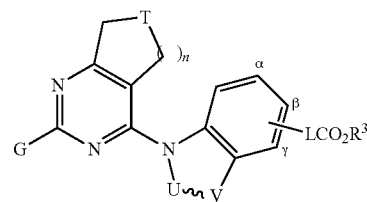

| Cpd. No. | G | Z | U~V | T | site | L | R3 | n |
|---|---|---|---|---|---|---|---|---|
| 1-3 | G34 | 4-MeO | CH2—CH2 | CH2 | β | CH2 | H | 1 |
| 1-4 | G34 | 3-F, 4-MeO | CH2—CH2 | S | β | CH2 | H | 1 |
| 1-5 | G34 | 3-Cl, 4-MeO | CH2—CH2 | S | β | CH2 | H | 1 |
| 1-6 | G34 | 4-MeO | CH2—CH2 | S | β | CH2 | H | 1 |
| 1-7 | G34 | 3-F, 4-MeO | CH2—CH2 | S=O | β | CH2 | H | 1 |
| 1-8 | G34 | 3-Cl, 4-MeO | CH2—CH2 | S=O | β | CH2 | H | 1 |
| 1-9 | G34 | 4-MeO | CH2—CH2 | S=O | β | CH2 | H | 1 |
| 1-10 | G34 | 3-F, 4-MeO | CH2—CH2 | SO2 | β | CH2 | H | 1 |
| 1-11 | G34 | 3-Cl, 4-MeO | CH2—CH2 | SO2 | β | CH2 | H | 1 |
| 1-12 | G34 | 4-MeO | CH2—CH2 | SO2 | β | CH2 | H | 1 |
| 1-13 | G5 | Cl | CH2—CH2 | CH2 | β | CH2 | H | 1 |
| 1-14 | G5 | Cl | CH2—CH2 | CH2 | β | CH2 | CH3 | 1 |
| 1-15 | G5 | F | CH2—CH2 | CH2 | β | CH2 | H | 1 |
| 1-16 | G5 | CN | CH2—CH2 | CH2 | β | CH2 | H | 1 |
| 1-17 | G6 | — | CH2—CH2 | CH2 | β | CH2 | H | 1 |
| 1-18 | G1 | 4-Cl | CH2—CH2 | CH2 | β | CH2 | H | 1 |
| 1-19 | G2 | 4-Cl | CH2—CH2 | CH2 | β | CH2 | H | 1 |
| 1-20 | G5 | Cl | CH2—CH2 | S | β | CH2 | H | 1 |
| 1-21 | G5 | Cl | CH2—CH2 | S=O | β | CH2 | H | 1 |
| 1-22 | G5 | Cl | CH2—CH2 | SO2 | β | CH2 | H | 1 |
| 1-23 | G5 | F | CH2—CH2 | S | β | CH2 | H | 1 |
| 1-24 | G5 | F | CH2—CH2 | S=O | β | CH2 | H | 1 |
| 1-25 | G5 | F | CH2—CH2 | SO2 | β | CH2 | H | 1 |
| 1-26 | G5 | CN | CH2—CH2 | S | β | CH2 | H | 1 |
| 1-27 | G5 | CN | CH2—CH2 | S=O | β | CH2 | H | 1 |
| 1-28 | G5 | CN | CH2—CH2 | SO2 | β | CH2 | H | 1 |
| 1-29 | G6 | — | CH2—CH2 | S | β | CH2 | H | 1 |
| 1-30 | G6 | — | CH2—CH2 | S=O | β | CH2 | H | 1 |
| 1-31 | G6 | — | CH2—CH2 | SO2 | β | CH2 | H | 1 |
| 1-32 | G1 | 4-Cl | CH2—CH2 | S | β | CH2 | H | 1 |
| 1-33 | G1 | 4-Cl | CH2—CH2 | S=O | β | CH2 | H | 1 |
| 1-34 | G1 | 4-Cl | CH2—CH2 | SO2 | β | CH2 | H | 1 |
| 1-35 | G2 | 4-Cl | CH2—CH2 | S | β | CH2 | H | 1 |
| 1-36 | G2 | 4-Cl | CH2—CH2 | S=O | β | CH2 | H | 1 |
| 1-37 | G2 | 4-Cl | CH2—CH2 | SO2 | β | CH2 | H | 1 |
| 1-38 | G34 | 3-F, 4-MeO | CH2—CH2 | CH2 | β | CH2 | H | 2 |
| 1-39 | G34 | 3-Cl, 4-MeO | CH2—CH2 | CH2 | β | CH2 | H | 2 |
| 1-40 | G34 | 4-MeO | CH2—CH2 | CH2 | β | CH2 | H | 2 |
| 1-41 | G34 | 3-F, 4-MeO | CH2—CH2 | S | β | CH2 | H | 2 |
| 1-42 | G34 | 3-Cl, 4-MeO | CH2—CH2 | S | β | CH2 | H | 2 |
| 1-43 | G34 | 4-MeO | CH2—CH2 | S | β | CH2 | H | 2 |
| 1-44 | G34 | 3-F, 4-MeO | CH2—CH2 | S=O | β | CH2 | H | 2 |
| 1-45 | G34 | 3-Cl, 4-MeO | CH2—CH2 | S=O | β | CH2 | H | 2 |
| 1-46 | G34 | 4-MeO | CH2—CH2 | S=O | β | CH2 | H | 2 |
| 1-47 | G34 | 3-F, 4-MeO | CH2—CH2 | SO2 | β | CH2 | H | 2 |
| 1-48 | G34 | 3-Cl, 4-MeO | CH2—CH2 | SO2 | β | CH2 | H | 2 |
| 1-49 | G34 | 4-MeO | CH2—CH2 | SO2 | β | CH2 | H | 2 |
| 1-50 | G5 | Cl | CH2—CH2 | CH2 | β | CH2 | H | 2 |
| 1-51 | G5 | Cl | CH2—CH2 | CH2 | β | CH2 | CH3 | 2 |
| 1-52 | G5 | F | CH2—CH2 | CH2 | β | CH2 | H | 2 |
| 1-53 | G5 | Cl | CH2—CH2 | S | β | CH2 | H | 2 |
| 1-54 | G5 | Cl | CH2—CH2 | S=O | β | CH2 | H | 2 |
| 1-55 | G5 | Cl | CH2—CH2 | SO2 | β | CH2 | H | 2 |
| 1-56 | G5 | F | CH2—CH2 | S | β | CH2 | H | 2 |
| 1-57 | G5 | F | CH2—CH2 | S=O | β | CH2 | H | 2 |
| 1-58 | G5 | F | CH2—CH2 | SO2 | β | CH2 | H | 2 |
| 1-59 | G34 | 3-Cl, 4-MeO | N=CH | CH2 | β | CH2 | H | 1 |
| 1-60 | G34 | 3-F, 4-MeO | N=CH | CH2 | β | CH2 | H | 1 |
| 1-61 | G5 | Cl | N=CH | CH2 | β | CH2 | H | 1 |
| 1-62 | G5 | Cl | CH=N | CH2 | β | CH2 | H | 1 |
| 1-63 | G5 | Cl | CH=N | CH2 | β | bond | H | 1 |
| 1-64 | G5 | Cl | C(=O)—CH2 | CH2 | β | CH2 | H | 1 |
| 1-65 | G5 | F | C(=O)—CH2 | CH2 | β | CH2 | H | 1 |
| 1-66 | G34 | 3-Cl, 4-MeO | C(=O)—CH2 | CH2 | β | CH2 | H | 1 |
| 1-67 | G5 | Cl | C(=O)—O | CH2 | β | CH2 | H | 1 |
| 1-68 | G5 | Cl | C(=O)—O | CH2 | β | bond | H | 1 |
| 1-69 | G5 | Cl | C(=O)—CH2 | CH2 | β | bond | H | 1 |
| 1-70 | G5 | Cl | CH=CH | CH2 | β | bond | H | 1 |
| 1-71 | G5 | Cl | CH=CH | CH2 | β | CH2 | H | 1 |
| 1-72 | G5 | Cl | CH2—CH2 | CH2 | β | bond | H | 1 |
| 1-73 | G5 | Cl | N=CH | CH2 | β | bond | H | 1 |
| 1-74 | G5 | Cl | CH=N | CH2 | α | bond | H | 1 |
| 1-75 | G5 | CONH2 | CH2—CH2 | CH2 | β | CH2 | H | 1 |
| 1-76 | G34 | 3-Cl, 4-MeO | CH2—CH2 | CH2 | γ | OCH2 | H | 1 |
| 1-77 | G5 | Cl | CH2—CH2 | SO2 | α | OCH2 | CH3 | 1 |
| 1-78 | G5 | Cl | CH2—CH2 | SO2 | β | CH2 | CH3 | 1 |
| 1-79 | G5 | Cl | CH2—CH2 | CH2 | β | OCH2 | CH3 | 1 |
| 1-80 | G36 | — | CH2—CH2 | S=O | β | CH2 | H | 1 |
| 1-81 | G38 | — | CH2—CH2 | S=O | β | CH2 | H | 1 |

TABLE 2

(I-B-2)

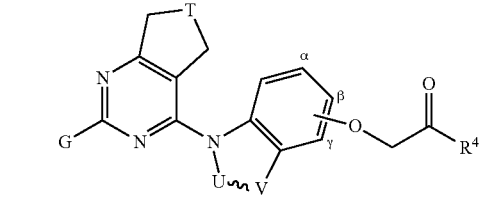

| Cpd. No. | G | Z | U~V | T | site | R4 |
|---|---|---|---|---|---|---|
| 2-1 | G34 | 4-OMe | CH2—CH2 | S | γ | NMe2 |
| 2-2 | G34 | 4-OMe | CH2—CH2 | SO2 | γ | NMe2 |
| 2-3 | G34 | 3-F | CH2—CH2 | S | γ | NMe2 |
| 2-4 | G34 | 3-F | CH2—CH2 | SO2 | γ | NMe2 |
| 2-5 | G34 | 3-Cl | CH2—CH2 | S | γ | NMe2 |
| 2-6 | G34 | 3-Cl | CH2—CH2 | SO2 | γ | NMe2 |
| 2-7 | G34 | 4-OMe, 3-Cl | CH2—CH2 | S | γ | NMe2 |
| 2-8 | G34 | 4-OMe, 3-Cl | CH2—CH2 | SO2 | γ | NMe2 |
| 2-9 | G34 | 4-OMe, 3-F | CH2—CH2 | S | γ | NMe2 |
| 2-10 | G34 | 4-OMe, 3-F | CH2—CH2 | SO2 | γ | NMe2 |

TABLE 2-continued (I-B-2)

| Cpd. No. | G | Z | U~V | T | site | R4 |
|---|---|---|---|---|---|---|
| 2-11 | G34 | 4-F, 3-F | CH2—CH2 | S | γ | NMe2 |
| 2-12 | G34 | 4-F, 3-F | CH2—CH2 | SO2 | γ | NMe2 |
| 2-13 | G5 | Cl | CH2—CH2 | SO2 | γ | NMe2 |
| 2-14 | G5 | F | CH2—CH2 | CH2 | γ | NMe2 |
| 2-15 | G5 | F | CH2—CH2 | S | γ | NMe2 |
| 2-16 | G5 | F | CH2—CH2 | S=O | γ | NMe2 |
| 2-17 | G5 | F | CH2—CH2 | SO2 | γ | NMe2 |
| 2-18 | G34 | 4-OMe | CH2—CH2 | S=O | α | NMe2 |
| 2-19 | G34 | 4-OMe | CH2—CH2 | S | α | NMe2 |
| 2-20 | G34 | 4-OMe | CH2—CH2 | S=O | α | NMe2 |
| 2-21 | G34 | 4-OMe | CH2—CH2 | SO2 | α | NMe2 |
| 2-22 | G34 | 3-F | CH2—CH2 | CH2 | α | NMe2 |
| 2-23 | G34 | 3-F | CH2—CH2 | S | α | NMe2 |
| 2-24 | G34 | 3-F | CH2—CH2 | S=O | α | NMe2 |
| 2-25 | G34 | 3-F | CH2—CH2 | SO2 | α | NMe2 |
| 2-26 | G34 | 3-Cl | CH2—CH2 | CH2 | α | NMe2 |
| 2-27 | G34 | 3-Cl | CH2—CH2 | S | α | NMe2 |
| 2-28 | G34 | 3-Cl | CH2—CH2 | S=O | α | NMe2 |
| 2-29 | G34 | 3-Cl | CH2—CH2 | SO2 | α | NMe2 |
| 2-30 | G34 | 4-OMe, 3-Cl | CH2—CH2 | CH2 | α | NMe2 |
| 2-31 | G34 | 4-OMe, 3-Cl | CH2—CH2 | S | α | NMe2 |
| 2-32 | G34 | 4-OMe, 3-Cl | CH2—CH2 | S=O | α | NMe2 |
| 2-33 | G34 | 4-OMe, 3-Cl | CH2—CH2 | SO2 | α | NMe2 |
| 2-34 | G34 | 4-OMe, 3-F | CH2—CH2 | CH2 | α | NMe2 |
| 2-35 | G34 | 4-OMe, 3-F | CH2—CH2 | S | α | NMe2 |
| 2-36 | G34 | 4-OMe, 3-F | CH2—CH2 | S=O | α | NMe2 |
| 2-37 | G34 | 4-OMe, 3-F | CH2—CH2 | SO2 | α | NMe2 |
| 2-38 | G34 | 4-F, 3-F | CH2—CH2 | CH2 | α | NMe2 |
| 2-39 | G34 | 4-F, 3-F | CH2—CH2 | S | α | NMe2 |
| 2-40 | G34 | 4-F, 3-F | CH2—CH2 | S=O | α | NMe2 |
| 2-41 | G34 | 4-F, 3-F | CH2—CH2 | SO2 | α | NMe2 |
| 2-42 | G5 | Cl | CH2—CH2 | CH2 | α | NMe2 |
| 2-43 | G5 | Cl | CH2—CH2 | S | α | NMe2 |
| 2-44 | G5 | Cl | CH2—CH2 | S=O | α | NMe2 |
| 2-45 | G5 | Cl | CH2—CH2 | SO2 | α | NMe2 |
| 2-46 | G5 | F | CH2—CH2 | CH2 | α | NMe2 |
| 2-47 | G5 | F | CH2—CH2 | S | α | NMe2 |
| 2-48 | G5 | F | CH2—CH2 | S=O | α | NMe2 |
| 2-49 | G5 | F | CH2—CH2 | SO2 | α | NMe2 |
| 2-50 | G5 | CN | CH2—CH2 | CH2 | α | NMe2 |
| 2-51 | G5 | CN | CH2—CH2 | S | α | NMe2 |
| 2-52 | G5 | CN | CH2—CH2 | S=O | α | NMe2 |
| 2-53 | G5 | CN | CH2—CH2 | SO2 | α | NMe2 |
| 2-54 | G5 | Cl | CH2—CH2 | SO2 | α | NH(CHMe2) |
| 2-55 | G5 | Cl | CH2—CH2 | SO2 | α | NHEt |
| 2-56 | G5 | Cl | CH2—CH2 | SO2 | α | N(Me)(cyclopropyl) |
| 2-57 | G5 | Cl | CH2—CH2 | SO2 | α | N(CH3)(CH2-cyclopropyl) |
| 2-58 | G5 | Cl | CH2—CH2 | SO2 | α | NHMe |
| 2-59 | G5 | Cl | CH2—CH2 | SO2 | α | NH2 |
| 2-60 | G5 | Cl | CH2—CH2 | SO2 | α | NH(oxetan-3-yl) |
| 2-61 | G5 | Cl | CH2—CH2 | SO2 | α | NH(cyclopropyl) |
| 2-62 | G5 | Cl | CH2—CH2 | SO2 | α | NH((CH2)2OH) |
| 2-64 | G5 | Cl | CH2—CH2 | CH2 | α | N(Me)(cyclopropyl) |
| 2-65 | G5 | Cl | CH2—CH2 | CH2 | α | NH(oxetan-3-yl) |
| 2-66 | G5 | Cl | CH2—CH2 | CH2 | α | NH(CHMe2) |
| 2-67 | G5 | Cl | CH2—CH2 | CH2 | α | N(CH3)(CH2-cyclopropyl) |
| 2-68 | G5 | Cl | CH2—CH2 | CH2 | α | NHEt |
| 2-69 | G5 | Cl | CH2—CH2 | CH2 | α | NH((CH2)2OH) |
| 2-70 | G5 | Cl | CH2—CH2 | CH2 | α | NHMe |
| 2-71 | G5 | Cl | CH2—CH2 | CH2 | α | NH2 |
| 2-72 | G5 | Cl | N=CH | S=O | α | NMe2 |
| 2-73 | G5 | Cl | CH=CH | S=O | α | NMe2 |
| 2-74 | G5 | Cl | CH=N | S=O | α | NMe2 |
| 2-75 | G5 | Cl | CH=N | S=O | β | NMe2 |
| 2-76 | G5 | Cl | C(=O)—O | S=O | α | NMe2 |
| 2-77 | G34 | 4-CN, 3-F | CH2—CH2 | S=O | α | NMe2 |
| 2-78 | G34 | 4-Cl, 3-F | CH2—CH2 | S=O | α | NMe2 |
| 2-79 | G34 | 4-OH, 3-F | CH2—CH2 | S=O | α | NMe2 |

TABLE 2-continued (I-B-2)

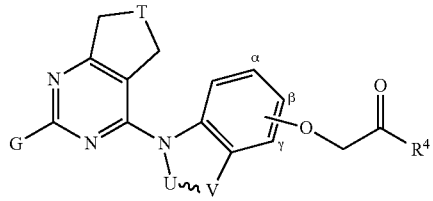

| Cpd. No. | G | Z | U~V | T | site | R4 |
|---|---|---|---|---|---|---|
| 2-80 | G5 | CONH2 | CH2—CH2 | S=O | α | NMe2 |
| 2-81 | G5 | CONH2 | CH2—CH2 | SO2 | α | NMe2 |
| 2-82 | G5 | CN | CH2—CH2 | S=O | α | NMe2 |
| 2-83 | G5 | CN | CH2—CH2 | SO2 | α | NMe2 |
| 2-84 | G5 | CN | CH2—CH2 | CH2 | α | NMe2 |
| 2-85 | G5 | CONH2 | CH2—CH2 | CH2 | α | NMe2 |
| 2-86 | G34 | 3-F, 4-Br | CH2—CH2 | S=O | α | NMe2 |
| 2-87 | G34 | 4-Me | CH2—CH2 | S=O | α | NMe2 |
| 2-88 | G34 | 2-OMe | CH2—CH2 | S=O | α | NMe2 |
| 2-89 | G34 | 3-Cl | CH2—CH2 | S=O | α | NMe2 |
| 2-90 | G34 | 4-Cl | CH2—CH2 | S=O | α | NMe2 |
| 2-91 | G34 | 3-OMe | CH2—CH2 | S=O | α | NMe2 |
| 2-92 | G34 | 4-CN | CH2—CH2 | S=O | α | NMe2 |
| 2-93 | G34 | — | CH2—CH2 | S=O | α | NMe2 |
| 2-94 | G34 | 2-Me | CH2—CH2 | S=O | α | NMe2 |
| 2-95 | G34 | 3-Me | CH2—CH2 | S=O | α | NMe2 |
| 2-96 | G34 | 2-Cl | CH2—CH2 | S=O | α | NMe2 |
| 2-97 | G34 | 2-CF3 | CH2—CH2 | S=O | α | NMe2 |
| 2-98 | G34 | 3-CN | CH2—CH2 | S=O | α | NMe2 |
| 2-99 | G34 | 4-F | CH2—CH2 | S=O | α | NMe2 |
| 2-100 | G34 | 2-F | CH2—CH2 | S=O | α | NMe2 |
| 2-101 | G34 | 3-CF3 | CH2—CH2 | S=O | α | NMe2 |
| 2-102 | G4 | — | CH2—CH2 | S=O | α | NMe2 |
| 2-103 | G34 | 2-CN | CH2—CH2 | S=O | α | NMe2 |
| 2-104 | G34 | 2-NHSO2Me | CH2—CH2 | S=O | α | NMe2 |
| 2-105 | G27 | 2-OMe | CH2—CH2 | S=O | α | NMe2 |
| 2-106 | G34 | 4-SO2Me | CH2—CH2 | S=O | α | NMe2 |
| 2-107 | G34 | 3-SO2Me | CH2—CH2 | S=O | α | NMe2 |
| 2-108 | G34 | 3-CONH2 | CH2—CH2 | S=O | α | NMe2 |
| 2-109 | G34 | 4-NHCOMe | CH2—CH2 | S=O | α | NMe2 |
| 2-110 | G34 | 4-OEt | CH2—CH2 | S=O | α | NMe2 |
| 2-111 | G34 | 3-OMe, 4-Cl | CH2—CH2 | S=O | α | NMe2 |
| 2-112 | G34 | 2-OMe, 4-F | CH2—CH2 | S=O | α | NMe2 |
| 2-113 | G34 | 2-F, 5-F | CH2—CH2 | S=O | α | NMe2 |
| 2-114 | G5 | Cl | CH2—CH2 | CH2 | α | ![NHcyclopropyl] |
| 2-115 | G34 | 3-F, 4-OMe | CH2—CH2 | S(O)=NH | α | NMe2 |
| 2-116 | G5 | Cl | CH2—CH2 | S=O | α | ![pyrrolidinyl] |
| 2-117 | G5 | Cl | CH2—CH2 | S=O | α | ![N-methylpiperazinyl] |
| 2-118 | G5 | Cl | CH2—CH2 | S=O | α | ![morpholinyl] |
| 2-119 | G34 | 3-F, 4-OMe | CH2—CH2 | S=O | α | ![pyrrolidinyl] |
| 2-120 | G5 | F | CH2—CH2 | S=O | α | ![pyrrolidinyl] |
| 2-121 | G34 | 4-OMe | CH2—CH2 | S=O | α | ![pyrrolidinyl] |
| 2-122 | G5 | Cl | CH2—CH2 | S=O | α | ![azetidinyl] |
| 2-123 | G5 | Cl | CH2—CH2 | SO2 | α | ![N-methylpiperazinyl] |
| 2-124 | G5 | Cl | CH2—CH2 | SO2 | α | NHCH(CH3)2 |
| 2-125 | G5 | Cl | CH2—CH2 | SO2 | α | ![morpholinyl] |
| 2-126 | G5 | Cl | CH2—CH2 | SO2 | α | ![pyrrolidinyl] |
| 2-127 | G5 | Cl | CH2—CH2 | CH2 | α | ![azetidinyl] |
| 2-128 | G5 | Cl | CH2—CH2 | CH2 | α | ![morpholinyl] |
| 2-129 | G5 | Cl | CH2—CH2 | CH2 | α | ![N-methylpiperazinyl] |

TABLE 2-continued

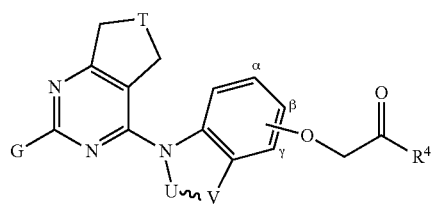

(I-B-2)

| Cpd. No. | G | Z | U~V | T | site | R4 |
|---|---|---|---|---|---|---|
| 2-130 | G28 | — | CH2—CH2 | SO2 | α | N-pyrrolidinyl |
| 2-131 | G28 | — | CH2—CH2 | SO2 | α | N-azetidinyl |
| 2-132 | G28 | — | CH2—CH2 | SO2 | α | NMe2 |
| 2-133 | G28 | — | CH2—CH2 | S=O | α | N-pyrrolidinyl |
| 2-134 | G28 | — | CH2—CH2 | S=O | α | N-azetidinyl |
| 2-135 | G28 | — | CH2—CH2 | S=O | α | NMe2 |
| 2-136 | G27 | — | CH2—CH2 | SO2 | α | NMe2 |
| 2-137 | G27 | — | CH2—CH2 | S=O | α | NMe2 |
| 2-138 | G28 | 3-F | CH2—CH2 | S=O | α | NMe2 |
| 2-139 | G27 | 4-OMe | CH2—CH2 | S=O | α | NMe2 |
| 2-140 | G6 | 3-Me | CH2—CH2 | S=O | α | NMe2 |
| 2-141 | G26 | 4-OMe | CH2—CH2 | S=O | α | NMe2 |
| 2-142 | G5 | Cl | CH2—CH2 | CH2 | α | N-pyrrolidinyl |
| 2-143 | G26 | 4-OMe | CH2—CH2 | SO2 | α | NMe2 |
| 2-144 | G31 | — | CH2—CH2 | S=O | α | NMe2 |
| 2-145 | G40 | — | CH2—CH2 | S=O | α | NMe2 |
| 2-146 | G47 | — | CH2—CH2 | S=O | α | NMe2 |
| 2-147 | G43 | — | CH2—CH2 | S=O | α | NMe2 |
| 2-148 | G44 | — | CH2—CH2 | S=O | α | NMe2 |
| 2-149 | G45 | — | CH2—CH2 | S=O | α | NMe2 |
| 2-150 | G46 | — | CH2—CH2 | S=O | α | NMe2 |
| 2-151 | G42 | — | CH2—CH2 | S=O | α | NMe2 |
| 2-152 | G41 | — | CH2—CH2 | S=O | α | NMe2 |
| 2-153 | G39 | — | CH2—CH2 | S=O | α | NMe2 |
| 2-154 | G38 | — | CH2—CH2 | S=O | α | NMe2 |
| 2-155 | G37 | — | CH2—CH2 | S=O | α | NMe2 |

TABLE 3

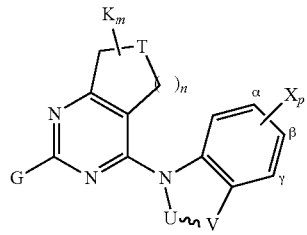

(I)

| Cpd. No. | G | Z | T | U~V | n | p | X | K | m | site |
|---|---|---|---|---|---|---|---|---|---|---|
| 3-1 | G5 | Cl | SO2 | CH2-CH2 | 1 | 1 | OCH2CN | — | 0 | α |
| 3-2 | G5 | Cl | SO2 | CH2-CH2 | 1 | 1 | OCH2CH2OMe | — | 0 | α |
| 3-3 | G5 | Cl | SO2 | CH2-CH2 | 1 | 1 | OCH2CH2NMe2 | — | 0 | α |
| 3-4 | G5 | Cl | SO2 | CH2-CH2 | 1 | 1 | CH2CONHEt | — | 0 | β |
| 3-5 | G5 | Cl | SO2 | CH2-CH2 | 1 | 1 | CH2CONHMe | — | 0 | β |
| 3-6 | G5 | Cl | SO2 | CH2-CH2 | 1 | 1 | CH2CONH2 | — | 0 | β |
| 3-7 | G5 | Cl | CH2 | CH2-CH2 | 1 | 1 | OCH2CH2NMe | — | 0 | α |
| 3-8 | G5 | Cl | SO2 | CH2-CH2 | 1 | 1 | CH2CONMe2 | — | 0 | α |

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the invention of the general structure of formula (I) or of a substructure of formula (I-A), (I-A-1) (I-B), or (I-B-1) derived from formula (I), according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic rubbers, *acacia* gum, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the invention of the general structure (I) in a depot formulation, in dissolved form or in a plaster, optionally with addition of agents promoting skin penetration, are suitable preparations for percutaneous administration. Preparation forms that are suitable for rectal, transmucosal, parenteral, oral or percutaneous administration can deliver the compounds according to the invention of the general structure (I) on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17$^{th}$ edition, Mack Publishing Company, Easton PD (1985), in particular in part 8, chapters 76 to 93.

Thus, for example, for a solid formulation such as a tablet, the active ingredient of the medicament, i.e. a compound of the general structure of formula (I) or of a substructure of formula (I-A), (I-A-1) (I-B), or (I-B-1) derived from formula (I) or of one of its pharmaceutically acceptable salts is granulated with a pharmaceutical carrier, e.g. conventional tablet ingredients such as corn starch, lactose, sucrose, sorbitol, talc, magnesium stearate, dicalcium phosphate or pharmaceutically acceptable rubbers, and pharmaceutical diluting agents such as water for example, to form a solid composition containing a compound according to the invention or a pharmaceutically acceptable salt thereof in a homogeneous distribution. A homogeneous distribution is understood here to mean that the active ingredient is evenly distributed throughout the entire composition so that the composition can be readily divided into identically effective single-unit dosage forms such as tablets, pills or capsules. The solid composition is then divided into single-unit dosage forms. The tablets or pills of the medicament according to the invention or of the compositions according to the invention can also be coated or compounded in another way so as to provide a delayed-release dosage form. Suitable coating agents are inter alia polymeric acids and mixtures of polymeric acids with materials such as for example shellac, cetyl alcohol and/or cellulose acetate.

The amount of active ingredient to be administered to the patient varies and is dependent on the patient's weight, age and medical history and on the type of administration, the indication and the severity of the illness. Conventionally 0.01 to 500 mg/kg, in particular 0.05 to 50 mg/kg, preferably 0.1 to 25 mg/kg of body weight of at least one compound according to the invention of the general structure of formula (I) or of a substructure of formula (I-A), (I-A-1) (I-B), or (I-B-1) derived from formula (I) are administered.

The following abbreviations are used in the descriptions of the experiments:
eq.=equivalent; calc.=calculated; BINAP=2,2'-bis(diphenylphosphino)-1,1'-binaphthyl; BOP=(benzotriazol-1-yloxy)tris(dimethylamino)phosphonium hexafluorophosphate; CDI=carbonyldiimidazole; dba=dibenzylideneacetone; DMAP=N,N-dimethylpyridin-4-amine; DME=1,2-dimethoxyethane; DMF=N,N-dimethylformamide; DMSO=dimethylsulfoxide; EDC1=1-ethyl-3-(3-dimethylaminopropyl)carbodiimid hydrochloride, f.=found; d=day; HATU=(1-[bis(dimethylamino)methylene]-1H-1,2,3-triazolo[4,5-b]pyridinium 3-oxid hexafluorophosphate); HOBt=hydroxybenzotriazole; h=hour; min=minute; MMPP=magnesium monoperoxyphthalate hexahydrate; NMP=N-methyl-2-pyrrolidone; R$_t$=retention time; TBTU=N,N,N',N'-tetramethyl-O-(benzotriazol-1-yl)uronium tetrafluoroborate; tBuXPhos=2-di-tert-butylphosphino-2,4,6-triisopropyl-1,1-biphenyl; tert=tertiary; THF=tetrahydrofuran; TOFMS=time-of-flight mass spectrometer; ES-MS=electrospray mass spectrometry (ES-MS); APCI=atmospheric pressure chemical ionization.

The following analytical HPLC/MS methods were used:
Method 1:
Column: Ascentis Express C18, 2.7 µm, 3 cm×2.1 mm; Column temperature: 30° C.; Injection volume: 1 µl; Dead time system: 0.2 min
Detection: MM-ES+APCI+DAD (254 nm)
Mobile phase A: water/0.1% formic acid
Mobile phase B: methanol/0.1% formic acid
Gradient:

| Time in min | % A | % B | Flow rate in ml/min |
| --- | --- | --- | --- |
| 1.0 | 95 | 5 | 0.8 |
| 4.0 | 0 | 100 | 0.8 |
| 5.0 | 0 | 100 | 0.8 |
| 6.0 | 95 | 5 | 0.8 |
| 6.5 | 95 | 5 | 0.8 |

Method 2:
Hardware: coupled Agilent 1290 Infinity UHPLC-TOF system; UV: 190-400 nm;
Column: Agilent Zorbax SB-C18, Rapid Resolution HD, 1.8 µm; Column temperature: 80° C.
Detection: time-of-flight mass spectrometer Agilent 6224; Ion source: dual ESI
Mobile phase A: water/0.1% formic acid
Mobile phase B: acetonitrile/0.1% formic acid
Gradient:

| Time in min | % A | % B | Flow rate in ml/min |
| --- | --- | --- | --- |
| 0.0 | 98 | 2 | 2.3 |
| 1.0 | 0 | 100 | 2.3 |
| 1.09 | 0 | 100 | 2.3 |
| 1.11 | 98 | 2 | 2.3 |
| 1.3 | 98 | 2 | 2.3 |

Method 3:
Column: XBridge C18 (150 mm×4.6 mm, 5.0 µm)
Column temperature: 35° C.
Flow rate: 1.0 mL/min
Injection volume: 3 µl
Detection: 215 and 254 nm
Mobile phase A: acetonitrile
Mobile phase B: 10 mM ammonium acetate in water
Gradient:

| Time in min | % A | % B | Flow rate in ml/min |
| --- | --- | --- | --- |
| 0 | 5 | 95 | 1.0 |
| 1.5 | 5 | 95 | 1.0 |
| 3 | 15 | 85 | 1.0 |
| 7 | 55 | 45 | 1.0 |
| 10 | 95 | 5 | 1.0 |
| 14 | 95 | 5 | 1.0 |
| 17 | 5 | 95 | 1.0 |
| 20 | 5 | 95 | 1.0 |

SYNTHESIS EXAMPLE NO. 1

2-(1-(2-(3-Fluoro-4-methoxyphenyl)-6,7-dihydro-5H-cyclopenta[d]-pyrimidin-4-yl)indolin-5-yl)acetic acid (Compound No. 1-01)

1a) 2-(3-Fluoro-4-methoxyphenyl)-6,7-dihydro-5H-cyclopenta[d]pyrimidin-4-amine Potassium t-butylate (160 mg, 1.43 mmol) was added to a solution of 3-fluoro-4-methoxybenzonitrile (1.0 g, 6.62 mmol) and adiponitrile (0.85 ml, 7.48 mmol) in mesitylene (5 ml) and the mixture was stirred at 130° C. for 1 h. The reaction mixture was then cooled and diluted with water (10 ml). The solid which had precipitated out was filtered off, washed with water (3×5 ml) and diethyl ether (3×5 ml) and dried. Beige-coloured solid. Yield: 1.29 g (75% of theory)
$^{13}$C-NMR (101 MHz, DMSO-d6, δ ppm): 21.4, 26.8, 33.6, 56.0, 113.16, 113.17, 113.3, 114.3, 114.5, 123.80, 123.84, 131.69, 131.76, 148.3, 148.4, 150.0, 152.4, 160.0, 160.57, 160.60, 171.2

1b) 2-(3-Fluoro-4-methoxyphenyl)-6,7-dihydro-3H-cyclopenta[d]pyrimidin-4(5H)-one Sodium nitrite (2.4 g, 34.79 mmol) was added to a solution of the product obtained in the preceding instructions 1a) (3.0 g, 11.57 mmol) in a mixture of water and acetic acid (15 ml of each) at room temperature and the mixture was then stirred at 90° C. for 30 min. The mixture was cooled and water (100 ml) was added. The solid which had precipitated out was filtered off, washed with water (3×5 ml) and diethyl ether (3×5 ml) and then dried. Beige-coloured solid. Yield: 2.17 g (72% of theory)
$^{13}$C-NMR (101 MHz, DMSO-d$_6$, δ ppm): 20.7, 27.0, 34.3, 56.2, 113.56, 113.57, 114.8, 115.0, 121.8, 124.54, 124.56, 125.0, 149.66, 149.76, 149.82, 152.2, 155.3, 160.9, 169.2

1c) 4-Chloro-2-(3-fluoro-4-methoxyphenyl)-6,7-dihydro-5H-cyclopenta[d]pyrimidine A suspension of the pyrimidine obtained according to instructions 1b) (1.0 g, 3.84 mmol) in phosphorus oxychloride (5 ml, 14.0 mmol) was stirred at 100° C. for 2 h. The cooled reaction solution was then poured on to ice (50 g) and extracted with methylene chloride (4×20 ml). The combined organic extracts were filtered over silica gel and concentrated. Beige-coloured solid. Yield: 815 mg (76% of theory)
$^{13}$C-NMR (101 MHz, CDCl$_3$, δ ppm): 21.4, 28.9, 34.8, 56.2, 112.74, 112.76, 115.9, 116.1, 124.68, 124.71, 129.92, 129.99, 131.0, 150.0, 150.1, 151.1, 153.5, 156.9, 163.02, 163.05, 176.6

1d) 2-(1-(2-(3-Fluoro-4-methoxyphenyl)-6,7-dihydro-5H-cyclopenta[d]pyrimidin-4-yl)indolin-5-yl)acetic acid methyl ester Caesium carbonate (391 mg, 1.27 mmol), BINAP (48 mg, 0.08 mmol) and palladium(II) acetate (18 mg, 0.08 mmol) were added to the chlorine compound from 1c) (388 mg, 1.39 mmol) and 2-(indolin-5-yl)acetic acid methyl ester (242 mg, 1.27 mmol) in anhydrous 1,4-dioxane (5 ml) under argon. The reaction mixture was stirred at 95° C. for 1 h and then purified by column chromatography [silica gel 60; cyclohexane/ethyl acetate 3:1]. Pale yellow solid. Yield: 146 mg (26% of theory)

LC-MS (method 1): R$_t$=3.7 min, m/z: [M+H]$^+$=434.2
$^{13}$C-NMR (101 MHz, CDCl$_3$, δ ppm): 22.2, 28.5, 31.1, 34.2, 40.7, 50.6, 52.0, 56.2, 110.0, 112.8, 115.5, 115.8, 116.0, 116.3, 124.5, 125.6, 127.8, 128.1, 132.1, 143.3, 149.5, 151.0, 153.5, 157.4, 172.3

1e) 2-(1-(2-(3-Fluoro-4-methoxyphenyl)-6,7-dihydro-5H-cyclopenta[d]pyrimidin-4-yl)indolin-5-yl)acetic acid 1 N sodium hydroxide solution (1.08 ml, 1.08 mmol) was added to a suspension of the methyl ester from 1d) (146 mg, 0.34 mmol) in methanol (5 ml) and 1,4-dioxane (5 ml) and the mixture was stirred at 95° C. (oil temperature) for 20 min 1 N hydrochloric acid (1.35 ml) was added and the mixture was concentrated on a rotary evaporator. The solid which thereby precipitated out was filtered off, washed with water (3×2 ml) and dried in vacuo. Colourless solid. Yield: 123 mg (86% of theory). Melting range: 195-200° C.

LC-MS (method 1): R$_t$=3.5 min, m/z: [M+H]$^+$=420.3
$^{13}$C-NMR (101 MHz, DMSO-d$_6$, δ ppm): 21.5, 27.9, 30.2, 33.9, 40.2, 49.9, 56.0, 113.5, 114.4, 114.6, 115.3, 115.4, 124.0, 125.7, 127.5, 128.4, 131.2, 131.3, 132.0, 142.7, 148.7, 148.8, 150.0, 152.5, 156.9, 159.7, 159.8, 172.9, 174.4

SYNTHESIS EXAMPLE NO. 2

2-(1-(2-(4-Methoxyphenyl)-6,7-dihydro-5H-cyclopenta[d]pyrimidin-4-yl)indolin-5-yl)acetic acid (Compound No. 1-03)

2a) 2-(4-Methoxyphenyl)-6,7-dihydro-5H-cyclopenta[d]pyrimidin-4-amine

Synthesis analogous to instructions 1a) from 4-methoxybenzonitrile (5.00 g, 37.60 mmol) and adiponitrile (4.82 ml, 4.59 g, 42.40 mmol). The target compound was obtained as a beige solid. Yield: 5.68 g (63% of theory)

LC-MS (method 1): R$_t$=2.5 min, m/z: [M+H]$^+$=242.3
$^{13}$C-NMR (101 MHz, CDCl$_3$, δ ppm): 21.0, 26.8, 33.7, 55.1, 112.8, 113.3, 128.9, 131.1, 159.9, 160.5, 161.7, 171.1

2b) 2-(4-Methoxyphenyl)-6,7-dihydro-3H-cyclopenta[d]pyrimidin-4(5H)-one

The target compound was prepared analogously to instructions 1b) from 2-(4-methoxyphenyl)-6,7-dihydro-5H-cyclopenta[d]pyrimidin-4-amine (5.65 g, 23.41 mmol). Yellow solid. Yield: 3.21 g (57% of theory)

LC-MS (method 1): R$_t$=3.15 min, m/z: [M+H]$^+$=243.2
$^{13}$C-NMR (101 MHz, DMSO-d6, δ ppm): 20.7, 27.0, 34.4, 55.4, 113.9, 121.3, 124.6, 129.3, 156.2, 160.9, 161.7, 169.2

2c) 4-Chloro-2-(4-methoxyphenyl)-6,7-dihydro-5H-cyclopenta[d]pyrimidine

The pyrimidone from 2b) (3.21 g, 13.25 mmol) and phosphorus oxychloride (17 ml, 28.36 g, 188.0 mmol) were stirred at 100° C. (oil bath temperature) for 2 h. Ice-water (300 ml) was added in portions to the reaction mixture, while cooling, and the mixture was stirred for 20 min. It was extracted with methylene chloride and the combined organic phases were dried with magnesium sulfate, filtered and concentrated by evaporation in vacuo. Brown solid. Yield: 3.07 g (89% of theory)
LC-MS (method 1): $R_t$=4.05 min, m/z: [M+H]$^+$=261.2
$^{13}$C-NMR (101 MHz, CDCl$_3$, δ ppm): 21.4, 28.8, 34.6, 55.4, 113.9, 128.4, 130.2, 130.8, 157.5, 162.3, 163.4, 175.8

2d) 2-(1-(2-(4-Methoxyphenyl)-6,7-dihydro-5H-cyclopenta[d]pyrimidin-4-yl)indolin-5-yl)acetic acid methyl ester The target compound was prepared analogously to instructions 1d) from 4-chloro-2-(4-methoxyphenyl)-6,7-dihydro-5H-cyclopenta[d]pyrimidine (203 mg, 0.78 mmol) and 2-(indolin-5-yl)acetic acid methyl ester (150 mg, 0.78 mmol). Beige solid. Yield: 275 mg (85% of theory)
LC-MS (method 1): $R_t$=3.5 min, m/z: [M+H]$^+$=416.3
$^{13}$C-NMR (101 MHz, CDCl$_3$, δ ppm): 22.1, 28.5, 31.0, 34.4, 40.7, 50.5, 52.0, 55.3, 113.7, 114.9, 116.2, 125.4, 127.3, 128.0, 129.7, 130.9, 131.9, 143.6, 157.4, 161.3, 162.0, 172.4, 174.6

2e) 2-(1-(2-(4-Methoxyphenyl)-6,7-dihydro-5H-cyclopenta[d]pyrimidin-4-yl)indolin-5-yl)acetic acid Preparation from the methyl ester obtained under 2d) (253 mg, 0.61 mmol) by means of saponification analogously to instructions 1e). Colourless solid. Yield: 223 mg (91% of theory); Melting range: 220-222° C.
LC-MS (method 1): $R_t$=3.3 min, m/z: [M+H]$^+$=402.3
$^{13}$C-NMR (101 MHz, DMSO-d6, δ ppm): 21.5, 27.9, 30.2, 33.9, 40.1, 49.8, 55.2, 113.6, 114.7, 115.4, 125.6, 127.6, 128.2, 129.0, 130.6, 131.9, 142.9, 156.9, 160.8, 160.9, 172.9, 174.3

SYNTHESIS EXAMPLE NO. 3

2-(1-(2-(5-Chlorothiophen-2-yl)-6,7-dihydro-5H-cyclopenta[d]-pyrimidin-4-yl)indolin-5-yl)acetic acid (Compound No. 1-13)

3a) 2-(1-(2-(5-Chlorothiophen-2-yl)-6,7-dihydro-5H-cyclopenta[d]pyrimidin-4-yl)indolin-5-yl)acetic acid methyl ester Preparation analogously to instructions 1d) from 2-(indolin-5-yl)acetic acid methyl ester (95.6 mg, 0.5 mmol) and 4-chloro-2-(5-chlorothiophen-2-yl)-6,7-dihydro-5H-cyclopenta[d]pyrimidine (135.6 mg, 0.5 mmol). Yellow solid. Yield: 89 mg (41% of theory)
$^{13}$C-NMR (101 MHz, CDCl$_3$, δ ppm): 22.1, 28.5, 29.8, 31.2, 34.1, 40.7, 50.4, 52.0, 109.5, 115.3, 116.8, 125.1, 125.5, 125.6, 127.4, 128.1, 128.1, 130.3, 143.1, 157.1, 172.3

3b) 2-(1-(2-(5-Chlorothiophen-2-yl)-6,7-dihydro-5H-cyclopenta[d]pyrimidin-4-yl)indolin-5-yl)acetic acid 1 N sodium hydroxide solution (0.23 ml) was added to the ester from 3a) (83.6 mg, 0.2 mmol) in methanol (2 ml) and the mixture was stirred at 70° C. for 4 h. 1 N hydrochloric acid (0.23 ml) was added to the reaction mixture. The solid which had precipitated out was filtered off, washed with water and methanol and dried. Pale brown solid. Yield: 63 mg (78% of theory); Melting range: 185-191° C.
$^{13}$C-NMR (101 MHz, DMSO-d6, δ ppm): 21.4, 27.8, 30.4, 33.7, 40.2, 49.7, 115.6, 115.9, 125.6, 127.0, 127.7, 128.2, 128.8, 130.9, 132.0, 142.5, 142.7, 156.6, 156.7, 172.9, 174.2

SYNTHESIS EXAMPLE NO. 4

2-(1-(2-(5-Fluorothiophen-2-yl)-6,7-dihydro-5H-cyclopenta[d]pyrimidin-4-yl)indolin-5-yl)acetic acid (Compound No. 1-15)

4a) 2-(5-Fluorothiophen-2-yl)-6,7-dihydro-5H-cyclopenta[d]pyrimidin-4-ol

Potassium tert-butylate (1.34 g, 12 mmol) was added to a solution of 5-fluorothiophene-2-carbonitrile (1.52 g, 12 mmol) and ethyl 2-aminocyclopent-1-enecarboxylate (1.55 g, 10 mmol) in mesitylene (50 ml) and the mixture was stirred at 150° C. for 4 h. 1 N hydrochloric acid (12 ml) was then added and the solid which had precipitated out was filtered off, washed with ethyl acetate and dried. Beige-coloured solid. Yield: 1.3 g (55% of theory)
LC-MS (method 1): $R_t$=3.42 min, m/z: [M+H]$^+$=237.2
$^1$H-NMR (400 MHz, DMSO-d6, δ ppm): 1.97 (m, 2H), 2.64 (m, 2H), 2.76 (m, 2H), 6.86 (dd, J=2.0, 4.3, 1H), 7.88 (s, 1H), 12.67 (s, 1H)

4b) 4-Chloro-2-(5-fluorothiophen-2-yl)-6,7-dihydro-5H-cyclopenta[d]pyrimidine A suspension of the pyrimidinone obtained under 4a) (1.3 g, 5.5 mmol) and phosphorus oxychloride (5 ml) was stirred at 95° C. (oil temperature) for 2 h. The mixture was then poured on to ice-water (50 ml) (exothermic) and the resulting emulsion was saturated with sodium chloride and extracted with methylene chloride. The combined organic phases were dried with magnesium sulfate, filtered over silica gel and concentrated in vacuo. Yellow solid. Yield: 928 mg (66% of theory)
LC-MS (method 1): $R_t$=4.09 min, m/z: [M]$^+$=255.1
$^1$H-NMR (400 MHz, CDCl$_3$, δ ppm): 2.16 (m, 2H), 2.96 (m, 2H), 3.04 (m, 2H), 6.50 (dd, J=1.7, 4.2, 1H), 7.64 (dd (t-like), J=4.1, 1H)
$^{13}$C-NMR (101 MHz, CDCl$_3$, δ ppm): 21.3, 28.8, 34.6, 109.1 (d, $J_{C,F}$=11), 126.2 (d, $J_{C,F}$=3.9), 130.3 (d, $J_{C,F}$=3.6), 130.8 (d, $J_{C,F}$=1.1), 156.6, 160.1 (d, $J_{C,F}$=1.4), 168.5 (d, $J_{C,F}$=294), 176.5

4c) 2-(1-(2-(5-Fluorothiophen-2-yl)-6,7-dihydro-5H-cyclopenta[d]pyrimidin-4-yl)indolin-5-yl)acetic acid methyl ester Reaction of 2-(indolin-5-yl)acetic acid methyl ester (191 mg, 1 mmol) and 4-chloro-2-(5-fluorothiophen-2-yl)-6,7-dihydro-5H-cyclopenta[d]pyrimidine (255 mg, 1 mmol) analogously to instructions 1d). Water was added to the reaction mixture and the mixture was extracted with ethyl acetate. The combined organic phases were dried with magnesium sulfate and concentrated. The residue was purified by column chromatography [silica gel 60; cyclohexane/ethyl acetate 2:1]. Colourless solid. Yield: 316 mg (77% of theory)
LC-MS (method 1): $R_t$=4.07 min, m/z: [M+H]$^+$=410.1
$^1$H-NMR (400 MHz, CDCl$_3$, δ ppm): 2.08 (m, 2H), 2.94 (m, 2H), 3.12-3.20 (4H), 3.60 (s, 2H), 3.70 (s, 3H), 4.31 (m, 2H), 6.50 (dd, J=1.7, 4.1, 1H), 7.14-7.17 (2H), 7.58 (s (broad), 1H), 8.14 (d, J=8.2, 1H)
$^{13}$C-NMR (101 MHz, CDCl$_3$, δ ppm): 22.1, 28.5, 31.1, 34.3, 40.7, 50.4, 52.0, 108.6 (d, $J_{C,F}$=10.6), 115.0, 116.6, 124.4, 125.4, 127.7, 128.0, 131.9, 132.4, 143.3, 157.1, 166.0 (d, $J_{C,F}$=295), 172.3, 174.1

4d) 2-(1-(2-(5-Fluorothiophen-2-yl)-6,7-dihydro-5H-cyclopenta[d]pyrimidin-4-yl)indolin-5-yl)acetic acid 1 N sodium hydroxide solution (1 ml) was added to the ester from 4c) (306 mg, 0.75 mmol) in methanol (3 ml) and the mixture was stirred at 60° C. for 2 h. 2 N hydrochloric acid (0.5 ml) was added and the solid which had precipitated out was filtered off, washed with water and dried. Colourless solid. Yield: 246 mg (83% of theory)

LC-MS (method 1): $R_t$=3.84 min, m/z: [M+H]$^+$=396.2

$^1$H-NMR (400 MHz, DMSO-d6, δ ppm): 2.00 (m, 2H), 2.83 (m, 2H), 3.12-3.20 (4H), 3.51 (s, 2H), 4.35 (m, 2H), 6.80 (dd, J=2.0, 4.2, 1H), 7.09-7.13 (2H), 7.53 (d (t-like), J=4.1, 1H), 8.11 (d, J=8.2, 1H)

$^{13}$C-NMR (101 MHz, DMSO-d6, δ ppm): 21.4, 27.8, 30.3, 33.6, 40.1, 49.7, 109.6 (d, $J_{C,F}$=11.1), 115.3, 115.9, 124.3 (d, $J_{C,F}$=4.3), 125.6, 127.6, 128.6, 132.0, 132.4 (d, $J_{C,F}$=2.4), 142.5, 156.6, 156.9, 166.0 (d, $J_{C,F}$=290), 172.8, 174.1

SYNTHESIS EXAMPLE NO. 5

2-(1-(2-(3-Chloro-4-methoxyphenyl)-6,7-dihydro-5H-cyclopenta[d]-pyrimidin-4-yl)indolin-5-yl)acetic acid (Compound No. 1-02)

5a) 2-(3-Chloro-4-methoxyphenyl)-6,7-dihydro-3H-cyclopenta[d]pyrimidin-4(5H)-one Methyl 2-oxocyclopentanecarboxylate (2.37 g, 16.69 mmol), 3-chloro-4-methoxybenzimidamide hydrochloride (1.82 g, 8.22 mmol) and caesium carbonate (3.21 g, 9.86 mmol) were suspended in DMF and the suspension was stirred at 150° C. (oil bath temperature) for 2 h. The DMF was then distilled off and the residue was purified by chromatography [silica gel 60; diethyl ether, then THF/methanol 10:1]. Beige solid. Yield: 438 mg (19% of theory)

LC-MS (method 1): $R_t$=3.45 min, m/z: [M+H]$^+$=277.2

$^{13}$C-NMR (101 MHz, DMSO-d6, δ ppm): 20.7, 27.0, 34.2, 56.4, 112.6, 121.3, 127.9, 129.0, 156.8, 160.8. The signals are broad in some cases. Only clear signals are stated.

5b) 4-Chloro-2-(3-chloro-4-methoxyphenyl)-6,7-dihydro-5H-cyclopenta[d]pyrimidine The pyrimidine from 5a) (419 mg, 1.51 mmol) was suspended in phosphorus oxychloride (4 ml) and the suspension was stirred at room temperature for 16 h. The reaction mixture was then poured on to ice-water (30 ml) and extracted with methylene chloride (3×10 ml). The combined organic phases were dried with magnesium sulfate, filtered and evaporated in vacuo. Beige solid. Yield: 365 mg (82% of theory)

LC-MS (method 1): $R_t$=4.2 min, m/z: [M+H]$^+$=295.1

$^{13}$C-NMR (101 MHz, CDCl$_3$, δ ppm): 21.4, 28.9, 34.8, 56.2, 111.5, 122.8, 128.1, 130.1, 130.2, 131.1, 157.0, 157.1, 162.8, 176.6

5c) 2-(1-(2-(3-Chloro-4-methoxyphenyl)-6,7-dihydro-5H-cyclopenta[d]pyrimidin-4-yl)indolin-5-yl)acetic acid methyl ester Preparation analogously to instructions 1d) from the chlorine compound from 5b) (350 mg, 1.20 mmol) and 2-(indolin-5-yl)acetic acid methyl ester (230 mg, 1.20 mmol). Beige solid. Yield: 205 mg (38% of theory)

LC-MS (method 1): $R_t$=3.9 min, m/z: [M+H]$^+$=450.2

$^{13}$C-NMR (101 MHz, DMSO-d6, δ ppm): 21.5, 27.8, 30.2, 33.9, 39.7, 49.9, 51.6, 56.2, 112.6, 115.4, 115.5, 121.0, 125.6, 127.5, 127.5, 128.8, 131.5, 132.1, 142.9, 155.9, 156.9, 159.6, 171.8, 174.5

5d) 2-(1-(2-(3-Chloro-4-methoxyphenyl)-6,7-dihydro-5H-cyclopenta[d]pyrimidin-4-yl)indolin-5-yl)acetic acid The methyl ester from 5c) (190 mg, 0.42 mmol) was reacted analogously to instructions 1e). Beige solid. Yield: 163 mg (89% of theory) Melting point: 127° C.

LC-MS (method 1): $R_t$=3.7 min, m/z: [M+H]$^+$=436.2

$^{13}$C-NMR (101 MHz, DMSO-d6, δ ppm): 21.4, 27.9, 30.3, 33.7, 40.2, 49.9, 56.3, 112.6, 115.4, 115.6, 121.0, 125.7, 127.4, 127.6, 128.6, 128.8, 131.1, 132.1, 142.6, 156.0, 156.9, 159.3, 172.9, 173.9

SYNTHESIS EXAMPLE NO. 6

2-(1-(2-(3-Chloro-4-methoxyphenyl)-6,7-dihydro-5H-cyclopenta[d]-pyrimidin-4-yl)-1H-indazol-5-yl)acetic acid (Compound No. 1-59)

6a) 5-Iodo-1H-indazole

Sodium nitrite (2.7 g, 39.1 mmol) in water (40 ml) was added dropwise to a solution of 1-H-indazol-5-amine (5.2 g, 39.1 mmol) in 6 N hydrochloric acid (73.7 ml) at 0° C. The mixture obtained was in turn added dropwise to a solution of potassium iodide (26.9 g, 162 mmol) in water (60 ml) at 0° C. and the mixture was stirred at room temperature for 3 h. The reaction mixture was then extracted with ethyl acetate (4×30 ml) and the combined organic phases were washed with washed with 10% w/v sodium thiosulfate solution (4×30 ml) and brine (2×30 ml), dried over magnesium sulfate and concentrated. Brown solid. Yield: 8.64 g (90% of theory)

$^{13}$C-NMR (101 MHz, CDCl$_3$, δ ppm): 84.4, 111.7, 125.6, 129.9, 133.4, 135.4, 139.0

6b) 5-Iodo-1-(4-methoxybenzyl)-1H-indazole

4-Methoxybenzyl chloride (4.03 ml, 4.65 g, 29.68 mmol) was added to a solution of 5-iodo-1H-indazole (5.54 g, 24.73 mmol), sodium iodide (741 mg, 4.95 mmol) and caesium carbonate (9.67 g, 29.68 mmol) in DMF (25 ml) and the mixture was then stirred at room temperature for 16 h. Ethyl acetate (30 ml) and water (30 ml) were added to the suspension. The organic phase was separated off and washed with water (2×15 ml) and brine (2×15 ml), dried over magnesium sulfate, filtered and concentrated by evaporation in vacuo. The residue was purified by column chromatography [silica gel 60; cyclohexane/ethyl acetate 9:1]. 2.82 g (31% of theory) of the desired amine as a colourless solid and 2.16 g (24% of theory) of the regioisomer were isolated.

LC-MS (method 1): $R_t$=3.95 min, m/z: [M+H]$^+$=365.1. Regioisomer: LC-MS (method 1): $R_t$=3.85 min, m/z: [M+H]$^+$=365.1.

$^{13}$C-NMR (101 MHz, CDCl$_3$, δ ppm): 52.8, 55.2, 83.9, 111.2, 114.2, 126.9, 128.4, 128.6, 130.0, 132.1, 134.6, 138.4, 159.3. Regioisomer: $^{13}$C-NMR (101 MHz, CDCl$_3$, δ ppm): 55.3, 57.1, 85.8, 114.4, 119.3, 121.6, 124.3, 127.2, 129.1, 129.7, 134.5, 147.2, 159.8

6c) 2-(1-(4-Methoxybenzyl)-1H-indazol-5-yl)acetic acid ethyl ester

Chloroacetic acid ethyl ester (7.77 g, 6.79 ml, 63.40 mmol) and trifluoroacetic acid (341 mg, 230 μl, 2.99 mmol) were added to a suspension of the iodine compound obtained under 6b) (2.31 g, 6.34 mmol), manganese (3.48 g, 63.40 mmol), nickel(II) bromide (275 mg, 1.26 mmol) and 2,2-bipyridyl (197 mg, 1.26 mmol) in DMF (23 ml) and the mixture was heated briefly with a heat gun until the reaction started (HIGHLY exothermic!). The mixture was then stirred at 60° C. (oil bath temperature) for 1 h, and thereafter ethyl acetate (30 ml) and 1 N hydrochloric acid (20 ml) were added. The manganese residues were filtered off and the aqueous phase was separated off and extracted with ethyl acetate (2×15 ml). The combined organic phases were dried with magnesium sulfate, filtered and concentrated by evaporation in vacuo. The residue was purified by column chromatography [silica gel 60; cyclohexane/ethyl acetate 4:1]. Yellow solid. Yield: 1.36 g (66% of theory)

LC-MS (method 1): $R_t$=3.7 min, m/z: $[M+H]^+$=325.3

$^{13}$C-NMR (101 MHz, CDCl$_3$, δ ppm): 14.1, 41.1, 52.6, 55.2, 60.8, 109.4, 114.1, 121.3, 124.6, 126.5, 128.0, 128.6, 128.8, 132.9, 138.7, 159.2, 171.8

6d) 2-(1H-Indazol-5-yl)acetic acid ethyl ester

A solution of the product from 6c) (1.40 g, 4.32 mmol) in trifluoromethanesulfonic acid (10.0 g, 66.63 mmol) was stirred at room temperature overnight. The mixture was then diluted with methylene chloride (100 ml) and washed with water and saturated sodium carbonate solution (50 ml of each). The organic phase was dried with sodium sulfate and concentrated to dryness in vacuo. The residue was finally purified by column chromatography [silica gel 60; cyclohexane/diethyl ether 2:1→1:2]. Beige-coloured solid. Yield: 542 mg (61% of theory)

$^{13}$C-NMR (101 MHz, CDCl$_3$, δ ppm): 14.2, 41.2, 60.9, 110.0, 121.1, 123.3, 127.0, 128.7, 134.2, 139.3, 172.0

6e) Ethyl 2-(1-(2-(3-chloro-4-methoxyphenyl)-6,7-dihydro-5H-cyclopenta[d]pyrimidin-4-yl)-1H-indazol-5-yl)acetate 4-Chloro-2-(3-chloro-4-methoxyphenyl)-6,7-dihydro-5H-cyclopenta[d]pyrimidine (286 mg, 0.97 mmol), the product of 6d) (197 mg, 0.97 mmol), caesium carbonate (632 mg, 1.94 mmol), BINAP (36 mg, 0.06 mmol) and palladium(II) acetate (11 mg, 0.05 mmol) in dry DMF (3 ml) were stirred under an argon atmosphere for 1 h at 120° C. (oil bath temperature). Ethyl acetate (10 ml) and water (15 ml) were added to the mixture and the organic phase was separated, washed with water (2×5 ml) and dried over magnesium sulfate and evaporated. The residue was purified by column chromatography [silica gel 60; cyclohexane/ethyl acetate 4:1]. Colorless solid. Yield: 110 mg (24% of theory)

LC-MS (method 1): $R_t$=4.5 min, m/z: $[M+H]^+$=463.3

$^{13}$C-NMR (101 MHz, CDCl3, δ ppm): 14.2, 22.1, 31.8, 34.8, 41.2, 56.3, 56.3, 61.0, 111.7, 115.8, 120.4, 121.1, 122.7, 126.2, 127.9, 129.3, 129.7, 130.2, 131.6, 137.8, 138.8, 155.6, 156.8, 161.6, 171.6, 178.0

6f) 2-(1-(2-(3-Chloro-4-methoxyphenyl)-6,7-dihydro-5H-cyclopenta[d]pyrimidin-4-yl)-1H-indazol-5-yl)acetic acid Produced from the product of 6e) (102 mg, 0.22 mmol) in an analogous manner to procedure 1e). Colorless solid. Yield: 96 mg (quantitative)

LC-MS (Method 1): $R_t$=4.3 min, m/z: $[M+H]^+$=435.2

$^{13}$C-NMR (101 MHz, DMSO-d6, δ ppm): 21.3, 31.4, 34.0, 56.3, 56.3, 66.3, 112.7, 114.7, 119.7, 121.3, 121.5, 125.7, 127.8, 128.8, 130.1, 130.4, 130.4, 137.7, 138.5, 154.8, 156.3, 160.3, 172.8, 177.7

SYNTHESIS EXAMPLE NO. 7

1-(2-(5-Chlorothiophen-2-yl)-6,7-dihydro-5H-cyclopenta[d]pyrimidin-4-yl)-2-oxoindoline-5-carboxylic acid (Compound No. 1-69)

7a) 3-(Carboxymethyl)-4-(2-(5-chlorothiophen-2-yl)-6,7-dihydro-5H-cyclopenta[d]pyrimidin-4-ylamino)benzoic acid Methyl 2-oxoindoline-5-carboxylate (1.14 g, 5.96 mmol) was stirred in 5 N sodium hydroxide solution (5.96 ml, 29.81 mmol) at 100° C. for 4 h. A yellow suspension was formed. After cooling, dry ice was added, and the mixture was stirred for 30 min and concentrated in vacuo. The resulting pale yellow solid (2.92 g) comprising the di-sodium salt and sodium bicarbonate was further reacted directly. For this, 4-chloro-2-(5-chlorothiophen-2-yl)-6,7-dihydro-5H-cyclopenta[d]pyrimidine (694 mg, 2.56 mmol), BINAP (112 mg, 0.18 mmol), palladium(II) acetate (40 mg, 0.18 mmol) and caesium carbonate (1.67 g, 5.12 mmol) were added to the di-sodium salt (1.61 g) in anhydrous DMSO (4 ml) and the mixture was stirred at 130° C. (oil bath temperature) for 5 h. 1 N sodium hydroxide solution (45 ml) and diethyl ether (20 ml) were then added to the reaction mixture. The aqueous phase was separated off, washed with diethyl ether (3×5 ml) and ethyl acetate (2×5 ml) and acidified (pH 4) with 1 N hydrochloric acid, after which a solid precipitated out. The mixture was extracted with THF (4×10 ml) and the combined organic phases were dried over magnesium sulfate, filtered and concentrated by evaporation in vacuo. The residue was purified by means of column chromatography [silica gel 60; ethyl acetate/methanol 1:0, 5:1, 0:1, in each case with 0.5% acetic acid]. Yellow solid. Yield: 447 mg (41% of theory). Melting point above 260° C.

LC-MS (method 1): $R_t$=3.8 min, m/z: $[M+H]^+$=430.2.

$^{13}$C-NMR (101 MHz, DMSO-d6, δ ppm): 21.1, 21.3, 27.1, 33.6, 43.5, 116.8, 118.7, 121.1, 126.7, 127.6, 128.1, 128.4, 130.7, 131.8, 143.1, 156.0, 157.3, 157.7, 158.0, 172.0. NMR signals greatly broadened. Only signals which were clearly to be identified are stated.

7b) 1-(2-(5-Chlorothiophen-2-yl)-6,7-dihydro-5H-cyclopenta[d]pyrimidin-4-yl)-2-oxoindoline-5-carboxylic acid Hünig's base (0.95 ml, 5.59 mmol) and trifluoroacetic anhydride (0.80 ml, 5.67 mmol) were added to a suspension of the acid from 7a) (400 mg, 0.93 mmol) in dioxane (20 ml). After stirring at room temperature for 30 min, water (80 ml) was added to the clear solution formed. The resulting precipitate was filtered off, washed with water (3×5 ml) and dried. The crude product was purified by column chromatography [silica gel 60; ethyl acetate/acetic acid 200:1]. Beige-coloured solid. Yield: 114 mg (30% of theory)

$^{13}$C-NMR (101 MHz, DMSO-d6, δ ppm): 21.9, 29.0, 34.0, 35.3, 111.1, 125.6, 125.7, 125.7, 128.0, 128.3, 128.6, 129.5, 132.3, 141.0, 145.8, 150.9, 158.0, 167.0, 173.1, 179.6

SYNTHESIS EXAMPLE NO. 8

1-(2-(5-Chlorothiophen-2-yl)-6,7-dihydro-5H-cyclopenta[d]pyrimidin-4-yl)-1H-indazole-5-carboxylic acid (Compound No. 1-73)

Caesium carbonate (652 mg, 2 mmol), BINAP (44 mg, 0.07 mmol) and palladium(II) acetate (16 mg, 0.07 mmol) were added to 4-chloro-2-(5-chlorothiophen-2-yl)-6,7-dihydro-5H-cyclopenta[d]pyrimidine (271 mg, 1 mmol) and 1H-indazole-5-carboxylic acid (162 mg, 1 mmol) in dry DMF (2 ml) under argon and the mixture was stirred at 140° C. for 1 h. Water, saturated sodium chloride solution and ethyl acetate were added to the reaction mixture, whereby a solid precipitated out, which was filtered off and washed with water (2×5 ml). The solid was dissolved in a mixture of DMSO, water and methanol (1:1:1, 600 ml) under heating, and then precipitated out by concentration in vacuo. Pale grey solid. Yield: 40 mg (10% of theory)

LC-MS (method 1): $R_t$=4.5 min, m/z: $[M+H]^+$=397.2

SYNTHESIS EXAMPLE NO. 9

1-(2-(5-Chlorothiophen-2-yl)-6,7-dihydro-5H-cyclopenta[d]pyrimidin-4-yl)-1H-indole-5-carboxylic acid (Compound No. 1-70)

9a) Methyl 1-(2-(5-chlorothiophen-2-yl)-6,7-dihydro-5H-cyclopenta[d]pyrimidin-4-yl)-1H-indole-5-carboxylic acid Methyl 1H-indole-5-carboxylic acid (310 mg, 1.77 mmol), copper(I) iodide (55 mg, 0.29 mmol) and caesium carbonate (720 mg, 2.21 mmol) were added to 4-chloro-2-(5-chlorothiophen-2-yl)-6,7-dihydro-5H-cyclopenta[d]pyrimidine (400 mg, 1.48 mmol) in DMF (2 ml) and the mixture was stirred at 150° C. for 40 min. The solvent was then distilled off in vacuo and the residue was purified by column chromatography [silica gel 60; methylene chloride]. Beige-coloured solid. Yield: 482 mg (80% of theory)

$^{13}$C-NMR (101 MHz, DMSO-d6, δ ppm): 22.8, 30.8, 34.6, 52.0, 107.6, 115.0, 120.2, 123.5, 124.2, 124.9, 126.7, 127.6, 128.1, 129.6, 134.3, 138.3, 141.4, 154.5, 159.0, 167.6, 178.5

9b) 1-(2-(5-Chlorothiophen-2-yl)-6,7-dihydro-5H-cyclopenta[d]pyrimidin-4-yl)-1H-indole-5-carboxylic acid 0.5 N lithium hydroxide solution (5.0 ml, 2.5 mmol) was added to the ester from 9a) (480 mg, 1.17 mmol) in methanol (5 ml) and THF (25 ml) and the mixture was stirred at 70° C. for 2 h. For working up, the mixture was neutralized with 1 N hydrochloric acid (2.5 ml, 2.5 mmol) and concentrated to approx. 5 ml. The solid which had precipitated out was filtered off, washed with water and recrystallized in dioxane. White solid. Yield: 298 mg (64% of theory). Melting point above 265° C.

$^{13}$C-NMR (101 MHz, DMSO-d6, δ ppm): 22.1, 29.7, 34.0, 107.2, 114.4, 121.5, 123.0, 124.4, 124.7, 127.9, 128.3, 128.6, 129.3, 132.2, 137.4, 141.2, 153.8, 157.6, 167.7, 178.6

SYNTHESIS EXAMPLE NO. 10

1-(2-(5-Chlorothiophen-2-yl)-6,7-dihydro-5H-cyclopenta[d]pyrimidin-4-yl)indoline-5-carboxylic acid (Compound No. 1-72)

10a) Methyl 1-(2-(5-chlorothiophen-2-yl)-6,7-dihydro-5H-cyclopenta[d]pyrimidin-4-yl)indoline-5-carboxylate The target compound was prepared analogously to instructions 1 d) from 4-chloro-2-(5-chlorothiophen-2-yl)-6,7-dihydro-5H-cyclopenta[d]pyrimidine (400 mg, 1.48 mmol) and methyl indoline-5-carboxylate (314 mg, 1.77 mmol). Yellow solid. Yield: 207 mg (34% of theory)

LC-MS (method 1): $R_t$=4.4 min, m/z: $[M+H]^+$=412.2

10b) 1-(2-(5-Chlorothiophen-2-yl)-6,7-dihydro-5H-cyclopenta[d]pyrimidin-4-yl)indoline-5-carboxylic acid 0.5 M lithium hydroxide solution (2 ml, 1.00 mmol) was added to the ester from 10a) (207 mg, 0.50 mmol) in THF (8 ml) and the mixture was stirred at 50° C. for 1 d. The solution was filtered over Celite®, 0.5 N hydrochloric acid (2 ml) was added and the mixture was concentrated to 4 ml in vacuo. The solid which had precipitated out was filtered off, washed with water and methanol and dried in vacuo. Yellow solid. Yield: 177 mg (89% of theory). Melting point above 260° C.

LC-MS (method 1): $R_t$=4.1 min, m/z: $[M+H]^+$=391.2

$^{13}$C-NMR (101 MHz, THF-d8, δ ppm): 22.7, 28.4, 31.6, 34.8, 51.5, 116.0, 117.0, 125.0, 126.6, 127.7, 128.1, 130.3, 132.5, 132.9, 144.1, 149.0, 157.8, 158.5, 167.2, 176.3

SYNTHESIS EXAMPLE NO. 11

2-(1-(2-(5-Chlorothiophen-2-yl)-6,7-dihydro-5H-cyclopenta[d]-pyrimidin-4-yl)-2-oxoindolin-5-yl)acetic acid (Compound No. 1-64)

11a) 2-Oxo-2-(2-oxoindolin-5-yl)acetic acid methyl ester

Indolin-2-one (2.95 g, 22.15 mmol) was added to a yellow solution of aluminium chloride (14.77 g, 110.75 mmol) and methyl 2-chloro-2-oxoacetate (3.06 ml, 4.07 g, 33.22 mmol) in 1,2-dichloroethane (38 ml) under argon and while cooling with a water bath. The reaction mixture was stirred at room temperature for 30 min, cooled and poured on to ice-water (500 ml) (evolution of gas). The solid which had precipitated out was filtered off, washed with water (3×10 ml) and dried in vacuo. Beige solid. Yield: 3.86 g (79% of theory)

LC-MS (method 1): $R_t$=2.5 min, m/z: $[M+H]^+$=220.2

$^{13}$C-NMR (101 MHz, DMSO, δ ppm): 35.3, 52.8, 109.4, 125.0, 125.5, 126.9, 131.6, 150.7, 164.8, 176.7, 185.4

11b) 2-(2-Oxoindolin-5-yl)acetic acid methyl ester

Palladium on charcoal (10%, 4.05 g) was added to a suspension of 2-oxo-2-(2-oxoindolin-5-yl)acetic acid methyl ester (8.97 g, 40.55 mmol) and trifluoroacetic acid (10 ml, 14.80 g) under argon. The suspension was then hydrogenated at 50° C. and a hydrogen pressure of 6 bar for 4 h. The palladium was filtered off and the mother liquor was evaporated to dryness in vacuo. Colourless solid. Yield: 5.76 g (69% of theory)

LC-MS (method 1): $R_t$=2.55 min, m/z: [M+H]$^+$=206.2

$^{13}$C-NMR (101 MHz, DMSO-d6, δ ppm): 35.7, 39.7, 51.6, 108.8, 125.3, 125.9, 127.0, 128.3, 142.5, 171.9, 176.3

11c) 2,2'-(4-Amino-1,3-phenylene)diacetic acid di-sodium salt

The methyl ester from instructions 11b) (2.50 g, 12.18 mmol) was stirred in 5 N aqueous sodium hydroxide solution (12.18 ml, 60.91 mmol) at 100° C. for 4 h. The orange-coloured solution was cooled, dry ice was added and the mixture was stirred for 30 min. The residue was concentrated by evaporation in vacuo. 6.15 g of a yellow solid, which comprises the di-sodium salt of the target compound and sodium bicarbonate, were obtained.

LC-MS (method 1): $R_t$=0.35 min, m/z: [M+H]$^+$=210.2

$^{13}$C-NMR (101 MHz, DMSO-d6, δ ppm): 44.0, 44.9, 114.3, 123.7, 126.5, 127.2, 131.0, 144.6, 175.2, 175.8

11d) 2,2'-(4-(2-(5-Chlorothiophen-2-yl)-6,7-dihydro-5H-cyclopenta[d]pyrimidin-4-ylamino)-1,3-phenylene)diacetic acid 4-Chloro-2-(5-chlorothiophen-2-yl)-6,7-dihydro-5H-cyclopenta[d]pyrimidine (437 mg, 1.61 mmol), the amine from 11c) (1.22 g), BINAP (70 mg, 0.11 mmol), palladium(II) acetate (25 mg, 0.11 mmol) and caesium carbonate (1.05 g, 3.22 mmol) in anhydrous DMSO (4.5 ml) were stirred at 130° C. (oil bath temperature) under argon for 1.5 h. 1 N sodium hydroxide solution (30 ml) and diethyl ether (15 ml) were then added to the reaction mixture. The aqueous phase was separated off, washed with diethyl ether (3×5 ml) and ethyl acetate (2×5 ml) and acidified (pH 4) with 1 N hydrochloric acid, after which a solid precipitate out. The aqueous phase was extracted with THF (4×10 ml) and the combined THF extracts were dried with magnesium sulfate, filtered and concentrated. The residue was purified by column chromatography [silica gel 60; THF/cyclohexane 1:2, then 1:1, with in each case 0.5% acetic acid]. Yellow solid. Yield: 178 mg (25% of theory)

LC-MS (method 1): $R_t$=3.6 min m/z: [M+H]$^+$=444.2

11e) 2-(1-(2-(5-Chlorothiophen-2-yl)-6,7-dihydro-5H-cyclopenta[d]pyrimidin-4-yl)-2-oxoindolin-5-yl) acetic acid Pyridine (324 μl, 317 mg, 4.01 mmol) and methanesulfonic acid chloride (142 μl, 211 mg, 1.84 mmol) were added to the product from 11d) (178 mg, 0.40 mmol) in 1,2-dichloroethane (3 ml) and the mixture was stirred at 0° C. for 1 h. The solid which had precipitated out was filtered off and 1 N hydrochloric acid (10 ml) and diethyl ether (10 ml) were added to the filtrate. The aqueous phase of the filtrate was separated off and extracted with diethyl ether (3×5 ml). The organic phases were then combined, washed with 1 N hydrochloric acid (3×5 ml), dried with magnesium sulfate and concentrated. The residue was purified by means of column chromatography [silica gel 60; methylene chloride, then diethyl ether, with in each case 0.5% acetic acid]. Pale yellow solid. Yield: 48 mg (28% of theory), Melting range: 223-226° C.

LC-MS (method 1): $R_t$=4.0 min, m/z: [M+H]$^+$=426.2

$^{13}$C-NMR (101 MHz, DMSO, δ ppm): 21.8, 29.0, 34.0, 36.4, 40.2, 111.1, 125.2, 125.6, 127.7, 128.2, 128.3, 128.6, 130.2, 132.1, 140.7, 141.1, 151.2, 157.8, 172.7, 172.9, 179.2

SYNTHESIS EXAMPLE NO. 12

2-(1-(2-(5-Fluorothiophen-2-yl)-6,7-dihydro-5H-cyclopenta[d]-pyrimidin-4-yl)-2-oxoindolin-5-yl) acetic acid (Compound No. 1-65)

12a) 2,2'-(4-(2-(5-Fluorothiophen-2-yl)-6,7-dihydro-5H-cyclopenta[d]pyrimidin-4-ylamino)-1,3-phenylene)diacetic acid Reaction of 2,2'-(4-amino-1,3-phenylene)diacetic acid di-sodium salt from 11c) (1.52 g) and 4-chloro-2-(5-fluorothiophen-2-yl)-6,7-dihydro-5H-cyclopenta[d]pyrimidine (510 mg, 2 mmol) analogously to instructions 11d). The reaction was worked up by the addition of water (50 ml) to the reaction mixture and the mixture was adjusted to pH 4 with 2 N hydrochloric acid and extracted with THF (4×20 ml). The combined organic phases were dried with magnesium sulfate and concentrated. The residue was purified by column chromatography [silica gel 60; methylene chloride/methanol 15:1, with 1% acetic acid]. Beige-coloured solid. Yield: 400 mg (47% of theory)

LC-MS (method 1): $R_t$=3.33 min, m/z: [M+H]$^+$=428.2

$^1$H-NMR (400 MHz, DMSO-d6, δ ppm): 2.05 (m, 2H), 2.70 (m, 2H), 2.82 (m, 2H), 3.56 (s, 2H), 3.63 (s, 3H), 6.71 (dd, J=1.9, 4.2, 1H), 7.20-7.22 (2H), 7.35 (t, J=4.1, 1H), 7.56 (d, J=8.7, 1H), 8.62 (s, 1H), 12.17 (s (broad), 2H)

$^{13}$C-NMR (101 MHz, DMSO-d6, δ ppm): 21.1, 27.0, 33.5, 35.6, 37.8, 109.4 (d, $J_{C,F}$=10.6), 115.1, 123.9 (d, $J_{C,F}$=4.4), 125.2, 127.9, 129.5, 131.3, 131.5, 132.7 (d, $J_{C,F}$=2.4), 135.9, 156.7, 157.6, 165.9 (d, $J_{C,F}$=290.0), 172.6, 172.9, 173.0

12b) 2-(1-(2-(5-Fluorothiophen-2-yl)-6,7-dihydro-5H-cyclopenta[d]pyrimidin-4-yl)-2-oxoindolin-5-yl) acetic acid Reaction of the phenyldiacetic acid from 12a) (350 mg, 0.82 mmol) analogously to instructions 11e). 1 N hydrochloric acid (20 ml) was added to the reaction mixture. The aqueous phase was then separated off and extracted with ethyl acetate (3×20 ml). The organic phases were combined, dried with magnesium sulfate and concentrated. The residue was purified by means of column chromatography [silica gel 60; methylene chloride/methanol 100:1, with 0.5% acetic acid]. Colourless solid. Melting range 240-242° C.; Yield: 244 mg (73% of theory)

LC-MS (method 1): $R_t$=3.91 min, m/z: [M+H]$^+$=410.20

$^1$H-NMR (400 MHz, DMSO-d6, δ ppm): 2.07 (m, 2H), 2.86 (m, 2H), 3.05 (m, 2H), 3.57 (s, 2H), 3.85 (s, 2H), 6.84 (dd, J=1.9, 4.2, 1H), 7.15 (dd, J=1.7, 8.2, 1H), 7.22 (d, J=8.2, 1H), 7.28 (d, J=1.7, 1H), 7.61 (dd (t-like), J=4.1, 1H), 12.29 (s, 1H)

$^{13}$C-NMR (101 MHz, DMSO-d6, δ ppm): 21.8, 28.9, 33.9, 35.3, 40.1, 110.1 (d, $J_{C,F}$=10.9), 111.0, 125.2, 125.6, 125.7, 127.3, 128.2, 130.1, 131.0 (d, $J_{C,F}$=3.0), 140.7, 151.1, 158.2, 166.8 (d, $J_{C,F}$=291.4), 172.7, 172.9, 179.1

SYNTHESIS EXAMPLE NO. 13

2-(1-(2-(3-Chloro-4-methoxyphenyl)-6,7-dihydro-5H-cyclopenta[d]-pyrimidin-4-yl)-2-oxoindolin-5-yl)acetic acid (Compound No. 1-66)

13a) 2,2'-(4-(2-(3-Chloro-4-methoxyphenyl)-6,7-dihydro-5H-cyclopenta[d]pyrimidin-4-ylamino)-1,3-phenylene)diacetic acid Preparation analogously to instructions 11d) from 4-chloro-2-(3-chloro-4-methoxyphenyl)-6,7-dihydro-5H- cyclopenta[d]pyrimidine (500 mg, 1.70 mmol) and the disodium salt from 11c) (1.29 g). The final purification of the crude product was carried out by means of column chromatography [silica gel 60; ethyl acetate/methanol 95:5, with 0.5% acetic acid]. Yellow solid. Yield: 258 mg (32% of theory)

LC-MS (method 1): $R_t$=3.25 min, m/z: $[M+H]^+$=468.2

$^{13}$C-NMR (101 MHz, DMSO, δ ppm): 21.2, 27.1, 33.7, 37.8, 40.4, 56.2, 112.4, 115.0, 120.8, 125.4, 127.4, 127.9, 128.7, 129.6, 131.3, 131.5, 131.6, 136.2, 155.8, 157.1, 160.1, 172.2, 172.6, 173.0

13b) 2-(1-(2-(3-Chloro-4-methoxyphenyl)-6,7-dihydro-5H-cyclopenta[d]pyrimidin-4-yl)-2-oxoindolin-5-yl)acetic acid Reaction of the product from 13a) (243 mg, 0.52 mmol) analogously to instructions 11e). In deviation, the crude product was not purified by column chromatography but suspended in methanol (3 ml). The solid was then filtered off, washed with methanol (2×2 ml) and diethyl ether (1×2 ml) and dried in vacuo. White solid. Yield: 122 mg (52% of theory). Melting range 206-207° C.

LC-MS (method 1): $R_t$=3.95 min, m/z: $[M+H]^+$=450.2

$^{13}$C-NMR (101 MHz, DMSO, δ ppm): 21.8, 28.9, 34.1, 35.4, 40.2, 56.3, 110.9, 112.9, 121.4, 125.3, 125.7, 127.4, 127.9, 128.3, 128.9, 130.1, 130.2, 140.9, 151.4, 156.5, 160.8, 172.8, 173.0, 179.1

SYNTHESIS EXAMPLE NO. 14

2-(3-(2-(5-Chlorothiophen-2-yl)-6,7-dihydro-5H-cyclopenta[d]-pyrimidin-4-yl)-2-oxo-2,3-dihydrobenzo[d]oxazol-6-yl)acetic acid (Compound No. 1-67)

14a) 2-(4-Amino-3-hydroxyphenyl)acetic acid methyl ester acetate

Zinc (3.28 g, 50 mmol) and then, dropwise, acetic acid (5.72 ml, 100 mmol) were added to a solution of 2-(3-hydroxy-4-nitrophenyl)acetic acid methyl ester (2.11 g, 10 mmol) in ethanol (50 ml) and the mixture was then stirred at room temperature for 15 min Methyl tert-butyl ether (100 ml) was added and the mixture was filtered over silica gel, the silica gel then being eluted with ethyl acetate (200 ml). The solvents were distilled off on a rotary evaporator. Grey solid. Yield: 2.1 g (88% of theory)

$^1$H-NMR (400 MHz, DMSO-d6, δ ppm): 1.91 (s, 3H, CH$_3$COOH), 3.39 (s, 2H), 3.57 (s, 3H), 6.42 (dd, J=1.9, 7.9, 1H), 6.51 (d, J=7.9, 1H), 6.55 (d, J=1.9, 1H), 8.97 (s (broad), 1H)

$^{13}$C-NMR (101 MHz, DMSO-d6, δ ppm): 20.9 (CH$_3$COOH), 39.7, 51.3, 114.2, 115.2, 120.1, 122.0, 135.0, 143.9, 171.9 (CH$_3$COOH), 172.1

LC-MS (method 1): $R_t$=0.31 min, m/z: $[M+H]^+$=182.20

14b) 2-(4-(2-(5-Chlorothiophen-2-yl)-6,7-dihydro-5H-cyclopenta[d]pyrimidin-4-ylamino)-3-hydroxyphenyl)acetic acid methyl ester The amino compound from 14a) (965 mg, 4 mmol), 4-chloro-2-(5-chlorothiophen-2-yl)-6,7-dihydro-5H-cyclopenta[d]pyrimidine (542 mg, 2 mmol), caesium carbonate (3.25 g, 10 mmol), BINAP (75 mg, 120 µmol) and palladium (II) acetate (23 mg, 100 µmol) in dioxane (40 ml) were stirred at 100° C. under argon for 3 h. Water (25 ml) was added to the reaction mixture and the aqueous phase was separated off and extracted with ethyl acetate (3×25 ml). The combined organic phases were then dried with magnesium sulfate and concentrated. The residue was purified by column chromatography [silica gel 60; cyclohexane/ethyl acetate 2:1, then methanol and THF]. Colourless solid. Yield: 730 mg (88% of theory)

LC-MS (method 1): $R_t$=3.88 min, m/z: $[M+H]^+$=416.20

$^1$H-NMR (400 MHz, CDCl$_3$, δ ppm): 2.07 (m, 2H), 2.78 (m, 2H), 2.84 (m, 2H), 3.60 (s, 2H), 3.62 (s, 3H), 6.77 (d, J=8.1, 1H), 6.85 (d, J=1.4, 1H), 7.14 (d, J=3.9, 1H), 7.57 (d, J=3.9, 1H), 7.86 (dd, J=8.1, 1H), 7.86 (s, 1H), 9.87 (s, 1H)

14c) 2-(4-(2-(5-Chlorothiophen-2-yl)-6,7-dihydro-5H-cyclopenta[d]pyrimidin-4-ylamino)-3-hydroxyphenyl)acetic acid 2 N sodium hydroxide solution (1 ml) was added to the product from 14b) (140 mg, 0.34 mmol) in methanol (4 ml) and the mixture was stirred at room temperature for 16 h. 2 N hydrochloric acid (1 ml) and methyl tert-butyl ether (10 ml) were added and the mixture was then stirred for 20 min. The precipitate was then filtered off, washed with methyl tert-butyl ether and dried. Colourless solid. Yield: 125 mg (92% of theory)

LC-MS (method 1): $R_t$=3.72 min, m/z: $[M+H]^+$=403.20

$^1$H-NMR (400 MHz, DMSO-d6, δ ppm): 2.05 (m, 2H), 2.78-2.85 (4H), 3.47 (s, 2H), 6.75 (dd, J=1.6, 8.2, 1H), 6.90 (d, J=1.6, 1H), 7.14 (d, J=4.0, 1H), 7.56 (d, J=4.0, 1H), 7.86 (d, J=8.2, 1H), 7.96 (s, 1H), 10.03 (s, 1H)

$^{13}$C-NMR (101 MHz, DMSO-d6, δ ppm): 21.0, 26.8, 33.5, 40.4, 115.7, 116.5, 119.7, 122.5, 125.4, 126.7, 128.0, 130.6, 130.8, 142.9, 148.3, 156.3, 157.3, 171.6, 172.6

14d) 2-(3-(2-(5-Chlorothiophen-2-yl)-6,7-dihydro-5H-cyclopenta[d]pyrimidin-4-yl)-2-oxo-2,3-dihydrobenzo[d]oxazol-6-yl)acetic acid The carboxylic acid from 14c) (330 mg, 0.82 mmol) in THF (5 ml) was cooled to 0° C. and a solution of CDI (266 mg, 1.64 mmol) in THF (5 ml) was slowly added. The reaction mixture was heated at 70° C. for 1 h and then cooled to room temperature, water (5 ml) and trifluoroacetic acid (0.2 ml) were added and the mixture was stirred for 3 h. Brine (20 ml) was added and the aqueous phase was separated off and extracted with THF (3×20 ml). The combined organic phases were dried with magnesium sulfate and concentrated. The residue was purified by column chromatography [silica gel 60; methylene chloride/methanol 15:1→10:1]. Colourless solid. Yield: 84 mg (24% of theory)

$^1$H-NMR (400 MHz, DMSO-d6, δ ppm): 2.09 (m, 2H), 3.03 (m, 2H), 3.06 (m, 2H), 3.51 (s, 2H), 7.17 (dd, J=1.3, 8.2, 1H), 7.22 (d, J=4.0, 1H), 7.39 (d, J=1.3, 1H), 7.47 (d, J=8.2, 1H), 7.75 (d, J=4.0, 1H)

$^{13}$C-NMR (101 MHz, DMSO-d6, δ ppm): 21.9, 29.0, 34.0, 42.5, 111.1, 111.7, 125.1, 126.0, 126.9, 128.5, 128.5, 128.6, 128.6, 132.4, 140.7, 142.5, 150.0, 150.2, 157.7, 180.1

LC-MS (method 1): $R_t$=3.70 min, m/z: $[M+H]^+$=429.20

SYNTHESIS EXAMPLE NO. 15

2-(1-(2-(5-Chlorothiophen-2-yl)-6,7-dihydro-5H-cyclopenta[d]pyrimidin-4-yl)-1H-benzo[d]imidazol-5-yl)acetic acid (Compound No. 1-62)

15a) 2-(4-(2-(5-Chlorothiophen-2-yl)-6,7-dihydro-5H-cyclopenta[d]pyrimidin-4-ylamino)-3-nitrophenyl)acetic acid ethyl ester 4-Chloro-2-(5-chlorothiophen-2-yl)-6,7-dihydro-5H-cyclopenta[d]pyrimidine (407 mg, 1.5 mmol), 2-(4-amino-3- nitrophenyl)acetic acid ethyl ester (336 mg, 1.5 mmol), caesium carbonate (978 mg, 3 mmol), BINAP (93 mg, 150 μmol) and palladium(II) acetate (34 mg, 150 μmol) in dioxane (7.5 ml) were stirred at 100° C. for 2 h. Water (50 ml) was added to the reaction mixture and the aqueous phase was separated off and extracted with methylene chloride (3×20 ml). The combined organic phases were dried with magnesium sulfate and concentrated. The residue was purified by column chromatography [silica gel 60; cyclohexane/ethyl acetate 3:1]. Colourless solid. Yield: 520 mg (76% of theory)

LC-MS (method 1): $R_t$=4.44 min, m/z: $[M+H]^+$=460.20

$^1$H-NMR (400 MHz, CDCl$_3$, δ ppm): 1.29 (t, J=7.1, 3H), 2.23 (m, 2H), 2.93 (m, 2H), 3.03 (m, 2H), 3.67 (s, 2H), 4.20 (q, J=7.1, 2H), 6.94 (d, J=4.0, 1H), 6.68 (dd, J=2.2, 9.0, 1H), 7.70 (d, J=4.0, 1H), 7.20 (d, J=2.2, 1H), 9.19 (d, J=9.0, 1H), 10.19 (s, 1H)

15b) 2-(3-Amino-4-(2-(5-chlorothiophen-2-yl)-6,7-dihydro-5H-cyclopenta[d]pyrimidin-4-ylamino)phenyl)acetic acid ethyl ester Zinc (459 mg, 7 mmol) and iron(III) chloride (252 mg, 1.55 mmol) were added to a solution of the ester from 15a) (357 mg, 0.78 mmol) in DMF (10 ml) and water (2 ml) and the mixture was stirred at 150° C. for 30 min Saturated sodium carbonate solution (10 ml) and thereafter water (50 ml) were then added and the aqueous phase was extracted with ethyl acetate (4×20 ml). The combined organic phases were dried with magnesium sulfate and concentrated. The residue was purified by column chromatography [silica gel 60; cyclohexane/ethyl acetate 2:1]. The product mixture isolated in this way was further purified by means of HPLC. Colourless solid. Yield: 176 mg (53% of theory)

LC-MS (method 1): $R_t$=3.68 min, m/z: $[M+H]^+$=430.20

$^1$H-NMR (400 MHz, CDCl$_3$, δ ppm): 1.26 (t, J=7.1, 3H), 2.06 (m, 2H), 2.56 (m, 2H), 2.91 (m, 2H), 3.55 (s, 2H), 4.17 (q, J=7.1, 2H), 6.15 (s, 1H), 6.73 (dd, J=1.8, 8.0, 1H), 6.77 (d, J=1.8, 1H), 6.88 (d, J=4.0, 1H), 7.27 (d, J=8.0, 1H), 7.63 (d, J=4.0, 1H), 8.01 (s, 1H)

15c) 2-(1-(2-(5-Chlorothiophen-2-yl)-6,7-dihydro-5H-cyclopenta[d]pyrimidin-4-yl)-1H-benzo[d]imidazol-5-yl)acetic acid ethyl ester Ethyl acetate (10 ml) was added to the suspension from the product of 15b) (159 mg, 0.37 mmol) and triethyl orthoformate (5 ml). The solvent was then removed on a rotary evaporator and the residue was heated at 200° C. in an oil bath for 30 min. The reaction mixture was cooled and dissolved in methylene chloride to remove the excess ortho ester, and the solution was then concentrated. Colourless solid. Yield: 157 mg (96% of theory)

$^1$H-NMR (400 MHz, CDCl$_3$, δ ppm): 1.27 (t, J=7.2, 3H), 2.87 (m, 2H), 3.15 (m, 2H), 3.22 (m, 2H), 3.79 (s, 2H), 7.00 (d, J=3.9, 1H), 7.43 (dd, J=1.6, 8.6, 1H), 7.80 (d, J=1.6, 1H), 7.85 (d, J=3.9, 1H), 8.37 (d, J=8.6, 1H), 8.49 (s, 1H)

15d) 2-(1-(2-(5-Chlorothiophen-2-yl)-6,7-dihydro-5H-cyclopenta[d]pyrimidin-4-yl)-1H-benzo[d]imidazol-5-yl)acetic acid 2 N sodium hydroxide solution (0.5 ml) was added to the product from 15c) (159 mg, 0.37 mmol) in THF (6 ml) and the mixture was stirred at room temperature for 64 h. 2 N hydrochloric acid solution (0.5 ml) was then added and the THF was largely distilled off. The suspension was diluted with methanol (5 ml) and the solid was filtered off Colourless solid. Melting range: 268-270° C. Yield: 86 mg (58% of theory)

LC-MS (method 1): $R_t$=4.01 min, m/z: $[M+H]^+$=412.10

$^1$H-NMR (400 MHz, DMSO-d6, δ ppm): 2.15 (m, 2H), 3.05 (m, 2H), 3.23 (m, 2H), 3.73 (s, 2H), 7.24 (d, J=4.0, 1H), 7.35 (d, J=8.4, 1H), 7.69 (s, 1H), 7.83 (d, J=4.0, 1H), 8.24 (d, J=8.4, 1H), 8.74 (s, 1H), 12.33 (s, 1H)

$^{13}$C-NMR (100 MHz, DMSO-d6, δ ppm): 21.9, 29.5, 34.0, 40.4, 114.3, 120.5, 121.5, 125.9, 128.4, 128.6, 130.7, 130.8, 132.3, 140.9, 142.4, 143.5, 152.0, 157.8, 172.8, 178.9

SYNTHESIS EXAMPLE NO. 16

2-(1-(2-(5-Chlorothiophen-2-yl)-6,7-dihydro-5H-cyclopenta[d]-pyrimidin-4-yl)-1H-indazol-5-yl)acetic acid (Compound No. 1-61)

16a) 2-(1-(2-(5-Chlorothiophen-2-yl)-6,7-dihydro-5H-cyclopenta[d]pyrimidin-4-yl)-1H-indazol-5-yl)acetic acid ethyl ester Potassium tert-butylate (217.7 mg, 1.94 mmol) and toluene (4 ml) were added to 4-chloro-2-(5-chlorothiophen-2-yl)-6,7-dihydro-5H-cyclopenta[d]pyrimidine (350 mg, 1.29 mmol), 2-(1H-indazol-5-yl)acetic acid ethyl ester (264 mg, 1.29 mmol), tBuXPhos (109.8 mg, 0.26 mmol) and Pd$_2$(dba)$_3$ (59.2 mg, 0.06 mmol) under argon and the mixture was stirred at 80° C. for 90 min. The reaction mixture was filtered over Celite® and the volatile constituents of the filtrate were removed in vacuo. The residue was purified by means of column chromatography [silica gel; cyclohexane/ethyl acetate 5:1]. Colourless solid. Yield 94 mg (17% of theory)

$^{13}$C-NMR (101 MHz, CDCl$_3$, δ ppm): 14.2, 22.0, 32.0, 34.7, 41.2, 61.0, 116.1, 120.4, 121.0, 126.2, 127.5, 129.4, 129.9, 133.5, 138.1, 138.8, 142.0, 155.3, 158.3, 171.6, 177.9

16b) 2-(1-(2-(5-Chlorothiophen-2-yl)-6,7-dihydro-5H-cyclopenta[d]pyrimidin-4-yl)-1H-indazol-5-yl)acetic acid Preparation from the ester obtained under 16a) (91 mg, 0.21 mmol) analogously to instructions 1e). Colourless solid. Yield: 62 mg (72% of theory)

$^{13}$C-NMR (101 MHz, DMSO-d6, δ ppm): 21.3, 31.6, 33.9, 40.3, 115.0, 119.8, 121.5, 125.7, 128.0, 128.4, 130.4, 130.5, 131.8, 137.7, 138.9, 141.4, 154.5, 157.2, 172.7, 177.7

SYNTHESIS EXAMPLE NO. 17

2-(1-(2-(3-Fluoro-4-methoxyphenyl)-6,7-dihydro-5H-cyclopenta[d]-pyrimidin-4-yl)-1H-indazol-5-yl)acetic acid (Compound No. 1-60)

17a) 2-(1-(2-(3-Fluoro-4-methoxyphenyl)-6,7-dihydro-5H-cyclopenta[d]pyrimidin-4-yl)-1H-indazol-5-yl)acetic acid ethyl ester The target compound was prepared from 4-chloro-2-(3-fluoro-4-methoxyphenyl)-6,7-dihydro-5H-cyclopenta[d]pyrimidine (423 mg, 1.52 mmol) and 2-(1H-indazol-5-yl)acetic acid ethyl ester (310 mg, 1.52 mmol) analogously to instructions 16a). Colourless solid. Yield: 130 mg (19% of theory)

$^{13}$C-NMR (101 MHz, CDCl$_3$, δ ppm): 14.2, 22.1, 31.8, 34.8, 41.2, 56.3, 61.0, 112.9, 112.9, 115.7, 115.8, 116.0, 120.4, 121.1, 124.4, 124.4, 126.1, 129.3, 129.7, 131.3, 131.4, 137.8, 138.8, 149.6, 149.7, 151.2, 153.6, 155.6, 161.7, 161.7, 172.6, 178.0

17b) 2-(1-(2-(3-Fluoro-4-methoxyphenyl)-6,7-dihydro-5H-cyclopenta[d]pyrimidin-4-yl)-1H-indazol-5-yl)acetic acid Saponification of the ester obtained under 17a) (125 mg, 0.28 mmol) analogously to instructions 1e). Colourless solid. Yield: 101 mg (86% of theory). Melting range: 236-238° C.

$^{13}$C-NMR (101 MHz, DMSO-d6, δ ppm): 21.3, 31.4, 34.0, 40.3, 56.1, 113.7, 113.7, 114.5, 114.7, 114.7, 119.7, 121.5, 124.3, 124.4, 125.7, 130.1, 130.2, 130.3, 137.7, 138.5, 149.1, 149.2, 150.1, 152.5, 154.8, 160.5, 160.6, 172.8, 177.7

SYNTHESIS EXAMPLE NO. 18

2-(1-(2-(5-Chlorothiophen-2-yl)-5,6,7,8-tetrahydroquinazolin-4-yl)indolin-5-yl)acetic acid (Compound No. 1-50)

18a) 2-(1-(2-(5-Chlorothiophen-2-yl)-5,6,7,8-tetrahydroquinazolin-4-yl)indolin-5-yl)acetic acid methyl ester Preparation from 4-chloro-2-(5-chlorothiophen-2-yl)-5,6,7,8-tetrahydroquinazoline (301 mg, 1.06 mmol) and 2-(indolin-5-yl)acetic acid methyl ester (203 mg, 1.06 mmol) analogously to instructions 1d). Yellow solid. Yield: 339 mg (73% of theory)

$^{13}$C-NMR (101 MHz, CDCl$_3$, δ ppm): 22.3, 22.7, 26.1, 28.9, 32.4, 40.7, 52.0, 52.4, 114.2, 116.9, 125.6, 126.7, 126.8, 127.2, 127.5, 132.4, 132.9, 142.6, 144.4, 156.5, 160.7, 166.8, 172.4

18b) 2-(1-(2-(5-Chlorothiophen-2-yl)-5,6,7,8-tetrahydroquinazolin-4-yl)indolin-5-yl)acetic acid Saponification of the ester obtained under 18a) (339 mg, 0.77 mmol) analogously to instructions 1e). Pale yellow solid. Yield: 286 mg (87% of theory). Melting range: 120-122° C.

$^{13}$C-NMR (101 MHz, DMSO-d6, δ ppm): 21.6, 22.2, 25.5, 28.5, 31.9, 40.2, 52.0, 114.7, 116.4, 125.6, 126.9, 127.2, 128.1, 130.9, 132.1, 142.4, 143.4, 155.0, 160.4, 166.2, 168.4, 173.0

SYNTHESIS EXAMPLE NO. 19

2-(1-(2-(3-Chloro-4-methoxyphenyl)-5,6,7,8-tetrahydroqiuinazolin-4-yl)indolin-5-yl)acetic acid (Compound No. 1-39)

19a) 2-(1-(2-(3-Chloro-4-methoxyphenyl)-5,6,7,8-tetrahydroquinazolin-4-yl)indolin-5-yl)acetic acid methyl ester The target compound was prepared analogously to instructions 1d) from 4-chloro-2-(3-chloro-4-methoxyphenyl)-5,6,7,8-tetrahydroquinazoline (483 mg, 1.56 mmol) and 2-(indolin-5-yl)acetic acid methyl ester (299 mg, 1.56 mmol). Beige solid. Yield: 164 mg (34% of theory)

LC-MS (method 1): R$_t$=3.5 min, m/z: [M+H]$^+$=416.3

$^{13}$C-NMR (101 MHz, CDCl$_3$, δ ppm): 22.4, 22.7, 26.0, 28.9, 32.6, 40.7, 52.0, 52.5, 56.2, 111.5, 113.7, 117.1, 122.4, 125.7, 126.4, 127.4, 127.6, 129.9, 131.9, 132.4, 144.8, 156.4, 159.2, 161.0, 166.8, 172.5

19b) 2-(1-(2-(3-Chloro-4-methoxyphenyl)-5,6,7,8-tetrahydroquinazolin-4-yl)indolin-5-yl)acetic acid 1 N sodium hydroxide solution (0.66 ml, 0.66 mmol) was added to the methyl ester from 19a) (152 mg, 0.33 mmol) in methanol (1.5 ml) and 1,4-dioxane (1.5 ml) and the mixture was stirred at room temperature for 1 h. Water (10 ml) and 1 N hydrochloric acid (0.66 ml) were then added to the reaction mixture. The solid which had precipitated out was filtered off, washed with water (3×2 ml) and cyclohexane (2×2 ml) and dried in vacuo. Pale yellow solid. Yield: 99 mg (67% of theory). Melting range 121-125° C.

$^{13}$C-NMR (101 MHz, DMSO-d6, δ ppm): 21.7, 22.2, 25.3, 28.5, 32.1, 40.2, 52.0, 56.2, 112.6, 114.1, 116.5, 121.0, 125.7, 127.1, 127.4, 127.7, 128.6, 131.1, 132.2, 143.8, 156.0, 157.6, 160.7, 166.2, 173.0

SYNTHESIS EXAMPLE NO. 20

2-(1-(2-(3-Chloro-4-methoxyphenyl)-6,7-dihydro-5H-cyclopenta[d]-pyrimidin-4-yl)indolin-4-yloxy)acetic acid (Compound No. 1-76)

20a) Ethyl 2-(1-(2-chloro-6,7-dihydro-5H-cyclopenta[d]pyrimidin-4-yl)indolin-4-yloxy)acetate 2,4-Dichloro-6,7-dihydro-5H-cyclopenta[d]pyrimidine (5.00 g, 26.45 mmol), ethyl 2-(indolin-4-yloxy)acetate (6.15 g, 27.78 mmol) and Hünig base (9.0 ml) in NMP (50 ml) were stirred overnight at 80° C. The reaction mixture was cooled to ambient temperature, ethyl acetate (200 ml) was added and the phases were separated. The organic layer was washed with water (3×50 ml), dried over magnesium sulfate and evaporated. The residue was triturated with methanol and hexane. The precipitating solid was filtered off, washed with hexane and dried in vacuo. Beige solid. Yield: 7.1 g (72% of theory)

LC-MS (method 2): R$_t$=0.83 min, m/z: [M+H]$^+$=374.1

20b) Ethyl 2-(1-(2-(3-chloro-4-methoxyphenyl)-6,7-dihydro-5H-cyclopenta[d]pyrimidin-4-yl)indolin-4-yloxy)acetate Four glass tubes were loaded under a nitrogen atmosphere each with the product of 20a) (349 mg, 0.94 mmol), 3-chloro-4-methoxyphenylboronic acid (261 mg, 1.40 mmol), 2 N sodium carbonate solution (2.3 ml) and tetrakis(triphenylphosphine)-palladium(0) (33 mg, 29 μmol) in 1,2-dimethoxymethane (16 ml). The tubes were sealed and then irradiated with microwaves for 2 h at 120° C. Water (120 ml) was added and the mixture was filtered through a Celite® pad and extracted with dichloromethane (3×90 ml). The combined organic layers were dried over magnesium sulfate, filtered and evaporated. The residue was chromatographed [silica gel 60; dichloromethane/diethylether 25:1]. Yield: 500 mg (28% of theory)

LC-MS (method 2): R$_t$=0.87 min, m/z: [M+H]$^+$=480.1

20c) 2-(1-(2-(3-Chloro-4-methoxyphenyl)-6,7-dihydro-5H-cyclopenta[d]pyrimidin-4-yl)indolin-4-yloxy)acetic acid Lithium hydroxide (48 mg, 2.08 mmol) was added to a suspension of the product of 20b) (500 mg, 1.04 mmol) in THF (8 ml) and water (1 ml) and the mixture was stirred for 24 h at room temperature. Water (30 ml) was added and the pH value was adjusted to 1-2 with 1N hydrochloride solution. The mixture was extracted with dichloromethane/THF (4:1) and the combined organic layers were washed with brine, dried over magnesium sulfate and evaporated. The residue was triturated with diethyl ether and ethanol, filtered, washed with ether and dried in vacuo. Colorless solid. Yield: 500 mg (76% of theory)

LC-MS (method 2): $R_t$=0.69 min, m/z: $[M+H]^+$=452.1

SYNTHESIS EXAMPLE NO. 21

2-(1-(2-(5-Chlorothiophen-2-yl)-5,7-dihydrothieno[3,4-d]pyrimidin-4-yl)indolin-5-yl)acetic acid (Compound No. 1-20)

21a) 2-(5-Chlorothiophen-2-yl)-5,7-dihydrothieno[3,4-d]pyrimidin-4-ol

Hünig base (0,515 ml, 392 mg, 3.03 mmol) and 5-chlorothiophene-2-carboximidamide (500 mg, 2.53 mmol) were added to methyl 4-oxotetrahydrothiophene-3-carboxylate (810 mg, 5.06 mmol) in n-propanol (2 ml) and the mixture was irradiated with microwaves in a sealed tube at 90° C. for 16 h. The reaction mixture was cooled, diluted with ethyl acetate (10 ml) and stirred for 30 min under cooling with an ice bath. The precipitate was filtered off and washed with ethyl acetate (3 ml) and diethyl ether (3 ml). Beige solid. Yield: 50% of theory $^{13}$C-NMR (101 MHz, DMSO-d6, δ ppm): 3.9 (2H, d, J=2.8), 4.1 (2H, d, J=3.2), 7.2 (1H, d, J=4.4), 8.0 (1H, d, J=3.6)

21b) 4-Chloro-2-(5-chlorothiophen-2-yl)-5,7-dihydrothieno[3,4-d]pyrimidine

A mixture consisting of the thioether from 21a) (321 mg, 1.18 mmol) and phosphorus oxychloride (2.2 ml, 3.69 g, 23.7 mmol) was heated for 2 h at 95° C. The reaction mixture was cooled with an ice bath and then slowly quenched with water (15 ml). Dichloromethane was added (20 ml) and the mixture was stirred for 10 min. The phases were separated and the aqueous phase was extracted with dichloromethane (2×20 ml). The organic layers were combined, dried over sodium sulfate, and evaporated. Orange solid.

Yield: 312 mg (92% of theory). Melting range: 150-152° C.

$^{13}$C-NMR (101 MHz, CDCl3, δ ppm): 33.5, 38.8, 127.6, 127.7, 129.4, 135.5, 139.5, 157.7, 160.1, 172.0

21c) Methyl 2-(1-(2-(5-chlorothiophen-2-yl)-5,7-dihydrothieno[3,4-d]pyrimidin-4-yl)indolin-5-yl)acetate Methyl 2-(indolin-5-yl)acetate (192 mg, 1.0 mmol), 4-chloro-2-(5-chlorothiophen-2-yl)-5,7-dihydrothieno[3,4-d]pyrimidine (289 mg, 1.0 mmol), palladium (II)acetate (13 mg, 0,059 mmol), caesium carbonate (391 mg, 1.2 mmol) and BINAP (45.5 mg, 0,073 mmol) in dry dioxane (3 ml) were heated for 1.5 h at 110° C. The mixture was diluted with dichloromethane (1 ml) and chromatographed [silica gel 60; ethyl acetate/cyclohexane 1:3]. Yellow solid. Yield: 260 mg (59% of theory). Melting range: 167-160° C.

$^{13}$C-NMR (101 MHz, CDCl3, δ ppm): 28.6, 34.8, 38.1, 40.6, 50.7, 52.0, 112.4, 116.6, 125.6, 127.3, 127.6, 128.0, 128.3, 132.0, 133.6, 141.8, 142.9, 157.6, 158.4, 171.2, 172.2

21d) 2-(1-(2-(5-chlorothiophen-2-yl)-5,7-dihydrothieno[3,4-d]pyrimidin-4-yl)indolin-5-yl)acetic acid 1 N Sodium hydroxide solution (1.69 ml, 1.69 mmol) was added to the product of 21c) (150 mg, 0,338 mmol) in THF (10 ml) and the mixture was stirred for 16 h at room temperature. Water (2 ml) and 1N hydrochloric acid (1.7 ml) were then added and stirring was continued for 1.5 h. The precipitate was filtered off and washed with water (2×2 ml) and dichloromethane (2×2 ml). Yellow solid. Yield: 89 mg (61% of theory). Melting point: 143-145° C.

13C-NMR (101 MHz, DMSO-d6, δ ppm): 27.9, 33.8, 37.2, 38.8, 40.1, 49.9, 112.6, 116.3, 125.9, 127.6, 127.7, 128.3, 129.2, 131.5, 132.2, 141.7, 142.2, 156.9, 157.0, 170.4, 172.8

SYNTHESIS EXAMPLE NO. 22

2-(1-(2-(5-Chlor-thiophen-2-yl)-6-oxo-5,7-dihydro-thieno[3,4-d]pyrimidin-4-yl)-2,3-dihydro-1H-indol-5-yl)acetic acid (Compound No. 1-21)

Peracetic acid (39% in acetic acid; 0.93 mmol, 157.7 µl) was added to 2-(1-(2-(5-chlorothiophen-2-yl)-5,7-dihydrothieno[3,4-d]pyrimidin-4-yl)indolin-5-yl)acetic acid (200 mg, 0.47 mmol) dissolved in sulfolane (6 ml) at ambient temperature and the mixture was stirred for 1.5 h. Water (40 ml) was poured into the mixture and the precipitating solid was filtered off, washed with water (4×5 ml) and dried in vacuo. Orange solid. Yield: 160 mg (77% of theory). Melting range: 180-185° C.

$^{13}$C-NMR (101 MHz, DMSO-d6, δ ppm): 28.0, 40.1, 50.4, 56.8, 59.3, 108.8, 116.3, 125.8, 127.7, 128.0, 128.5, 129.5, 131.9, 132.5, 141.6, 142.0, 157.8, 158.2, 167.9, 172.8

SYNTHESIS EXAMPLE NO. 23

2-(1-(2-(5-Chlor-thiophen-2-yl)-6,6-dioxo-5,7-dihydro-thieno[3,4-d]pyrimidin-4-yl)-2,3-dihydro-1H-indol-5-yl)acetic acid (Compound No. 1-22)

m-Chloroperoxybenzoic acid (77%, 323.2 mg, 1.44 mmol) was added at room temperature to the product from 21 d) (200 mg, 0.47 mmol) in sulfolane (6 ml) and the mixture was stirred for 18 h at ambient temperature. Water (10 ml) was poured into the reaction mixture and the resulting precipitate was filtered off, washed with water (4×5 ml) and dried. Trituration of the raw product in methanol (5 ml) provided the target compound as a yellow solid. Yield: 113 mg (53% of theory)

$^{13}$C-NMR (101 MHz, DMSO-d6, δ ppm): 28.0, 40.1, 50.2, 55.2, 56.2, 108.0, 116.6, 125.8, 127.7, 128.4, 128.5, 129.9, 132.3, 132.6, 141.3, 141.7, 156.0, 157.3, 161.4, 172.8

SYNTHESIS EXAMPLE NO. 24

2-(1-(2-(5-Fluoro-thiophen-2-yl)-6,6-dioxo-5,7-dihydro-thieno[3,4-d]pyrimidin-4-yl)-2,3-dihydro-1H-indol-5-yl)acetic acid (Compound No. 1-25)

24a) Methyl 2-(1-(2-(5-fluorothiophen-2-yl)-5,7-dihydrothieno[3,4-d]pyrimidin-4-yl)indolin-5-yl)acetate Synthesized from 4-chloro-2-(5-fluorothiophen-2-yl)-5,7-dihydrothieno[3,4-d]pyrimidine (712 mg, 2.61 mmol) and methyl 2-(indolin-5-yl)acetate (500 mg, 2.61 mmol) in an analogous manner to procedure 21c). Light yellow solid. Yield: 550 mg (49% of theory)

LC-MS (Method 1): $R_t$=4.2 min, m/z: [M+H]$^+$=428.2

$^{13}$C-NMR (101 MHz, CDCl3, δ ppm): 28.6, 34.8, 38.2, 40.6, 50.8, 52.0, 108.8, 108.9, 112.2, 116.7, 125.4, 125.6, 128.0, 128.3, 131.5, 132.0, 143.0, 157.6, 158.8, 166.7, 169.6, 171.2, 172.2

24b) 2-(1-(2-(5-fluorothiophen-2-yl)-5,7-dihydrothieno[3,4-d]pyrimidin-4-yl)indolin-5-yl)acetic acid 1 N Sodium hydroxide solution (6.26 ml, 6.26 mmol) was added to the methyl ester from 24a) (535 mg, 1.25 mmol) in THF (3 ml) and the mixture was stirred for 30 min at 70° C. (oil bath temperature). Water (5 ml) and 1 N hydrochloric acid (6.26 ml) were added and the precipitating solid was filtered off, washed with water (3×2 ml) and dried in vacuo. Light yellow solid. Yield: 467 mg (90% of theory)

LC-MS (Method 1): $R_t$=4.05 min, m/z: [M+H]$^+$=414.1

$^{13}$C-NMR (101 MHz, DMSO-d6, δ ppm): 28.0, 33.8, 37.2, 40.2, 49.9, 109.8, 109.9, 112.4, 116.4, 125.2, 125.7, 127.6, 129.2, 131.6, 131.6, 132.2, 142.3, 157.0, 157.3, 165.0, 167.9, 170.4, 172.8

24c) 2-(1-(2-(5-Fluoro-thiophen-2-yl)-6,6-dioxo-5,7-dihydro-thieno[3,4-d]pyrimidin-4-yl)-2,3-dihydro-1H-indol-5-yl)acetic acid The product from 24b) (449.2 mg, 1.08 mmol) was reacted with m-chloroperoxybenzoic acid (77%, 323.2 mg, 1.44 mmol) in analogous manner as described for synthesis example No. 23 with the difference that the raw product was purified by chromatography [silica gel 60; THF/acetic acid 1000:1]. Yellow solid. Yield: 57 mg (12% of theory)

$^{13}$C-NMR (101 MHz, DMSO-d6, δ ppm): 28.0, 40.3, 50.2, 55.2, 56.2, 107.8, 110.1, 110.2, 116.6, 125.8, 126.0, 126.1, 127.7, 130.0, 131.2, 131.2, 132.6, 141.7, 156.0, 157.6, 161.3, 165.4, 168.3, 172.9

SYNTHESIS EXAMPLE NO. 25

2-(1-(2-(3-Fluoro-4-methoxy-phenyl)-6,6-dioxo-5,7-dihydro-thieno[3,4-d]pyrimidin-4-yl)-2,3-dihydro-1H-indol-5-yl)acetic acid (Compound No. 1-10)

25a) Methyl 2-(1-(2-(3-fluoro-4-methoxyphenyl)-5,7-dihydrothieno[3,4-d]pyrimidin-4-yl)indolin-5-yl)acetate Beige solid. LC-MS (Method 1): $R_t$=4.15 min, m/z: [M+H]$^+$=452.2

$^{13}$C-NMR (101 MHz, CDCl3, δ ppm): 28.7, 34.7, 38.4, 40.6, 51.0, 52.0, 56.2, 112.6, 112.7, 112.7, 115.8, 116.0, 116.0, 124.5, 125.7, 127.9, 131.0, 132.1, 143.2, 149.6, 149.7, 151.0, 153.4, 157.9, 161.7, 161.7, 171.5, 172.3

25b) 2-(1-(2-(3-Fluoro-4-methoxyphenyl)-5,7-dihydrothieno[3,4-d]pyrimidin-4-yl)indolin-5-yl)acetic acid Yellow solid. LC-MS (Method 1): $R_t$=4.00 min, m/z: [M+14]$^+$=438.2

$^{13}$C-NMR (101 MHz, DMSO-d6, δ ppm): 28.1, 33.7, 37.4, 40.1, 50.1, 56.1, 112.6, 113.6, 114.6, 114.8, 115.8, 124.3, 125.8, 127.5, 129.0, 130.3, 130.4, 132.2, 142.5, 149.0, 149.2, 150.1, 152.5, 157.4, 160.1, 160.2, 170.9, 172.9

25c) 2-(1-(2-(3-Fluoro-4-methoxy-phenyl)-6,6-dioxo-5,7-dihydro-thieno[3,4-d]pyrimidin-4-yl)-2,3-dihydro-1H-indol-5-yl)acetic acid Yellow solid. Melting range: 192-195° C.

LC-MS (Method 1): $R_t$=3.65 min, m/z: [M+H]$^+$=470.2

$^{13}$C-NMR (101 MHz, DMSO-d6, δ ppm): 28.1, 40.1, 50.4, 54.8, 55.2, 56.1, 56.5, 108.0, 113.7, 114.6, 114.8, 116.1, 124.5, 124.5, 125.9, 127.6, 129.6, 129.9, 130.0, 132.6, 141.9, 149.4, 149.5, 150.1, 152.5, 156.4, 160.4, 160.5, 161.6, 172.8

SYNTHESIS EXAMPLE NO. 26

2-(1-(2-(3-Chloro-4-methoxy-phenyl)-6,6-dioxo-5,7-dihydro-thieno[3,4-d]pyrimidin-4-yl)-2,3-dihydro-1H-indol-5-yl)acetic acid (Compound No. 1-11)

26a) Methyl 2-(1-(2-(3-chloro-4-methoxyphenyl)-5,7-dihydrothieno[3,4-d]pyrimidin-4-yl)indolin-5-yl)acetate Colorless solid. LC-MS (Method 1): $R_t$=4.25 min, m/z: [M+H]$^+$=468.2

$^{13}$C-NMR (101 MHz, DMSO-d6, δ ppm): 28.0, 33.7, 37.4, 39.6, 50.1, 51.6, 56.3, 112.5, 112.6, 115.9, 121.1, 125.7, 127.4, 127.8, 128.2, 128.9, 130.6, 132.4, 142.7, 156.3, 157.4, 159.9, 170.8, 171.8

26b) 2-(1-(2-(3-Chloro-4-methoxyphenyl)-5,7-dihydrothieno[3,4-d]pyrimidin-4-yl)indolin-5-yl)acetic acid Yellow solid. LC-MS (Method 1): $R_t$=4.15 min, m/z: [M+H]$^+$=454.2

$^{13}$C-NMR (101 MHz, DMSO-d6, δ ppm): 28.1, 33.8, 37.4, 40.1, 50.1, 56.3, 112.5, 112.6, 115.9, 121.1, 125.7, 127.4, 127.7, 128.9, 129.0, 130.6, 132.2, 142.5, 156.2, 157.4, 159.9, 170.8, 172.9

26c) 2-(1-(2-(3-Chloro-4-methoxy-phenyl)-6,6-dioxo-5,7-dihydro-thieno[3,4-d]pyrimidin-4-yl)-2,3-dihydro-1H-indol-5-yl)acetic acid Yellow solid. Melting range: 245-247° C. LC-MS (Method 1): $R_t$=3.75 min, m/z: [M+H]$^+$=486.1

$^{13}$C-NMR (101 MHz, DMSO-d6, δ ppm): 28.1, 40.1, 50.4, 55.2, 56.3, 56.5, 108.0, 112.8, 116.2, 121.2, 125.9, 127.5, 127.9, 129.0, 129.6, 130.3, 132.6, 141.9, 156.4, 156.6, 160.3, 161.6, 172.8

SYNTHESIS EXAMPLE NO. 27

2-(1-(2-(4-Methoxyphenyl)-6,6-dioxo-5,7-dihydro-thieno[3,4-d]pyrimidin-4-yl)-2,3-dihydro-1H-indol-5-yl)acetic acid (Compound No. 1-12)

27a) Methyl 2-(1-(2-(4-methoxyphenyl)-5,7-dihydrothieno[3,4-d]pyrimidin-4-yl)indolin-5-yl)acetate Colorless solid. LC-MS (Method 1): $R_t$=4.05 min, m/z: [M+H]$^+$=434.2

¹³C-NMR (101 MHz, DMSO-d6, δ ppm): 28.1, 33.8, 37.5, 39.6, 50.1, 51.6, 55.2, 112.1, 113.9, 115.9, 125.7, 127.7, 128.0, 129.3, 129.8, 132.3, 142.8, 157.4, 161.2, 170.8, 171.8

27b) 2-(1-(2-(4-Methoxyphenyl)-5,7-dihydrothieno[3,4-d]pyrimidin-4-yl)indolin-5-yl)acetic acid Yellow solid. LC-MS (Method 1): $R_t$=3.9 min, m/z: [M+H]⁺=420.2
¹³C-NMR (101 MHz, DMSO-d6, δ ppm): 28.1, 33.8, 37.5, 40.2, 50.1, 55.2, 112.0, 113.9, 115.8, 125.7, 127.5, 128.8, 129.3, 129.8, 132.1, 142.6, 157.4, 161.2, 170.8, 172.9

27c) 2-(1-(2-(4-Methoxyphenyl)-6,6-dioxo-5,7-dihydro-thieno[3,4-d]pyrimidin-4-yl)-2,3-dihydro-1H-indol-5-yl)acetic acid Yellow solid. Melting range: 239-243° C. LC-MS (Method 1): $R_t$=3.65 min, m/z: [M+H]⁺=452.2
¹³C-NMR (101 MHz, DMSO-d6, δ ppm): 28.1, 40.2, 50.3, 55.2, 55.3, 56.5, 107.5, 114.0, 116.1, 125.9, 127.7, 129.4, 129.4, 129.4, 132.5, 142.0, 156.4, 161.5, 161.6, 172.8

SYNTHESIS EXAMPLE NO. 28

2-((1-(2-(5-Fluoro-thiophen-2-yl)-6,6-dioxo-5,7-dihydro-thieno[3,4-d]-pyrimidin-4-yl)-2,3-dihydro-1H-indol-4-yl)oxy)-N,N-dimethyl-acetamide (Compound No. 2-17)

28a) 2-(1-(2-(5-Fluorothiophen-2-yl)-5,7-dihydrothieno[3,4-d]pyrimidin-4-yl)indolin-4-yloxy)-N,N-dimethylacetamide The product was obtained from 2-(indolin-4-yloxy)-N,N-dimethylacetamide (200 mg, 0,908 mmol) and 4-chloro-2-(5-fluorothiophen-2-yl)-5,7-dihydrothieno[3,4-d]pyrimidine (248 mg, 0,908 mmol) in an analogous manner to procedure 21c). Beige solid. Yield: 241 mg (58% of theory). Melting range: 189-196° C.
¹³C-NMR (101 MHz, CDCl3, δ ppm): 25.8, 34.3, 35.4, 36.0, 37.7, 50.6, 66.4, 107.1, 110.3, 110.4, 110.5, 113.1, 119.6, 125.6, 125.7, 128.3, 132.0, 145.4, 155.0, 157.6, 157.8, 165.5, 167.6, 168.4, 171.0

28b) 2-((1-(2-(5-Fluoro-thiophen-2-yl)-6,6-dioxo-5,7-dihydro-thieno[3,4-d]pyrimidin-4-yl)-2,3-dihydro-1H-indol-4-yl)oxy)-N,N-dimethyl-acetamide m-Chloroperoxybenzoic acid (77%, 362 mg, 1.62 mmol) in dichloromethane (15 ml) was added under cooling with an ice bath within 15 min to a solution of the product of 28a) (233 mg, 0.51 mmol) in dichloromethane (20 ml) and the mixture was stirred for 17 h at ambient temperature. Further m-chloroperoxybenzoic acid (77%, 114 mg, 0.51 mmol) in dichloromethane (10 ml) was added and stirring was continued for 4 h. The mixture was quenched with saturated sodium hydrogen carbonate solution (50 ml) and stirred for 30 min. The organic phase was separated, washed with saturated sodium hydrogen carbonate solution (30 ml), dried over sodium sulfate and evaporated. The residue was purified by column chromatography [silica gel 60; ethyl acetate]. Yellow solid. Yield: 95 mg (38% of theory). Melting range: 241-244° C.

¹³C-NMR (101 MHz, DMSO-d6, δ ppm): 25.3, 34.9, 35.5, 50.4, 55.2, 56.2, 65.9, 107.1, 107.9, 110.0, 110.2, 119.5, 126.0, 127.9, 131.1, 131.2, 144.3, 154.5, 156.1, 157.6, 161.4, 165.4, 167.0, 168.3

Compound No. 2-08

2-((1-(2-(3-Chloro-4-methoxy-phenyl)-6,6-dioxo-5,7-dihydro-thieno[3,4-d]pyrimidin-4-yl)-2,3-dihydro-1H-indol-4-yl)oxy)-N,N-dimethyl-acetamide (Synthesis Example No. 29)

Prepared in an analogous manner to synthesis example No. 28 as yellow solid. Yield: 105 mg (46% of theory). Melting range: 260-262° C.
¹³C-NMR (101 MHz, DMSO-d6, δ ppm): 25.4, 34.9, 35.5, 50.6, 55.1, 56.3, 56.4, 65.9, 106.9, 108.2, 109.7, 112.7, 119.5, 121.2, 127.7, 127.8, 129.0, 130.2, 144.5, 154.7, 156.5, 156.6, 160.2, 161.7, 167.0

SYNTHESIS EXAMPLE NO. 30

2-((1-(2-(3-Fluoro-4-methoxy-phenyl)-6,6-dioxo-5,7-dihydro-thieno[3,4-d]pyrimidin-4-yl)-2,3-dihydro-1H-indol-4-yl)oxy)-N,N-dimethyl-acetamide (Compound No. 2-10)

30a) 2-(1-(2-(3-Fluoro-4-methoxyphenyl)-5,7-dihydrothieno[3,4-d]pyrimidin-4-yl)indolin-4-yloxy)-N,N-dimethylacetamide Beige solid. Yield: 307 mg (70% of theory). Melting range: 98-105° C.
¹³C-NMR (101 MHz, CDCl3, δ ppm): 25.8, 34.6, 35.6, 36.5, 38.3, 51.3, 56.2, 67.4, 105.8, 109.9, 110.0, 112.7, 112.9, 115.8, 116.0, 119.2, 124.4, 124.5, 128.3, 131.0, 145.7, 149.5, 149.6, 151.0, 153.4, 154.5, 158.0, 1671.7, 167.7, 171.6

30b) 2-((1-(2-(3-Fluoro-4-methoxy-phenyl)-6,6-dioxo-5,7-dihydro-thieno[3,4-d]pyrimidin-4-yl)-2,3-dihydro-1H-indol-4-yl)oxy)-N,N-dimethyl-acetamide Yellow solid. Yield: 108 mg (36% of theory). Melting range: 231-233° C.
¹³C-NMR (101 MHz, DMSO-d6, δ ppm): 25.4, 34.9, 35.5, 50.6, 55.1, 56.1, 56.4, 65.9, 106.9, 108.2, 109.7, 113.7, 114.6, 114.8, 119.5, 124.5, 127.8, 129.9, 144.5, 149.4, 149.5, 150.0, 152.4, 154.6, 156.5, 160.4, 161.6, 167.0

SYNTHESIS EXAMPLE NO. 31

2-((1-(2-(4-Methoxyphenyl)-6,6-dioxo-5,7-dihydro-thieno[3,4-d]pyrimidin-4-yl)-2,3-dihydro-1H-indol-4-yl)oxy)-N,N-dimethyl-acetamide (Compound No. 2-02)

31a) 2-(1-(2-(4-Methoxyphenyl)-5,7-dihydrothieno[3,4-d]pyrimidin-4-yl)indolin-4-yloxy)-N,N-dimethylacetamide Orange solid. Yield: 286 mg (58% of theory). Melting range: 195-200° C.

¹³C-NMR (101 MHz, DMSO-d6, δ ppm): 25.3, 33.7, 34.9, 35.5, 37.4, 50.3, 65.9, 106.2, 109.5, 112.2, 113.8, 118.9, 127.7, 129.2, 129.7, 145.3, 154.6, 157.5, 161.2, 167.1, 170.9

31b) 2-((1-(2-(4-Methoxyphenyl)-6,6-dioxo-5,7-dihydro-thieno[3,4-d]pyrimidin-4-yl)-2,3-dihydro-1H-indol-4-yl)oxy)-N,N-dimethyl-acetamide Yellow solid. Yield: 153 mg (40% of theory). Melting range: 225-232° C.
¹³C-NMR (101 MHz, DMSO-d6, δ ppm): 25.3, 34.9, 35.5, 50.5, 55.1, 55.2, 56.5, 65.9, 106.8, 107.7, 109.7, 113.9, 119.3, 127.8, 129.3, 129.4, 144.7, 154.6, 156.5, 161.4, 161.5, 161.6, 167.0

SYNTHESIS EXAMPLE NO. 32

2-((1-(2-(3-Chlorophenyl)-6,6-dioxo-5,7-dihydro-thieno[3,4-d]pyrimidin-4-yl)-2,3-dihydro-1H-indol-4-yl)oxy)-N,N-dimethyl-acetamide (Compound No. 2-06)

32a) 2-(1-(2-(3-Chlorophenyl)-5,7-dihydrothieno[3,4-d]pyrimidin-4-yl)indolin-4-yloxy)-N,N-dimethyl-acetamide Yellow solid. Yield: 369 mg (70% of theory). Melting range: 183-194° C.
¹³C-NMR (101 MHz, DMSO-d6, δ ppm): 25.4, 33.7, 34.9, 35.5, 37.4, 50.4, 65.9, 106.5, 109.5, 113.8, 119.2, 126.1, 127.2, 127.7, 130.1, 130.5, 133.4, 139.3, 145.1, 154.6, 157.6, 159.8, 167.1, 171.1

32b) 2-((1-(2-(3-Chlorophenyl)-6,6-dioxo-5,7-dihydro-thieno[3,4-d]pyrimidin-4-yl)-2,3-dihydro-1H-indol-4-yl)oxy)-N,N-dimethyl-acetamide Yellow solid. Yield: 153 mg (40% of theory). Melting range: 222-226° C.
¹³C-NMR (101 MHz, DMSO-d6, δ ppm): 25.4, 34.9, 35.5, 50.6, 55.1, 56.4, 65.9, 107.0, 109.1, 109.8, 119.6, 126.1, 127.3, 127.8, 130.5, 130.6, 133.4, 139.0, 144.4, 154.7, 156.6, 160.1, 161.7, 167.0

SYNTHESIS EXAMPLE NO. 33

2-((1-(2-(3,4-Difluoro-phenyl)-6,6-dioxo-5,7-dihydro-thieno[3,4-d]pyrimidin-4-yl)-2,3-dihydro-1H-indol-4-yl)oxy)-N,N-dimethyl-acetamide (Compound No. 2-12)

33a) 2-(1-(2-(3,4-Difluorophenyl)-5,7-dihydrothieno[3,4-d]pyrimidin-4-yl)indolin-4-yloxy)-N,N-dimethylacetamide Beige solid. Yield: 381 mg (72% of theory). Melting range: 198-200° C.
¹³C-NMR (101 MHz, DMSO-d6, δ ppm): 25.4, 33.6, 34.9, 35.5, 37.3, 50.4, 65.9, 106.5, 109.5, 113.6, 116.1, 116.3, 117.6, 117.8, 119.2, 124.6, 127.8, 134.9, 145.0, 148.2, 149.6, 149.8, 150.7, 152.1, 152.2, 154.6, 157.6, 159.2, 167.1, 171.0

33b) 2-((1-(2-(3,4-Difluoro-phenyl)-6,6-dioxo-5,7-dihydro-thieno[3,4-d]pyrimidin-4-yl)-2,3-dihydro-1H-indol-4-yl)oxy)-N,N-dimethyl-acetamide Yellow solid. Yield: 206 mg (53% of theory). Melting range: 212-217° C.

¹³C-NMR (101 MHz, DMSO-d6, δ ppm): 25.4, 34.9, 35.5, 50.7, 55.1, 56.4, 65.9, 107.0, 109.0, 109.7, 116.2, 116.4, 117.8, 117.9, 119.6, 124.7, 127.9, 134.5, 134.6, 144.4, 148.2, 148.3, 149.9, 150.0, 150.6, 150.7, 152.4, 152.5, 154.7, 156.6, 159.5, 161.7, 167.1

SYNTHESIS EXAMPLE NO. 34

2-((1-(2-(3-Fluorophenyl)-6,6-dioxo-5,7-dihydro-thieno[3,4-d]pyrimidin-4-yl)-2,3-dihydro-1H-indol-4-yl)oxy)-N,N-dimethyl-acetamide (Compound No. 2-04)

34a) 2-(1-(2-(3-Fluorophenyl)-5,7-dihydrothieno[3,4-d]pyrimidin-4-yl)indolin-4-yloxy)-N,N-dimethyl-acetamide Yellow solid. Yield: 321 mg (63% of theory). Melting range: 168-175° C.
¹³C-NMR (101 MHz, DMSO-d6, δ ppm): 25.4, 33.7, 34.9, 35.5, 37.4, 50.3, 65.9, 106.5, 109.5, 113.7, 113.8, 114.0, 117.1, 117.3, 119.1, 123.6, 127.7, 130.5, 130.6, 139.8, 139.9, 145.1, 154.6, 157.6, 160.0, 163.5, 167.1, 171.0

34b) 2-((1-(2-(3-Fluorophenyl)-6,6-dioxo-5,7-dihydro-thieno[3,4-d]pyrimidin-4-yl)-2,3-dihydro-1H-indol-4-yl)oxy)-N,N-dimethyl-acetamide Yellow solid. Yield: 149 mg (52% of theory). Melting range: 237-245° C.
¹³C-NMR (101 MHz, DMSO-d6, δ ppm): 25.4, 34.9, 35.5, 50.6, 55.1, 56.4, 65.9, 107.0, 109.1, 109.7, 113.9, 114.1, 117.5, 117.8, 119.5, 123.6, 127.8, 130.7, 139.5, 144.4, 154.6, 156.6, 160.3, 161.1, 161.7, 163.5, 167.0

SYNTHESIS EXAMPLE NO. 35

2-((1-(2-(5-Chlorothiophen-2-yl)-6-oxido-5,7-dihydrothieno[3,4-d]pyrimidin-4-yl)indolin-6-yl)oxy)-1-(pyrrolidin-1-yl)ethanone (Compound No. 2-116)

TBTU (0.125 g, 0.39 mmol) and N-methylmorpholine (0.07 mL, 0.64 mmol) were added at 0° C. to a solution of 2-((1-(2-(5-chlorothiophen-2-yl)-6-oxido-5,7-dihydrothieno[3,4-d]pyrimidin-4-yl)indolin-6-yl)oxy)acetic acid (0.15 g, 0.325 mmol) in DMF (2 mL). After stirring for 15 min, pyrrolidine (0.08 mL, 0.97 mmol) was introduced and the resulting mixture was stirred at room temperature for 16 h. The mixture was then poured onto cold water and extracted with dichloromethane (3×30 mL). The combined organic layers were washed with brine (1×50 mL), dried over sodium sulfate and evaporated to dryness. The residue was purified by flash column chromatography [methanol/dichloromethane=1:30]. Yellow solid. Yield: 0.04 g (24% of theory)

1H NMR (400 MHz, DMSO-d6, δ ppm): 7.75 (d, 1H, J=3.92 Hz), 7.65 (s, 1H), 7.23 (d, 1H, J=4.04 Hz), 7.16 (d, 1H, J=8.04 Hz), 6.58 (d, 1H, J=8.12 Hz), 4.72-4.68 (m, 3H), 4.5-4.46 (m, 2H), 4.36 (d, 1H, J=16.7 Hz), 4.29-4.28 (m, 1H), 3.98 (d, 1H, J=14.48 Hz), 3.44 (t, 2H, J=6.56 Hz), 3.28 (2H, obscured by H₂O peak), 3.17-3.06 (m, 2H), 1.86-1.83 (m, 2H), 1.76-1.71 (m, 2H).

The following compounds were prepared in an analogous manner

Compound No. 2-117

2-((1-(2-(5-Chlorothiophen-2-yl)-6-oxido-5,7-dihydrothieno[3,4-d]pyrimidin-4-yl)indolin-6-yl)oxy)-1-(4-methylpiperazin-1-yl)ethanone (Synthesis Example No. 36)

Yellow solid. Yield: 53 mg (22% of theory)
1H NMR (400 MHz, DMSO-d6, δ ppm): 7.74 (d, 1H, J=3.96 Hz), 7.64 (s, 1H), 7.24 (d, 1H, J=3.96 Hz), 7.16 (d, 1H, J=8.0 Hz), 6.58 (d, 1H, J=6.48 Hz), 4.81 (s, 2H), 4.70 (d, 1H, J=16.12 Hz), 4.35-4.5 (m, 4H), 3.98 (d, 1H, J=16.88 Hz), 3.42 (bs, 4H), 3.2-3.08 (m, 2H), 2.26 (bs, 2H), 2.21 (bs, 2H), 2.13 (s, 3H).

Compound No. 2-118

2-((1-(2-(5-Chlorothiophen-2-yl)-6-oxido-5,7-dihydrothieno[3,4-d]pyrimidin-4-yl)indolin-6-yl)oxy)-1-morpholinoethanone (Synthesis Example No. 37)

Yellow solid. Yield: 55 mg (24% of theory)
1H NMR (400 MHz, DMSO-d6, δ ppm): 7.74 (d, 1H, J=3.96 Hz), 7.66 (d, 1H, J=1.92 Hz), 7.24 (d, 1H, J=3.96 Hz), 7.17 (d, 1H, J=8.16 Hz), 6.6 (dd, 1H, J=2.2 and 8.28 Hz), 4.83 (s, 2H), 4.71 (d, 1H, J=16.4 Hz), 4.5-4.28 (m, 4H), 3.98 (d, 1H, J=16.96 Hz), 3.53 (bs, 4H), 3.44 (bs, 4H), 3.12-3.06 (m, 2H).

Compound No. 2-119

38: 2-((1-(2-(3-Fluoro-4-methoxyphenyl)-6-oxido-5,7-dihydrothieno[3,4-d]pyrimidin-4-yl)indolin-6-yl)oxy)-1-(pyrrolidin-1-yl)ethanone (Synthesis Example No. 38)

White solid. Yield: 0.12 g (34% of theory)
1H NMR (400 MHz, DMSO-d6, δ ppm): 8.18 (d, 1H, J=8.68 Hz), 8.06 (d, 1H, J=12.8 Hz), 7.61 (d, 1H, J=1.76 Hz), 7.32 (t, 1H, J=8.76 Hz), 7.16 (d, 1H, J=8.36 Hz), 6.57 (dd, 1H, J=2.08 and 8.16 Hz), 4.72-4.68 (m, 3H), 4.52-4.44 (m, 2H), 4.36-4.2 (m, 2H), 4.01 (d, 1H, J=16.88 Hz), 3.92 (s, 3H), 3.38 (t, 2H, J=6.6 Hz), 3.27 (t, 2H, J=6.88 Hz), 3.15-3.07 (m, 2H), 1.82-1.77 (m, 2H), 1.74-1.69 (m, 2H).

Compound No. 2-120

2-((1-(2-(5-Fluorothiophen-2-yl)-6-oxido-5,7-dihydrothieno[3,4-d]pyrimidin-4-yl)indolin-6-yl)oxy)-1-(pyrrolidin-1-yl)ethanone
(Synthesis Example No. 39)

Yellow solid. Yield: 75 mg (33% of theory)
1H NMR (400 MHz, DMSO-d6, δ ppm): 7.65-7.61 (m, 2H), 7.16 (d, 1H, J=8.24 Hz), 6.86 (d, 1H, J=3.96 Hz), 6.58 (dd, 1H, J=1.92 and 8.08 Hz), 4.72-4.68 (m, 3H), 4.49-4.37 (m, 2H), 4.34-4.25 (m, 2H), 3.97 (d, 1H, J=16.88 Hz), 3.44 (t, 2H, J=6.72 Hz), 3.17-3.06 (m, 2H), 1.86-1.83 (m, 2H), 1.76-1.72 (m, 2H).

Compound No. 2-121

2-((1-(2-(4-Methoxyphenyl)-6-oxido-5,7-dihydrothieno[3,4-d]pyrimidin-4-yl)indolin-6-yl)oxy)-1-(pyrrolidin-1-yl)ethanone (Synthesis Example No. 40)

White solid. Yield: 0.15 g (56% of theory)
1H NMR (400 MHz, DMSO-d6, δ ppm): 8.32 (d, 2H, J=8.76 Hz), 7.64 (d, 1H, J=1.88 Hz), 7.16 (d, 1H, J=8.12 Hz), 7.07 (d, 2H, J=8.76 Hz), 6.56 (dd, 1H, J=2.12 and 8.12 Hz), 4.72-4.68 (m, 3H), 4.51-4.43 (m, 2H), 4.35-4.27 (m, 2H), 4.0 (d, 1H, J=16.76 Hz), 3.83 (s, 3H), 3.38-3.34 (m, 2H), 3.27 (t, 2H, J=6.88 Hz), 3.15-3.07 (m, 2H), 1.8-1.75 (m, 2H), 1.73-1.68 (m, 2H).

Compound No. 2-122

1-(Azetidin-1-yl)-2-((1-(2-(5-chlorothiophen-2-yl)-6-oxido-5,7-dihydrothieno[3,4-d]pyrimidin-4-yl)indolin-6-yl)oxy)ethanone
(Synthesis Example No. 41)

EDCI (0.198 g, 1.03 mmol), HOBT (0.14 g, 1.03) and diisopropylethylamine (0.46 ml, 2.6 mmol) were added to a solution of 2-((1-(2-(5-chlorothiophen-2-yl)-6-oxido-5,7-dihydrothieno[3,4-d]pyrimidin-4-yl)indolin-6-yl)oxy)acetic acid (0.4 g, 0.865 mmol) in DMF (5 mL) and azetidine (0.054 g, 0.95 mmol). The resulting mixture was stirred at room temperature for 16 h, then diluted with dichloromethane (30 mL) and washed with saturated sodium hydrogen carbonate solution (10 ml) and water (2×10 mL). The organic layer was separated, dried over sodium sulfate and concentrated. The residue was purified by flash chromatography [dichloromethane with 0-3% methanol]. White solid. Yield: 165 mg (38% of theory)
1H NMR (400 MHz, DMSO-d6, δ ppm): 7.73 (d, 1H, J=4.0 Hz), 7.66 (d, 1H, J=2.16 Hz), 7.24-7.23 (m, 1H), 7.18 (d, 1H, J=8.2 Hz), 6.56 (dd, 1H, J=2.28 and 8.12 Hz), 4.71 (d, 1H, J=16.4 Hz), 4.59 (s, 2H), 4.53-4.4 (m, 2H), 4.37 (d, 1H, J=16.4 Hz), 4.19-4.25 (m, 3H), 3.98 (d, 1H, J=13.28 Hz), 3.89 (t, 2H, J=7.72 Hz), 3.14-3.07 (m, 2H), 2.22 (m, 2H, J=7.6 Hz).

SYNTHESIS EXAMPLE NO. 42

2-((1-(2-(5-Chlorothiophen-2-yl)-6,6-dioxido-5,7-dihydrothieno[3,4-d]pyrimidin-4-yl)indolin-6-yl)oxy)-N-ethylacetamide (Compound No. 2-55)

42a) Ethyl 2-((1-(2-(5-chlorothiophen-2-yl)-5,7-dihydrothieno[3,4-d]pyrimidin-4-yl)indolin-6-yl)oxy)acetate Prepared from 4-chloro-2-(5-chlorothiophen-2-yl)-5,7-dihydrothieno[3,4-d]pyrimidine (8.0 g, 27.77 mmol) and ethyl 2-(indolin-6-yloxy)acetate (6.13 g, 27.77 mmol) in an analogous manner to procedure 21c). Light yellow solid. Yield: 9.5 g (72% of theory)

42b) 2-((1-(2-(5-Chlorothiophen-2-yl)-5,7-dihydrothieno[3,4-d]pyrimidin-4-yl)indolin-6-yl)oxy)acetic acid The ethyl ester 42a) (9.2 g, 19.45 mmol) was reacted with 1 N sodium hydroxide solution (58.3 mL) for 1 h at 95° C.

in a blend of 1,4-dioxane and ethanol (1:1, 300 mL). Dark brown solid (9.0 g) that was used in the next step without further purification.

42c) 2-((1-(2-(5-chlorothiophen-2-yl)-6,6-dioxido-5,7-dihydrothieno[3,4-d]pyrimidin-4-yl)indolin-6-yl)oxy)acetic acid m-Chloroperoxybenzoic acid (1.73 g, 7.75 mmol) in anhydrous THF was added portion wise at 0° C. to a solution of 42b) (1.5 g, 3.37 mmol) in dry THF (600 mL). The mixture was stirred at room temperature for 16 h and then poured onto a saturated sodium sulphite solution (300 mL). After stirring for 30 min, the organic layer was separated, dried over sodium sulfate and concentrated. The residue was purified by flash column chromatography [dichloromethane/methanol=50:1 with 0.5% acetic acid]. Light yellow solid. Yield: 3.2 g (66% of theory)

42d) 2-((1-(2-(5-Chlorothiophen-2-yl)-6,6-dioxido-5,7-dihydrothieno[3,4-d]pyrimidin-4-yl)indolin-6-yl)oxy)-N-ethylacetamide Prepared from 42c) (0.20 g, 0.42 mmol) and ethyl amine (0.09 g, 0.84 mmol) in analogy to the procedure for synthesis example No. 35. Yellow solid. Yield: 0.04 g (19% of theory)

1H NMR (400 MHz, DMSO-d6, δ ppm): 8.02 (bt, 1H, J=8.0 Hz), 7.74-7.72 (m, 2H), 7.23-7.18 m, 2H), 6.65 (dd, 1H, J=2.2 and 8.2 Hz), 4.87 (s, 2H), 4.59 (s, 2H), 4.47 (s, 2H), 4.34 (t, 2H, J=8.16 Hz), 3.17-3.06 (m, 4H), 1.02 (t, 3H, J=7.2 Hz).

The following compounds were prepared in an analogous manner

Compound No. 2-123

2-((1-(2-(5-Chlorothiophen-2-yl)-6,6-dioxido-5,7-dihydrothieno[3,4-d]pyrimidin-4-yl)indolin-6-yl)oxy)-1-(4-methylpiperazin-1-yl) ethanone (Synthesis Example No. 43)

Light yellow solid. Yield: 85 mg (37% of theory)
1H NMR (400 MHz, DMSO-d6, δ ppm): 7.72 (d, 1H, J=3.96 Hz), 7.62 (d, 1H, J=2.0 Hz), 7.24 (d, 1H, J=3.96 Hz), 7.17 (d, 1H, J=8.24 Hz), 6.6 (dd, 1H, J=2.16 and 8.28 Hz), 4.86 (s, 2H), 4.81 (s, 2H), 4.59 (s, 2H), 4.33 (t, 2H, J=7.88 Hz), 3.41-3.4 (m, 4H), 3.07 (t, 2H, J=8.4 Hz), 2.25-2.20 (m, 4H), 2.13 (s, 3H).

Compound No. 2-54

2-((1-(2-(5-Chlorothiophen-2-yl)-6,6-dioxido-5,7-dihydrothieno[3,4-d]pyrimidin-4-yl)indolin-6-yl)oxy)-N-isopropylacetamide (Synthesis Example No. 44)

Yellow solid. Yield: 0.11 g (50% of theory)
1H NMR (400 MHz, DMSO-d6, δ ppm): 7.79-7.73 (m, 3H), 7.23-7.18 (m, 2H), 6.65 (dd, 1H, J=2.08 and 8.2 Hz), 4.87 (s, 2H), 4.59 (s, 2H), 4.45 (s, 2H), 4.35 (t, 2H, J=8.12 Hz), 3.96-3.91 (m, 1H), 3.08 (t, 2H, J=8.16 Hz), 1.08 (d, 6H, J=6.56 Hz).

Compound No. 2-56

2-((1-(2-(5-Chlorothiophen-2-yl)-6,6-dioxido-5,7-dihydrothieno[3,4-d]pyrimidin-4-yl)indolin-6-yl)oxy)-N-cyclopropyl-N-methylacetamide (Synthesis Example No. 45)

White solid. Yield: 85 mg (38% of theory)
1H NMR (400 MHz, DMSO-d6, δ ppm): 7.71 (d, 1H, J=3.96 Hz), 7.6 (s, 1H), 7.23 (d, 1H, J=3.88 Hz), 7.16 (d, 1H, J=8.24 Hz), 6.58 (dd, 1H, J=1.96 and 8.16 Hz), 4.93 (s, 2H), 4.86 (s, 2H), 4.59 (s, 2H), 4.33 (t, 2H, 8.08 Hz), 3.07 (t, 2H, J=8.28 Hz), 2.78-2.7 (m, 4H), 0.74-0.68 (m, 4H).

Compound No. 2-57

2-((1-(2-(5-Chlorothiophen-2-yl)-6,6-dioxido-5,7-dihydrothieno[3,4-d]pyrimidin-4-yl)indolin-6-yl)oxy)-N-(cyclopropylmethyl)-N-methylacetamide (Synthesis Example No. 46)

Light yellow solid. Yield: 65 mg (28% of theory)
1H NMR (400 MHz, DMSO-d6 at 100° C., δ ppm): 7.75 (d, 1H, J=4.0 Hz), 7.66 (d, 1H, J=4.0 Hz), 7.18-7.16 (m, 2H), 6.64 (dd, 1H, J=4.0 and 8.0 Hz), 4.77 (s, 4H), 4.5 (s, 2H), 4.34 (t, 2H, J=8.0 Hz), 3.22 (d, 2H, J=8.0 Hz), 3.11 (t, 2H, J=8.0 Hz), 3.0 (s, 3H), 0.96 (bs, 1H), 0.44 (d, 2H, J=4.0 Hz), 0.2 (d, 2H, J=4.0 Hz).

Compound No. 2-124

1-(Azetidin-1-yl)-2-((1-(2-(5-chlorothiophen-2-yl)-6,6-dioxido-5,7-dihydrothieno[3,4-d]pyrimidin-4-yl)indolin-6-yl)oxy)ethanone (Synthesis Example No. 47)

Light yellow solid. Yield: 95 mg (44% of theory)
1H NMR (400 MHz, DMSO-d6, δ ppm): 7.71 (d, 1H, J=3.92 Hz), 7.65 (s, 1H), 7.23 (d, 1H, J=3.92 Hz), 7.17 (d, 1H, J=8.2 Hz), 6.58 (d, 1H, J=8.0 Hz), 4.87 (s, 2H), 4.59 (s, 4H), 4.34 (t, 2H, J=8.08 Hz), 4.27 (t, 2H, J=7.6 Hz), 3.89 (t, 2H, J=7.56 Hz), 3.08 (t, 2H, J=8.08 Hz), 2.22 (m, 2H).

Compound No. 2-58

2-((1-(2-(5-Chlorothiophen-2-yl)-6,6-dioxido-5,7-dihydrothieno[3,4-d]pyrimidin-4-yl)indolin-6-yl)oxy)-N-methylacetamide (Synthesis Example No. 48)

Yellow solid. Yield: 85 mg (41% of theory)
1H NMR (400 MHz, DMSO-d6, δ ppm): 7.97 (d, 1H, 4.0 Hz), 7.73-7.71 (m, 2H), 7.23 (d, 1H, J=3.96 Hz), 7.19 (d, 1H, J=8.16 Hz), 6.65 (dd, 1H, J=1.96 and 8.16 Hz), 4.87 (s, 2H), 4.59 (s, 2H), 4.49 (s, 2H), 4.34 (t, 2H, J=8.16 Hz), 3.08 (t, 2H, J=8.16 Hz), 2.64 (d, 3H, J=4.64 Hz).

Compound No. 2-59

2-((1-(2-(5-Chlorothiophen-2-yl)-6,6-dioxido-5,7-dihydrothieno[3,4-d]pyrimidin-4-yl)indolin-6-yl)oxy)acetamide (Synthesis Example No. 49)

Light yellow solid. Yield: 55 mg (27% of theory)
1H NMR (400 MHz, DMSO-d6, δ ppm): 7.73 (d, 1H, J=3.96 Hz), 7.69 (s, 1H), 7.47 (bs, 1H), 7.37 (bs, 1H), 7.24 (d, 1H, J=3.96 Hz), 7.19 (d, 1H, J=8.08 Hz), 6.63 (dd, 1H, J=2.08 and 8.28 Hz), 4.87 (s, 2H), 4.59 (s, 2H), 4.45 (s, 2H), 4.34 (t, 2H, J=8.08 Hz), 3.08 (t, 2H, J=8.0 Hz).

Compound No. 2-60

2-((1-(2-(5-Chlorothiophen-2-yl)-6,6-dioxido-5,7-dihydrothieno[3,4-d]pyrimidin-4-yl)indolin-6-yl)oxy)-N-(oxetan-3-yl)acetamide (Synthesis Example No. 50)

Yellow solid. Yield: 90 mg (40% of theory)
1H NMR (400 MHz, DMSO-d6, δ ppm): 8.8 (d, 1H, J=6.52 Hz), 7.73 (d, 2H, J=3.76 Hz), 7.23-7.18 (m, 2H), 6.66 (1H, J=8.08 Hz), 4.90-4.85 (m, 3H), 4.68 (t, 2H, J=6.52 Hz), 4.59 (s, 2H), 4.52-4.48 (m, 4H), 4.35 (t, 2H, J=8.08 Hz), 3.08 (t, 2H, J=8.08 Hz).

Compound No. 2-61

2-((1-(2-(5-Chlorothiophen-2-yl)-6,6-dioxido-5,7-dihydrothieno[3,4-d]pyrimidin-4-yl)indolin-6-yl)oxy)-N-cyclopropylacetamide (Synthesis Example No. 51)

Light yellow solid. Yield: 0.07 g (37% of theory)
1H NMR (400 MHz, DMSO-d6, δ ppm): 8.06 (d, 1H, J=4.0 Hz), 7.72 (d, 1H, J=3.92 Hz), 7.7 (s, 1H), 7.23 (d, 1H, J=3.96 Hz), 7.18 (d, 1H, J=8.28 Hz), 6.61 (dd, 1H, J=2.08 and 8.16 Hz), 4.87 (s, 2H), 4.59 (s, 2H), 4.46 (s, 2H), 4.34 (t, 2H, J=8.16 Hz), 3.08 (t, 2H, J=8.36 Hz), 2.69-2.66 (m, 1H), 0.62-0.59 (m, 2H), 0.48-0.46 (m, 2H).

Compound No. 2-125

2-((1-(2-(5-Chlorothiophen-2-yl)-6,6-dioxido-5,7-dihydrothieno[3,4-d]pyrimidin-4-yl)indolin-6-yl)oxy)-1-morpholinoethanone (Synthesis Example No. 52)

White solid. Yield: 0.06 g (35% of theory)
1H NMR (400 MHz, DMSO-d6, δ ppm): 7.72 (d, 1H, J=3.8 Hz), 7.65 (s, 1H), 7.24 (d, 1H, J=3.88 Hz), 7.17 (d, 1H, J=8.12 Hz), 6.62 (d, 1H, J=8.32 Hz), 4.86 (s, 2H), 4.83 (s, 2H), 4.59 (s, 2H), 4.34 (t, 2H, J=8.12 Hz), 3.53 (bs, 4H), 3.44 (bs, 4H), 3.07 (t, 2H, J=7.88 Hz).

Compound No. 2-126

2-((1-(2-(5-Chlorothiophen-2-yl)-6,6-dioxido-5,7-dihydrothieno[3,4-d]pyrimidin-4-yl)indolin-6-yl)oxy)-1-(pyrrolidin-1-yl)ethanone (Synthesis Example No. 53)

White solid. Yield: 0.12 g (52% of theory)
1H NMR (400 MHz, DMSO-d6, δ ppm): 7.73 (s, 1H), 7.64 (s, 1H), 7.24 (s, 1H), 7.17 (d, 1H, J=7.36 Hz), 6.6 (d, 1H, J=6.8 Hz), 4.86 (s, 2H), 4.72 (s, 2H), 4.59 (s, 2H), 4.33 (t, 2H, J=7.3 Hz), 3.44 (t, 2H, J=7.16 Hz), 3.31 (2H, obscured by H₂O peak), 3.07 (t, 2H, J=7.38), 1.86-1.83 (m, 2H), 1.74-1.7 (m, 2H).

Compound No. 1-77

Example 54

Methyl 2-((1-(2-(5-chlorothiophen-2-yl)-6,6-dioxido-5,7-dihydrothieno[3,4-d]pyrimidin-4-yl)indolin-6-yl)oxy)acetate (Synthesis Example No. 54)

Refluxing of the carboxylic acid 42c) (0.20 g, 0.42 mmol) in methanol (8.0 mL) for 24 h and in the presence of concentrated sulphuric acid (0.2 mL) yielded the target compound. Light green solid. Yield: 80 mg (39% of theory)
1H NMR (400 MHz, DMSO-d6, δ ppm): 7.71 (d, 1H, J=3.92 Hz), 7.68 (d, 1H, J=1.6 Hz), 7.24 (d, 1H, J=3.88 Hz), 7.18 (d, 1H, J=8.08 Hz), 6.61 (dd, 1H, J=1.64 and 8.32 Hz), 4.87 (s, 2H), 4.83 (s, 2H), 4.59 (s, 2H), 4.34 (t, 2H, J=8.04 Hz), 3.66 (s, 3H), 3.08 (t, 2H, J=7.88 Hz).

Compound No. 2-52

2-((1-(2-(5-Chlorothiophen-2-yl)-6,6-dioxido-5,7-dihydrothieno[3,4-d]pyrimidin-4-yl)indolin-6-yl)oxy)-N-(2-hydroxyethyl)acetamide (Synthesis Example No. 55)

HATU (0.19 g, 0.50 mmol), diisopropylethylamine (0.3 mL, 1.67 mmol) and 2-amino ethanol (0.04 g, 0.67 mmol) were added to the carboxylic acid 42c) (0.20 g, 0.42 mmol) in DMF (2 mL). The resulting mixture was stirred at room temperature for 16 h, then poured onto ice-water (10 mL) and stirred for further 15 min A precipitate was filtered off, the filtrate was evaporated, and the residue purified by flash column chromatography [dichloromethane/methanol=1:50]. Light yellow solid. Yield: 0.09 g (40% of theory)
1H NMR (400 MHz, DMSO-d6, δ ppm): 7.95 (bs, 1H), 7.73 (d, 2H, J=2.6 Hz), 7.24-7.18 (m, 2H), 6.65 (d, 1H, J=6.28 Hz), 4.87 (s, 2H), 4.70 (t, 1H, J=5.36 Hz), 4.59 (s, 2H), 4.5 (s, 2H), 4.35 (t, 2H, J=7.96 Hz), 3.45-3.4 (m, 2H), 3.23-3.19 (m, 2H), 3.1-3.06 (m, 2H).

The following examples were obtained from 4-chloro-2-(5-chlorothiophen-2-yl)-5,7-dihydrothieno[3,4-d]pyrimidine in two chemical steps, comprising a Buchwald reaction with the appropriate indoline and an oxidation with m-chloroperoxybenzoic acid in analogy to the procedures 21c) and 42c), respectively.

Compound No. 3-1

2-((1-(2-(5-Chlorothiophen-2-yl)-6,6-dioxido-5,7-dihydrothieno[3,4-d]pyrimidin-4-yl)indolin-6-yl)oxy)acetonitrile (Synthesis Example No. 56)

Yellow solid. Yield: 0.10 g
1H NMR (400 MHz, DMSO-d6, δ ppm): 7.75 (d, 1H, J=1.8 Hz), 7.72 (d, 1H, J=4.0 Hz), 7.28-7.23 (m, 2H), 6.77 (dd, 1H, J=2.0 and 8.2 Hz), 5.18 (s, 2H), 4.87 (s, 2H), 4.6 (s, 2H), 4.36 (t, 2H, J=8.24 Hz), 3.1 (t, 2H, J=8.12 Hz).

Compound No. 3-2

2-(5-Chlorothiophen-2-yl)-4-(6-(2-methoxyethoxy)indolin-1-yl)-5,7-dihydrothieno[3,4-d]pyrimidine 6,6-dioxide (Synthesis Example No. 57)

White solid. Yield: 0.12 g
1H NMR (400 MHz, DMSO-d6, δ ppm): 7.71-7.7 (m, 2H), 7.23 (d, 1H, J=3.96 Hz), 7.17 (d, 1H, J=8.2 Hz), 6.61 (dd, 1H, J=2.04 and 8.24 Hz), 4.87 (s, 2H), 4.59 (s, 2H), 4.34 (t, 2H, J=8.12 Hz), 4.13 (t, 2H, J=4.52 Hz), 3.67 (t, 2H, J=4.52 Hz), 3.35 (s, 3H), 3.07 (t, 2H, J=8.12 Hz).

Compound No. 3-3

2-(5-Chlorothiophen-2-yl)-4-(6-(2-(dimethylamino)
ethoxy)indolin-1-yl)-5,7-dihydrothieno[3,4-d]py-
rimidine 6,6-dioxide (Synthesis Example No. 58)

Light yellow solid. Yield: 0.08 g
1H NMR (400 MHz, DMSO-d6, δ ppm): 7.72-7.71 (m, 2H), 7.22 (d, 1H, J=3.92 Hz), 7.17 (d, 1H, J=8.24 Hz), 6.62 (dd, 1H, J=2.0 and 8.2 Hz), 4.87 (s, 2H), 4.59 (s, 2H), 4.34 (t, 2H, J=8.2 Hz), 4.1 (t, 2H, J=5.56 Hz), 3.07 (t, 2H, J=8.12 Hz), 2.67 (bs, 2H), 2.26 (s, 6H).

Compound No. 2-45

2-((1-(2-(5-Chlorothiophen-2-yl)-6,6-dioxido-5,7-
dihydrothieno[3,4-d]pyrimidin-4-yl)indolin-6-yl)
oxy)-N,N-dimethylacetamide (Synthesis Example
No. 59)

Synthesized from 42b) in two chemical steps comprising an amide coupling with TBTU as coupling reagent followed by an oxidation with m-chloroperoxybenzoic acid. Light yellow solid. Yield: 35 mg
1H NMR (400 MHz DMSO-d6, δ ppm): 7.72 (d, 1H, J=3.84 Hz), 7.64 (s, 1H), 7.24 (d, 1H, J=3.84 Hz), 7.16 (d, 1H, J=8.08 Hz), 6.59 (d, 1H, J=7.92 Hz), 4.86 (s, 2H), 4.8 (s, 2H), 4.59 (s, 2H), 4.33 (t, 2H, J=8.16 Hz), 3.07 (t, 2H, J=8.24 Hz), 2.99 (s, 3H), 2.82 (s, 3H).

Compound No. 2-33

2-((1-(2-(3-Chloro-4-methoxyphenyl)-6,6-dioxido-5,
7-dihydrothieno[3,4-d]pyrimidin-4-yl)indolin-6-yl)
oxy)-N,N-dimethylacetamide (Synthesis Example
No. 60)

Obtained in an analogous manner as synthesis example No. 59. White solid. Yield: 35 mg
1H NMR (400 MHz, DMSO-d6, δ ppm): 8.32 (d, 1H, J=1.48 Hz), 8.28 (d, 1H, J=8.68 Hz), 7.64 (s, 1H), 7.30 (d, 1H, J=8.76 Hz), 7.17 (d, 1H, J=8.2 Hz), 6.60 (d, 1H, J=8.08 Hz), 4.85 (s, 2H), 4.78 (s, 2H), 4.61 (s, 2H), 4.34 (t, 2H, J=7.92 Hz), 3.94 (s, 3H), 3.08 (t, 2H, J=8.16 Hz), 2.92 (s, 3H), 2.79 (s, 3H).

SYNTHESIS EXAMPLE NO. 61

2-((1-(2-(5-Fluorothiophen-2-yl)-6,6-dioxido-5,7-
dihydrothieno[3,4-d]pyrimidin-4-yl)indolin-6-yl)
oxy)-N,N-dimethylacetamide (Compound No. 2-49)

61a) Ethyl 2-((1-(2-(5-fluorothiophen-2-yl)-5,7-
dihydrothieno[3,4-d]pyrimidin-4-yl)indolin-6-yl)
oxy)acetate Synthesized from 4-chloro-2-(5-fluorothiophen-2-yl)-5,7-dihydrothieno[3,4-d]pyrimidine (0.35 g, 1.28 mmol) and ethyl 2-(indolin-6-yloxy)acetate (0.28 g, 1.28 mmol) following the instructions of procedure 21c). White solid. Yield: 0.40 g (66% of theory) 61b) Ethyl 2-((1-(2-(5-fluorothiophen-2-yl)-6,6-dioxido-5,7-dihydrothieno[3,4-d]pyrimidin-4-yl)indolin-6-yl)oxy)acetate Oxidation of 61a) (0.50 g, 1.05 mmol) with m-chloroperbenzoic acid (0.61 g, 1.69 mmol) in analogy to procedure 28b). Light yellow solid. Yield: 0.30 g (58% of theory)

61c) 2-((1-(2-(5-Fluorothiophen-2-yl)-6,6-dioxido-5,
7-dihydrothieno[3,4-d]pyrimidin-4-yl)indolin-6-yl)
oxy)-N,N-dimethylacetamide Trimethylaluminium (2 M in toluene, 0.245 mL, 0.49 mmol) was added to a solution of dimethylamine (2M in THF, 0.245 mL, 0.49 mmol) in dichloromethane (3 mL) at 0° C. and the resulting mixture was stirred for 30 min Compound 61b) (0.06 g, 0.122 mmol) in dichloromethane (10 mL) was added and the mixture was heated at 70° C. for 2 min and then stirred for further 16 h at room temperature. The reaction mixture was quenched with saturated ammonium chloride solution (10 mL) and extracted with dichloromethane (3×20 mL). The combined organic layers were washed with water (30 mL) and brine (30 mL), dried over sodium sulphate and evaporated. The residue was purified first by flash column chromatography [methanol/dichloromethane=1:200] and then by preparative HPLC. White solid. Yield: 0.04 g (16% of theory)
1H NMR (400 MHz, DMSO-d6, δ ppm): 7.63-7.59 (m, 2H), 7.16 (d, 1H, J=8.0 Hz), 6.87 (d, 1H, J=3.68 Hz), 6.6 (d, 1H, J=8.12 Hz), 4.85 (s, 2H), 4.81 (s, 2H), 4.57 (s, 2H), 4.32 (t, 2H, J=8.0 Hz), 3.06 (t, 2H, J=7.92 Hz), 2.98 (s, 3H), 2.81 (s, 3H).

Compound No. 2-37

2-((1-(2-(3-Fluoro-4-methoxyphenyl)-6,6-dioxido-5,
7-dihydrothieno[3,4-d]pyrimidin-4-yl)indolin-6-yl)
oxy)-N,N-dimethylacetamide (Synthesis Example
No. 62)

The target compound was synthesized in an analogous manner as synthesis example No. 61. Yellow solid. Yield: 35 mg
1H NMR (400 MHz, DMSO-d6, δ ppm): 8.15 (d, 1H, J=8.52 Hz), 8.03 (d, 1H, J=12.48 Hz), 7.62 (s, 1H), 7.32 (t, 1H, J=8.76 Hz), 7.17 (d, 1H, J=8.24 Hz), 6.60 (d, 1H, J=8.0 Hz), 4.85 (s, 2H), 4.77 (s, 2H), 4.61 (s, 2H), 4.34 (t, 2H, J=8.2 Hz), 3.92 (s, 3H), 3.08 (t, 2H, J=8.04 Hz), 2.93 (s, 3H), 2.80 (s, 3H).

SYNTHESIS EXAMPLE NO. 63

2-((1-(6,6-Dioxido-2-(pyridin-4-yl)-5,7-dihydroth-
ieno[3,4-d]pyrimidin-4-yl)indolin-6-yl)oxy)-1-(pyr-
rolidin-1-yl)ethanone (Compound No. 2-130)

63a) 2-(Pyridin-4-yl)-5,7-dihydrothieno[3,4-d]py-
rimidin-4-ol

A mixture of isonicotinamidine (3.0 g, 19.03 mmol), 4-oxo-tetrahydro-thiophene-3-carboxylic acid methyl ester (4.6 g, 28.55 mmol) and diisoproylethylamine (16.36 mL, 95.15 mmol) in n-butanol (60 mL) was stirred at 120° C. for 16 h. After cooling to ambient temperature, a precipitate was filtered off and washed with ethyl acetate (2×50 mL) yielding the product as white solid. Yield: 2.0 g (45% of theory)

63b) 4-Chloro-2-(pyridin-4-yl)-5,7-dihydrothieno[3,
4-d]pyrimidine

A mixture of 2-(pyridin-4-yl)-5,7-dihydrothieno[3,4-d] pyrimidin-4-ol (2.1 g, 9.09 mmol) and phosphoroxychloride (17.7 mL, 189.07 mmol) was heated at 100° C. for 3 h. The reaction mixture was cooled to room temperature and excess phosphoroxychloride was removed under vacuum. The remnant was poured onto a mixture of ice water (75 mL) and saturated sodium hydrogen carbonate solution (100 mL), and was extracted with dichloromethane (3×100 mL). The combined organic layers were washed with brine (50 mL), dried over sodium sulphate and concentrated. The residue was purified by column chromatography [ethyl acetate/hexane=1:4]. White solid. Yield: 1.6 g (80% of theory)

63c) Ethyl 2-((1-(2-(pyridin-4-yl)-5,7-dihydrothieno[3,4-d]pyrimidin-4-yl)indolin-6-yl)oxy)acetate The target compound was synthesized from the pyrimidine chloride 63b) (1.5 g, 6.0 mmol) and ethyl 2-(indolin-6-yloxy)acetate (1.24 g, 6.0 mmol) in analogy to the procedure 21c). Light yellow solid. Yield: 1.5 g (57% of theory)

63d) 2-((1-(2-(Pyridin-4-yl)-5,7-dihydrothieno[3,4-d]pyrimidin-4-yl)indolin-6-yl)oxy)acetic acid The methyl ester 63c) (2.5 g, 5.95 mmol) was dissolved in ethanol (46 mL) and dioxane (46 mL), 1N sodium hydroxide solution (17.8 ml, 17.8 mmol) was added and the mixture was refluxed at 100° C. for 3 h. Light yellow solid. Yield: 0.7 g (29% of theory)

63e) 2-((1-(2-(Pyridin-4-yl)-5,7-dihydrothieno[3,4-d]pyrimidin-4-yl)indolin-6-yl)oxy)-1-(pyrrolidin-1-yl)ethanone HATU (0.95 g, 2.5 mmol), diisopropylethylamine (1.09 mL, 6.27 mmol) and pyrrolidine (0.21 mL, 2.51 mmol) were added to a solution of 63d) (0.85 g, 2.09 mmol) in DMF (8 mL). The resulting mixture was stirred at room temperature for 2 h, then diluted with water (30 mL) and extracted with dichloromethane (3×40 mL). The organic layers were dried over sodium sulphate and evaporated to dryness. The residue was purified by flash column chromatography [methanol/dichloromethane=1:50]. White solid. Yield: 0.6 g (62% of theory)

63f) 2-((1-(2-(3-Fluoro-4-methoxyphenyl)-6,6-dioxido-5,7-dihydrothieno[3,4-d]pyrimidin-4-yl)indolin-6-yl)oxy)-N,N-dimethylacetamide The thioether 63e) (0.3 g, 0.65 mmol) and MMPP (1.29 g, 2.61 mmol) in THF (700 mL) were stirred at room temperature for 4 h. The solvent was removed under vacuum, water (50 mL) was added to the remnant and the resulting mixture was extracted with dichloromethane (3×30 mL). The combined organic layers were washed with saturated sodium hydrogen carbonate solution, dried over sodium sulphate and concentrated. The residue was purified first by flash column chromatography [dichloromethane with 1-2.5% methanol] and finally by successive washing with methanol, diethyl ether, and pentane. Light yellow solid. Yield: 85 mg (27% of theory)
1H NMR (400 MHz, DMSO-d6, δ ppm): 8.76 (d, 2H, J=5.36 Hz), 8.17 (d, 2H, J=5.44 Hz), 7.67 (s, 1H), 7.19 (d, 1H, J=8.2 Hz), 6.63 (d, 1H, J=7.76 Hz), 4.91 (s, 2H), 4.7 (s, 2H), 4.67 (s, 2H), 4.37 (t, 2H, J=7.88 Hz), 3.35 (t, 2H, J=6.56 Hz), 3.26 (t, 2H, J=6.64 Hz), 3.09 (t, 2H, J=7.88 Hz), 1.81-1.68 (m, 4H).

The following compounds were obtained in an analogous manner

Compound No. 2-131

1-(Azetidin-1-yl)-2-((1-(6,6-dioxido-2-(pyridin-4-yl)-5,7-dihydrothieno[3,4-d]pyrimidin-4-yl)indolin-6-yl)oxy)ethanone (Synthesis Example No. 64)

Light yellow solid. Yield: 0.09 g
1H NMR (400 MHz, DMSO-d6, δ ppm): 8.75 (d, 2H, J=5.84 Hz), 8.18 (d, 2H, J=5.88 Hz), 7.7 (d, 1H, J=2.16 Hz), 7.2 (d, 1H, J=8.24 Hz), 6.6 (dd, 1H, J=8.28 and 2.32 Hz), 4.93 (s, 2H), 4.68 (s, 2H), 4.59 (s, 2H), 4.38 (t, 2H, J=8.2 Hz), 4.21 (t, 2H, J=7.64 Hz), 3.86 (t, 2H, J=7.64 Hz), 3.1 (t, 2H, J=8.12 Hz), 2.21-2.17 (m, 2H).

Compound No. 2-132

2-((1-(6,6-Dioxido-2-(pyridin-4-yl)-5,7-dihydrothieno[3,4-d]pyrimidin-4-yl)indolin-6-yl)oxy)-N,N-dimethylacetamide (Synthesis Example No. 65)

White solid. Yield: 0.09 g
1H NMR (400 MHz, DMSO-d6, δ ppm): 8.76 (d, 2H, J=5.28 Hz), 8.17 (d, 2H, J=5.72 Hz), 7.67 (d, 1H, J=2.0 Hz), 7.18 (d, 1H, J=8.16 Hz), 6.62 (dd, 1H, J=8.16 and 2.16 Hz), 4.91 (s, 2H), 4.78 (s, 2H), 4.67 (s, 2H), 4.37 (t, 2H, J=8.12 Hz), 3.09 (t, 2H, J=8.04 Hz), 2.91 (s, 3H), 2.79 (s, 3H).

Compound No. 2-133

2-((1-(6-Oxido-2-(pyridin-4-yl)-5,7-dihydrothieno[3,4-d]pyrimidin-4-yl)indolin-6-yl)oxy)-1-(pyrrolidin-1-yl)ethanone (Synthesis Example No. 66)

The thioether 63e) (0.15 g, 0.33 mmol) and m-chloroperoxybenzoic acid (77%, 58 mg, 0.26 mmol) in THF (300 mL) were stirred at room temperature for 1 h. The reaction mixture was diluted with brine (100 mL), and the aqueous phase was separated and extracted with THF (3×30 mL). The combined organic layers were washed with saturated sodium hydrogen carbonate solution, dried over sodium sulfate and evaporated to dryness. The residue was purified by flash column chromatography [methanol/dichloromethane=1:20]. White solid. Yield: 80 mg (51% of theory)
1H NMR (400 MHz, DMSO-d6, δ ppm): 8.76 (d, 2H, J=5.52 Hz), 8.21 (d, 2H, J=5.64 Hz), 7.66 (d, 1H, J=1.76 Hz), 7.18 (d, 1H, J=8.2 Hz), 6.59 (dd, 1H, J=8.16 and 2.04 Hz), 4.77-4.70 (m, 3H), 4.57-4.50 (m, 2H), 4.42-4.31 (m, 2H), 4.07 (d, 1H, J=16.92 Hz), 3.4-3.35 (m, 2H), 3.26 (t, 2H, J=6.8 Hz), 3.11-3.04 (m, 2H), 1.81-1.77 (m, 2H), 1.7-1.66 (m, 2H).

The following compounds were obtained in an analogous manner

Compound No. 2-134

1-(Azetidin-1-yl)-2-((1-(6-oxido-2-(pyridin-4-yl)-5,7-dihydrothieno[3,4-d]pyrimidin-4-yl)indolin-6-yl)oxy)ethanone (Synthesis Example No. 67)

White solid. Yield: 68 mg (60% of theory)
1H NMR (400 MHz, DMSO-d6, δ ppm): 8.75 (d, 2H, J=5.84 Hz), 8.21 (d, 2H, J=5.88 Hz), 7.7 (d, 1H, J=2.12 Hz), 7.2 (d, 1H, J=8.16 Hz), 6.59 (dd, 1H, J=8.16 and 2.28 Hz), 4.77 (d, 1H, J=16.44 Hz), 4.59 (s, 2H), 4.56-4.49 (m, 2H), 4.41 (d, 1H, J=16.48 Hz), 4.37-4.31 (m, 1H), 4.22 (t, 2H, J=7.72 Hz), 4.07 (d, 1H, J=16.9 Hz), 3.87 (t, 2H, J=7.76 Hz), 3.19-3.09 (m, 2H), 2.2 (p, 2H, J=7.52 Hz).

Compound No. 2-135

N,N-Dimethyl-2-((1-(6-oxido-2-(pyridin-4-yl)-5,7-dihydrothieno[3,4-d]pyrimidin-4-yl)indolin-6-yl)oxy)acetamide (Synthesis Example No. 68)

Light yellow solid. Yield: 80 mg
1H NMR (400 MHz, DMSO-d6, δ ppm): 8.76 (d, 2H, J=5.12 Hz), 8.22 (d, 2H, J=5.0 Hz), 7.66 (s, 1H), 7.18 (d, 1H, J=8.4 Hz), 6.6 (d, 1H, J=8.0 Hz), 4.73-4.8 (m, 3H), 4.58-4.47 (m, 2H), 4.39 (d, 1H, J=16.52 Hz), 4.34-4.29 (m, 1H), 4.07 (d, 1H, J=16.92 Hz), 3.2-3.05 (m, 2H), 2.92 (s, 3H), 2.79 (s, 3H).

Compound No. 2-136

2-((1-(6,6-Dioxido-2-(pyridin-3-yl)-5,7-dihydrothieno[3,4-d]pyrimidin-4-yl)indolin-6-yl)oxy)-N,N-dimethylacetamide (Synthesis Example No. 69)

Synthesized from 4-chloro-2-(pyridin-3-yl)-5,7-dihydrothieno[3,4-d]pyrimidine and 2-(indolin-6-yloxy)-N,N-dimethylacetamide in two chemical steps, namely a Buchwald-Hartwig reaction and an oxidation using MMPP as reagent. White solid. Yield: 0.08 g
1H NMR (400 MHz, DMSO-d6, δ ppm): 9.45 (s, 1H), 8.72 (d, 1H, J=6.2 Hz), 8.59 (d, 1H, J=8.0 Hz), 7.68 (s, 1H), 7.56 (dd, 1H, J=8.0 and 4.84 Hz), 7.18 (d, 1H, J=8.24 Hz), 6.6 (dd, 1H, J=8.2 and 2.0 Hz), 4.9 (s, 2H), 4.78 (s, 2H), 4.65 (s, 2H), 4.37 (t, 2H, J=8.08 Hz), 3.09 (t, 2H, J=7.96 Hz), 2.93 (s, 3H), 2.79 (s, 3H).

Compound No. 2-137

N,N-Dimethyl-2-((1-(6-oxido-2-(pyridin-3-yl)-5,7-dihydrothieno[3,4-d]pyrimidin-4-yl)indolin-6-yl)oxy)acetamide (Synthesis Example No. 70)

Tetrakis(triphenylphosphine)palladium(0) (20 mg, 0.017 mmol), 2M sodium carbonate solution (0.73 mL), 3-pyridylboronic acid (0.15 g, 0.92 mmol) and ethanol (6.5 mL) were added under an argon atmosphere to a solution of 2-((1-(2-chloro-6-oxido-5,7-dihydrothieno[3,4-d]pyrimidin-4-yl)indolin-6-yl)oxy)-N,N-dimethylacetamide (0.3 g, 0.74 mmol) in DME (6.5 mL). The resulting mixture was stirred at 95° C. for 4 h and then cooled to ambinet temperature. The solid material was filtered off, the filtrate was evaporated and the residue purified by column chromatography [neutral alumina; dichloromethane with 0.3% methanol]. Yellow solid. Yield: 0.08 g (24% of theory)
1H NMR (400 MHz, DMSO-d6, δ ppm): 9.49 (s, 1H), 8.71 (d, 1H, J=3.44 Hz), 8.64 (d, 1H, J=7.68 Hz), 7.67 (d, 1H, J=1.64 Hz), 7.56 (dd, 1H, J=7.7 and 4.8 Hz), 7.18 (d, 1H, J=8.12 Hz), 6.6-6.58 (m, 1H), 4.78-4.73 (m, 3H), 4.56-4.49 (m, 2H), 4.41-4.32 (m, 2H), 4.05 (d, 1H, J=16.96 Hz), 3.14-3.08 (m, 2H), 2.93 (s, 3H), 2.79 (s, 3H).

Compound No. 1-78

Methyl 2-(1-(2-(5-chlorothiophen-2-yl)-6,6-dioxido-5,7-dihydrothieno[3,4-d]pyrimidin-4-yl)indolin-5-yl)acetate (Synthesis Example No. 71)

Obtained from compound 21c) (0.3 g, 0.68 mmol) via oxidation with m-chloroperbenzoic acid (0.397 g, 1.78 mmol) following the instructions of procedure 28b). Yellow solid. Yield: 0.2 g (62% of theory)
1H NMR (400 MHz, DMSO-d6, δ ppm): 8.01 (d, 1H, J=8.16 Hz), 7.7 (d, 1H, J=4.0 Hz), 7.23 (d, 1H, J=3.96 Hz), 7.19-7.16 (m, 2H), 4.88 (s, 2H), 4.58 (s, 2H), 4.33 (t, 2H, J=8.2 Hz), 3.69 (s, 2H), 3.62 (s, 3H), 3.14 (t, 2H, J=8.16 Hz).

Compound No. 3-4

2-(1-(2-(5-Chlorothiophen-2-yl)-6,6-dioxido-5,7-dihydrothieno[3,4-d]pyrimidin-4-yl)indolin-5-yl)-N-ethylacetamide (Synthesis Example No. 72)

Prepared from synthesis example No. 23 in an analogous manner as described in procedure 35). Light yellow solid. Yield: 45 mg (22% of theory)
1H NMR (400 MHz, DMSO-d6, δ ppm): 7.98 (d, 2H, 7.52), 7.7 (d, 1H, J=4.0 Hz), 7.23 (d, 1H, J=4.0 Hz), 7.17-7.14 (m, 2H), 4.87 (s, 2H), 4.57 (s, 2H), 4.35 (t, 2H, J=8.24 Hz), 3.36 (s, 2H), 3.16-3.05 (m, 4H), 1.02 (t, 3H, J=8.0 Hz).

Compound No. 3-8

2-(1-(2-(5-Chlorothiophen-2-yl)-6,6-dioxido-5,7-dihydrothieno[3,4-d]pyrimidin-4-yl)indolin-5-yl)-N,N-dimethylacetamide (Synthesis Example No. 73)

Yellow solid. Yield: 0.05 g
1H NMR (400 MHz, DMSO-d6, δ ppm): 7.99 (d, 1H, J=8.4 Hz), 7.71 (d, 1H, J=4.0 Hz), 7.23 (d, 1H, J=4.0 Hz), 7.14-7.12 (m, 2H), 4.88 (s, 2H), 4.57 (s, 2H), 4.34 (t, 2H, J=8.0 Hz), 3.66 (s, 2H), 3.14 (t, 2H, J=8.0 Hz), 3.02 (s, 3H), 2.84 (s, 3H).

Compound No. 3-5

2-(1-(2-(5-Chlorothiophen-2-yl)-6,6-dioxido-5,7-dihydrothieno[3,4-d]pyrimidin-4-yl)indolin-5-yl)-N-methylacetamide (Synthesis Example No. 74)

Light yellow solid. Yield: 35 mg
1H NMR (400 MHz, DMSO-d6, δ ppm): 7.98 (d, 1H, J=8.4 Hz), 7.92 (bs, 1H), 7.70 (d, 1H, J=4.0 Hz), 7.23 (d, 1H, J=4.0 Hz), 7.17-7.14 (m, 2H), 4.88 (s, 2H), 4.57 (s, 2H), 4.33 (t, 2H, J=8.16 Hz), 3.36 (s, 2H), 3.14 (t, 2H, J=12 Hz), 2.57 (d, 3H, 4.11 Hz).

Compound No. 3-6

2-(1-(2-(5-Chlorothiophen-2-yl)-6,6-dioxido-5,7-dihydrothieno[3,4-d]pyrimidin-4-yl)indolin-5-yl)acetamide (Synthesis Example No. 75)

Prepared from example No. 23 (0.10 g, 0.216 mmol) in analogy to the procedure 41). Yellow solid. Yield: 0.05 g (50% of theory)
1H NMR (400 MHz, DMSO-d6, δ ppm): 7.98 (d, 1H, J=8.2 Hz), 7.71 (d, 1H, J=3.96 Hz), 7.43 (s, 1H), 7.23 (d, 1H, J=3.96), 7.18-7.15 (m, 1H), 6.86 (s, 1H), 4.88 (s, 2H), 4.57 (s, 2H), 4.32 (t, 2H, J=8.12 Hz), 3.35 (s, 2H), 3.14 (t, 2H, J=7.92 Hz).

SYNTHESIS EXAMPLE NO. 76

1-(Azetidin-1-yl)-2-((1-(2-(5-chlorothiophen-2-yl)-6,7-dihydro-5H-cyclopenta[d]pyrimidin-4-yl)indolin-6-yl)oxy)ethanone (Compound No. 2-127)

76a) Ethyl 2-((1-(2-(5-chlorothiophen-2-yl)-6,7-dihydro-5H-cyclopenta[d]pyrimidin-4-yl)indolin-6-yl)oxy)acetate Synthesis from 4-chloro-2-(5-chlorothiophen-2-yl)-6,7-dihydro-5H-cyclopenta[d]pyrimidine (3.66 g, 13.57 mmol) and ethyl 2-(indolin-6-yloxy)acetate (3.0 g, 13.57 mmol) in an analogous manner as described in procedure 21c). Dark yellow solid. Yield: 4.5 g (73% of theory)

76b) 2-((1-(2-(5-Chlorothiophen-2-yl)-6,7-dihydro-5H-cyclopenta[d]pyrimidin-4-yl)indolin-6-yl)oxy)acetic acid The ethyl ester 76a) (1.4 g, 3.08 mmol) was stirred for 1 h at 95° C. in a mixture of 1,4-dioxane (22 mL), ethanol (22 mL) and 1N sodium hydroxide solution (9.2 mL). Brown solid. Yield: 0.92 g (70% of theory)

76c) 1-(Azetidin-1-yl)-2-((1-(2-(5-chlorothiophen-2-yl)-6,7-dihydro-5H-cyclopenta[d]pyrimidin-4-yl)indolin-6-yl)oxy)ethanone The product of 76b) (0.15 g, 0.35 mmol) and azetidine (0.051 g, 0.88 mmol) were reacted in analogy to the procedure of synthesis example No. 35). White solid. Yield: 0.08 g (49% of theory)

1H NMR (400 MHz, DMSO-d6, δ ppm): 7.78 (d, 1H, J=2.21 Hz), 7.67 (d, 1H, J=4.0 Hz), 7.19 (d, 1H, J=4.0 Hz), 7.14 (d, 1H, J=8.16 Hz), 6.5 (dd, 1H, J=8.16 Hz and 2.2 Hz), 4.58 (s, 2H), 4.38 (t, 2H, J=8.34 Hz), 4.28 (t, 2H, J=7.64 Hz), 3.89 (t, 2H, J=7.64 Hz), 3.19 (t, 2H, J=7.16 Hz), 3.08 (t, 2H, J=8.36 Hz), 2.85 (t, 2H, J=7.8 Hz), 2.22 (m, 2H), 2.03 (m, 2H).

The following compounds were obtained in an analogous manner

Compound No. 2-42

2-((1-(2-(5-Chlorothiophen-2-yl)-6,7-dihydro-5H-cyclopenta[d]pyrimidin-4-yl)indolin-6-yl)oxy)-N,N-dimethylacetamide (Synthesis Example No. 77)

White solid. Yield: 55 mg
1H NMR (400 MHz, DMSO-d6, δ ppm): 7.77 (d, 1H, J=2.24 Hz), 7.67 (d, 1H, J=3.92 Hz), 7.2 (d, 1H, J=3.92 Hz), 7.12 (d, 1H, J=8 Hz), 6.52 (dd, 1H, J=8 Hz and 2.28 Hz), 4.79 (s, 2H), 4.37 (t, 2H, J=8.44 Hz), 3.19 (t, 2H, J=8.0 Hz), 3.07 (t, 2H, J=8.0 Hz), 2.96 (s, 3H), 2.87-2.82 (m, 5H), 2.01 (p, 2H, J=7.44 Hz).

Compound No. 2-128

2-((1-(2-(5-Chlorothiophen-2-yl)-6,7-dihydro-5H-cyclopenta[d]pyrimidin-4-yl)indolin-6-yl)oxy)-1-morpholinoethanone (Synthesis Example No. 78)

Yellow solid. Yield: 75 mg (40% of theory)
1H NMR (400 MHz, DMSO-d6, δ ppm): 7.77 (d, 1H, J=2.21 Hz), 7.68 (d, 1H, J=3.92 Hz), 7.20 (d, 1H, J=3.88 Hz), 7.13 (d, 1H, J=8.24 Hz), 6.51 (dd, 1H, J=8.2 Hz and 2.2 Hz), 4.81 (s, 2H), 4.37 (t, 2H, J=8.32 Hz), 3.54-3.3 (m, 8H), 3.19 (t, 2H, J=7.32 Hz), 3.07 (t, 2H, J=8.16 Hz), 2.85 (t, 3H, J=7.8 Hz), 2.01 (m, 2H).

Compound No. 2-129

2-((1-(2-(5-Chlorothiophen-2-yl)-6,7-dihydro-5H-cyclopenta[d]pyrimidin-4-yl)indolin-6-yl)oxy)-1-(4-methylpiperazin-1-yl)ethanone (Synthesis Example No. 79)

Yellow solid. Yield: 0.06 g (39% of theory)
1H NMR (400 MHz, DMSO-d6, δ ppm): 7.75 (d, 1H, J=2.04 Hz), 7.68 (d, 1H, J=3.92 Hz), 7.20 (d, 1H, J=3.92 Hz), 7.11 (d, 1H, J=8.2 Hz), 6.52 (d, 1H, J=8.2 Hz and 2.2 Hz), 4.79 (s, 2H), 4.37 (t, 2H, J=8.36 Hz), 3.42 (bs, 4H), 3.19 (t, 2H, J=7.36 Hz), 3.07 (t, 2H, J=8.2 Hz), 2.85 (t, 2H, J=7.8 Hz), 2.26-2.20 (m, 4H), 2.13 (s, 3H), 2.01 (m, 2H).

Compound No. 2-64

2-((1-(2-(5-Chlorothiophen-2-yl)-6,7-dihydro-5H-cyclopenta[d]pyrimidin-4-yl)indolin-6-yl)oxy)-N-cyclopropyl-N-methylacetamide (Synthesis Example No. 80)

White solid. Yield: 0.06 g (18% of theory)
1H NMR (400 MHz, DMSO-d6, δ ppm): 7.74 (s, 1H), 7.67 (d, 1H, J=3.76 Hz), 7.18 (d, 1H, J=3.52 Hz), 7.12 (d, 1H, J=8.08 Hz), 6.50 (d, 1H, J=7.88 Hz), 4.91 (s, 2H), 4.36 (t, 2H, J=8.12 Hz), 3.19 (t, 2H, J=7.0 Hz), 3.08 (t, 2H, J=8.08 Hz), 2.86 (t, 2H, J=7.74 Hz), 2.79 (bs, 4H), 2.01 (p, 2H, J=7.16 Hz), 0.75-0.65 (m, 4H).

Compound No. 2-65

2-((1-(2-(5-Chlorothiophen-2-yl)-6,7-dihydro-5H-cyclopenta[d]pyrimidin-4-yl)indolin-6-yl)oxy)-N-(oxetan-3-yl)acetamide (Synthesis Example No. 81)

Yellowish solid. Yield: 75 mg (33% of theory)
1H NMR (400 MHz, DMSO-d6, δ ppm): 8.78 (d, 1H, J=4.52 Hz), 7.87 (s, 1H), 7.69 (d, 1H, J=3.6 Hz), 7.19-7.14 (m, 2H), 6.58 (d, 1H, J=8.2 Hz), 4.86 (m, 1H), 4.68 (t, 2H, J=7.12 Hz), 4.52-4.49 (m, 4H), 4.39 (t, 2H, J=8.08 Hz), 3.20 (t, 2H, J=7.32 Hz), 3.09 (t, 2H, J=8.36 Hz), 2.86 (t, 2H, J=7.76 Hz), 2.01 (m, 2H).

Compound No. 2-66

2-((1-(2-(5-Chlorothiophen-2-yl)-6,7-dihydro-5H-cyclopenta[d]pyrimidin-4-yl)indolin-6-yl)oxy)-N-isopropylacetamide (Synthesis Example No. 82)

White solid. Yield: 0.07 g (21% of theory)
1H NMR (400 MHz, DMSO-d6, δ ppm): 7.86 (d, 1H, J=1.84 Hz), 7.77 (d, 1H, J=8.04 Hz), 7.68 (d, 1H, J=3.92 Hz), 7.17 (d, 1H, J=3.88 Hz), 7.14 (d, 1H, J=8.2 Hz), 6.56 (dd, 1H, J=8.12 Hz and 2.12 Hz), 4.44 (s, 2H), 4.39 (t, 2H, J=8.44 Hz), 4.0-3.9 (m, 1H), 3.20 (t, 2H, J=7.16 Hz), 3.08 (t, 2H, J=8.44 Hz), 2.86 (t, 2H, J=7.76 Hz), 2.01 (m, 2H), 1.07 (d, 6H, J=6.6 Hz).

Compound No. 2-67

2-((1-(2-(5-Chlorothiophen-2-yl)-6,7-dihydro-5H-cyclopenta[d]pyrimidin-4-yl)indolin-6-yl)oxy)-N-(cyclopropylmethyl)-N-methylacetamide (Synthesis Example No. 83)

White solid. Yield: 0.05 g (29% of theory)
1H NMR (400 MHz, DMSO-d6, 100° C., δ ppm): 7.78 (s, 1H), 7.69 (d, 1H, J=4.0 Hz), 7.15-7.11 (m, 2H), 6.56 (d, 1H, J=4.0 Hz), 4.76 (s, 2H), 4.37 (t, 2H, J=8.0 Hz), 3.24-3.09 (m, 7H), 3.01 (s, 2H), 2.88 (t, 2H, J=8.0 Hz), 2.06 (m, 2H). 1.0-0.85 (m, 1H), 0.46-0.39 (m, 2H), 0.3-0.2 (m, 2H).

Compound No. 2-68

2-((1-(2-(5-Chlorothiophen-2-yl)-6,7-dihydro-5H-cyclopenta[d]pyrimidin-4-yl)indolin-6-yl)oxy)-N-ethylacetamide (Synthesis Example No. 84)

Synthesized in an analogous manner as described for synthesis example No. 41. Light greenish solid. Yield: 0.06 g (43% of theory)
1H NMR (400 MHz, DMSO-d6, δ ppm): 8.01 (t, 1H, J=4.0 Hz), 7.84 (d, 1H, J=2.16 Hz), 7.68 (d, 1H, J=3.92 Hz), 7.17 (d, 1H, J=3.96 Hz), 7.14 (d, 1H, J=8.12 Hz), 6.57 (dd, 1H, J=8.16 and 2.32 Hz), 4.46 (s, 2H), 4.38 (t, 2H, J=8.32 Hz), 3.21-3.06 (m, 6H), 2.85 (t, 2H, J=7.8 Hz), 2.01 (m, 2H), 1.03 (t, 3H, J=7.2 Hz).

Compound No. 2-69

2-((1-(2-(5-Chlorothiophen-2-yl)-6,7-dihydro-5H-cyclopenta[d]pyrimidin-4-yl)indolin-6-yl)oxy)-N-(2-hydroxyethyl)acetamide (Synthesis Example No. 85)

The target compound was prepared in analogy to the procedure of synthesis example No. 55. White solid. Yield: 45 mg (27% of theory)
1H NMR (400 MHz, DMSO-d6, δ ppm): 7.92 (t, 1H, J=4.1 Hz), 7.86 (d, 1H, J=1.89 Hz), 7.68 (d, 1H, J=3.88 Hz), 7.18 (d, 1H, J=3.92 Hz), 7.14 (d, 1H, J=8.08 Hz), 6.58 (dd, 1H, J=8.0 Hz, and 1.88 Hz), 4.70 (t, 1H, J=5.48 Hz), 4.49 (s, 2H), 4.38 (t, 2H, J=8.44 Hz), 3.45-3.40 (m, 2H), 3.23-3.18 (m, 4H), 3.08 (t, 2H, J=8.1 Hz), 2.86 (t, 2H, J=7.76 Hz), 1.99 (m, 2H).

Compound No. 2-70

2-((1-(2-(5-Chlorothiophen-2-yl)-6,7-dihydro-5H-cyclopenta[d]pyrimidin-4-yl)indolin-6-yl)oxy)-N-methylacetamide (Synthesis Example No. 86)

Oxalyl chloride (0.06 mL, 0.7 mmol) and a catalytic amount of DMF (0.03 mL) were added drop wise at 0° C. to a solution of the acetic acid 76b) (0.15 g, 0.35 mmol) in dichloromethane (5.0 mL). The resulting mixture was stirred at room temperature for 3 h. The solvent was then evaporated, the residue was re-dissolved in dichloromethane (5.0 mL) and dimethyl amine (2M in THF, 0.52 mL, 1.05 mmol) was added at 0° C. After stirring for 16 h at room temperature, the mixture was concentrated and the remnant purified first by flash column chromatography [dichloromethane/methanol=50:1] and then by preparative TLC. Yellow solid. Yield: 0.05 g (32% of theory)

1H NMR (400 MHz, DMSO-d6, δ ppm): 7.95 (bs, 1H), 7.83 (d, 1H, J=1.8 Hz), 7.68 (d, 1H, J=3.88 Hz), 7.18 (d, 1H, J=3.96 Hz), 7.14 (d, 1H, J=8.2 Hz), 6.57 (dd, 1H, J=7.96 Hz and 2.04 Hz), 4.48 (s, 2H), 4.38 (t, 2H, J=8.28 Hz), 3.20 (t, 2H, J=7.28 Hz), 3.08 (t, 2H, J=8.16 Hz), 2.86 (t, 2H, J=7.8 Hz), 2.65 (d, 3H, J=4.6 Hz), 2.01 (m, 2H).

Compound No. 2-71

2-((1-(2-(5-Chlorothiophen-2-yl)-6,7-dihydro-5H-cyclopenta[d]pyrimidin-4-yl)indolin-6-yl)oxy)acetamide (Synthesis Example No. 87)

Amide cooling with acetic acid 76b) as substrate and EDC1 and ammonium 1H-1,2,3-benzotriazol-1-olate (HOBT.NH3) as coupling reagents in analogy to the procedure of synthesis example No. 41. White solid. Yield: 0.09 g
1H NMR (400 MHz, DMSO-d6, δ ppm): 7.81 (d, 1H, J=1.84 Hz), 7.68 (d, 1H, J=3.92 Hz), 7.44 (s, 1H), 7.38 (s, 1H), 7.19 (d, 1H, J=3.92 Hz), 7.14 (d, 1H, J=8.24 Hz), 6.55 (dd, J=8.12 and 2.0 Hz), 4.44 (s, 2H), 4.38 (t, 2H, J=8.24 Hz), 3.19 (t, 2H, J=7.4 Hz), 3.08 (t, 2H, J=8.28 Hz), 2.85 (t, 2H, J=7.68 Hz), 2.01 (m, 2H).

Compound No. 1-79

Methyl 2-((1-(2-(5-chlorothiophen-2-yl)-6,7-dihydro-5H-cyclopenta[d]pyrimidin-4-yl)indolin-6-yl)oxy)acetate (Synthesis Example No. 88)

Synthesized from the acetic acid 76b) (0.15 g, 0.35 mmol) in analogy to the procedure of synthesis example No. 54. White solid. Yield: 0.06 g (24% of theory)
1H NMR (400 MHz, DMSO-d6, δ ppm): 7.82 (d, 1H, J=2.08 Hz), 7.66 (d, 1H, J=3.92 Hz), 7.19 (d, 1H, J=3.92 Hz), 7.13 (d, 1H, J=8.16 Hz), 6.52 (dd, 1H, J=8.12 and 2.2 Hz), 4.82 (s, 2H), 4.38 (t, 2H, J=8.44 Hz), 3.66 (s, 3H), 3.20 (t, 2H, J=7.32 Hz), 3.08 (t, 2H, J=8.4 Hz), 2.85 (t, 2H, J=7.84 Hz), 2.01 (m, 2H).

SYNTHESIS EXAMPLE NO. 89

2-((1-(2-(5-Chlorothiophen-2-yl)-6-oxido-5,7-dihydrothieno[3,4-d]pyrimidin-4-yl)-1H-indazol-6-yl)oxy)-N,N-dimethylacetamide (Compound No. 2-72)

89a) 2-((1-(2-(5-Chlorothiophen-2-yl)-5,7-dihydrothieno[3,4-d]pyrimidin-4-yl)-1H-indazol-6-yl)oxy)-N,N-dimethylacetamide Prepared from 4-chloro-2-(5-chlorothiophen-2-yl)-5,7-dihydrothieno[3,4-d]pyrimidine (0.25 g, 0.86 mmol) and 2-((1H-indazol-6-yl)oxy)-N,N-dimethylacetamide (0.2 g, 0.86 mmol; synthesized from 1H-indazol-6-ol and 2-chloro-N,N-dimethylacetamide) in an analogous manner as described in procedure 21c). Yellow solid. Yield: 0.15 g (37% of theory)

89b) 2-((1-(2-(5-Chlorothiophen-2-yl)-6-oxido-5,7-dihydrothieno[3,4-d]pyrimidin-4-yl)-1H-indazol-6-yl)oxy)-N,N-dimethylacetamide m-Chloroperoxybenzoic acid (77%, 50 mg, 0.225 mmol) in THF (5 mL) was added under cooling with an ice bath to a solution of 89a) (140 mg, 0.3 mmol) in THF. The resulting mixture was stirred for 20 min at room temperature and then diluted with brine (10 mL). The aqueous phase was extracted with THF (3×10 mL) and the combined organic layers were dried over sodium sulfate and evaporated. The residue was purified by column chromatography [dichloromethane/methanol=50:1]. Yellow solid. Yield: 67 mg (44% of theory)

1H NMR (400 MHz, DMSO-d6, δ ppm): 8.53 (s, 1H), 8.2 (s, 1H), 7.95 (s, 1H), 7.84 (d, 1H, J=8.4 Hz), 7.32 (d, 1H, J=3.3 Hz), 7.1 (d, 1H, J=8.8 Hz), 5.07 (s, 2H), 4.83 (d, 1H, J=17.6 Hz), 4.63 (d, 2H, J=14 Hz), 4.17 (d, 1H, J=17.2 Hz), 3.06 (s, 3H), 2.86 (s, 3H).

Compound No. 2-73

2-((1-(2-(5-Chlorothiophen-2-yl)-6-oxido-5,7-dihydrothieno[3,4-d]pyrimidin-4-yl)-1H-indol-6-yl)oxy)-N,N-dimethylacetamide (Synthesis Example No. 90)

The target compound was synthesized from 4-chloro-2-(5-chlorothiophen-2-yl)-5,7-dihydrothieno[3,4-d]pyrimidine and 2-((1H-indol-6-yl)oxy)-N,N-dimethylacetamide in an analogous manner as described for synthesis example No. 89. Yellow solid. Yield: 145 mg (44% of theory) 1H NMR (400 MHz, DMSO-d6, δ ppm): 7.92 (d, 1H, J=3.9 Hz), 7.82 (d, 1H, J=1.7 Hz), 7.69 (d, 1H, J=3.5 Hz), 7.58 (d, 1H, J=8.6 Hz), 7.31 (d, 1H, J=3.9 Hz), 6.94 (dd, 1H, J=2.1 and 8.6 Hz), 6.81 (d, 1H, d, J=3.4 Hz), 4.89-4.86 (m, 3H), 4.71 (d, 1H, J=16 Hz), 4.22-4.16 (m, 2H), 2.96 (s, 3H), 2.81 (s, 3H).

Compound No. 2-74

2-((1-(2-(5-Chlorothiophen-2-yl)-6-oxido-5,7-dihydrothieno[3,4-d]pyrimidin-4-yl)-1H-benzo[d]imidazol-6-yl)oxy)-N,N-dimethylacetamide (Synthesis Example No. 91)

Compound No. 2-75

2-((1-(2-(5-Chlorothiophen-2-yl)-6-oxido-5,7-dihydrothieno[3,4-d]pyrimidin-4-yl)-1H-benzo[d]imidazol-5-yl)oxy)-N,N-dimethylacetamide (Synthesis Example No. 92)

Compounds 2-74 and 2-75 were synthesized from 4-chloro-2-(5-chlorothiophen-2-yl)-5,7-dihydrothieno[3,4-d]pyrimidine (1.4 g, 5.0 mmol) and 2-((1H-benzo[d]imidazol-6-yl)oxy)-N,N-dimethylacetamide (1.27 g, 5.0 mmol) in the two chemical steps as described for synthesis example No. 76). The two obtained regioisomers were separated after the last step by means of SFC (supercritical fluid chromatography) and the structures were assigned based on their activity in the primary assays.

Compound 2-74: (peak 1): White solid. Yield: 127 mg (18% of theory)

1H NMR (400 MHz, DMSO-d6, δ ppm): 8.68 (s, 1H), 7.95 (d, 1H, J=4 Hz), 7.73-7.7 (m, 2H), 7.32 (d, 1H, J=4 Hz), 7.05 (dd, 1H, J=2.1 and 8.9 Hz), 4.91-4.83 (m, 3H), 4.78 (d, 1H, J=17.1 Hz), 4.37 (d, 1H, J=16.8 Hz), 4.27 (d, 1H, J=17.1 Hz), 2.98 (s, 3H), 2.83 (s, 3H).

Compound No. 2-75: (peak 2): White solid. Yield: 95 mg (14% of theory)

1H NMR (400 MHz, DMSO-d6, δ ppm): 8.77 (s, 1H), 8.15 (d, 1H, J=8.9 Hz), 7.93 (d, 1H, J=3.7 Hz), 7.35-7.33 (m, 2H), 7.15 (d, 1H, J=8.8 Hz), 4.95-4.9 (m, 3H), 4.77 (d, 1H, J=17.16 Hz), 4.42 (d, 1H, J=16.7 Hz), 4.26 (d, 1H, J=17.2 Hz), 3.04 (s, 3H), 2.87 (s, 3H).

Compound 2-76

2-((3-(2-(5-Chlorothiophen-2-yl)-6-oxido-5,7-dihydrothieno[3,4-d]pyrimidin-4-yl)-2-oxo-2,3-dihydrobenzo[d]oxazol-5-yl)oxy)-N,N-dimethylacetamide (Synthesis Example No. 93)

Synthesized in an analogous manner to synthesis example Nos. 14 and 95. White solid. Yield: 40 mg 1H NMR (400 MHz, DMSO-d6, δ ppm): 7.89 (s, 1H), 7.41 (d, 1H, J=8.6 Hz), 7.32 (s, 2H), 6.87 (d, 1H, J=7.6 Hz), 4.86 (s, 2H), 4.77 (d, 1H, J=16.5 Hz), 4.5 (q, 2H, J=17.3 Hz), 4.22 (d, 1H, J=17.7 Hz), 2.93 (s, 3H), 2.81 (s, 3H).

Compound No. 1-71

2-(1-(2-(5-Chlorothiophen-2-yl)-6,7-dihydro-5H-cyclopenta[d]pyrimidin-4-yl)-1H-indol-5-yl)acetic acid (Synthesis Example No. 94)

Synthesized in two steps from 4-chloro-2-(5-chlorothiophen-2-yl)-6,7-dihydro-5H-cyclopenta[d]pyrimidine and methyl 2-(1H-indol-5-yl)acetate. White solid. Yield: 165 mg 1H NMR (400 MHz, DMSO-d6, δ ppm): 12.4 (bs, 1H), 8.32 (d, 1H, J=8.52 Hz), 7.85 (d, 1H, J=3.48 Hz), 7.81 (d, 1H, J=3.92 Hz), 7.55 (s, 1H), 7.25-7.23 (m, 2H), 6.8 (d, 1H, J=3.4 Hz), 3.65 (s, 2H), 3.19 (t, 2H, J=7.2 Hz), 3.03 (t, 2H, J=7.64 Hz), 2.14 (m, 2H).

Compound No. 1-68

3-(2-(5-Chlorothiophen-2-yl)-6,7-dihydro-5H-cyclopenta[d]pyrimidin-4-yl)-2-oxo-2,3-dihydrobenzo[d]oxazole-6-carboxylic acid
(Synthesis Example No. 95)

Synthesized from 4-chloro-2-(5-chlorothiophen-2-yl)-6,7-dihydro-5H-cyclopenta[d]pyrimidine and methyl 4-amino-3-methoxybenzoate analogously to synthesis example No. 14 in three steps comprising a Buchwald-Hartwig reaction, a demethylation with BBr3 in dichloromethane and a cyclisation with CDI. White solid. Yield: 45 mg 1H NMR (400 MHz, DMSO-d6, δ ppm): 7.94-7.90 (m, 2H), 7.8 (d, 1H, J=3.96 Hz), 7.64 (d, 1H, J=8.28 Hz), 7.25 (d, 1H, J=3.92 Hz), 3.11-3.05 (m, 4H), 2.1 (m, 2H).

Compound No. 1-74

1-(2-(5-Chlorothiophen-2-yl)-6,7-dihydro-5H-cyclopenta[d]pyrimidin-4-yl)-1H-benzo[d]imidazole-6-carboxylic acid (Synthesis Example No. 96)

Compound No. 1-63

1-(2-(5-Chlorothiophen-2-yl)-6,7-dihydro-5H-cyclopenta[d]pyrimidin-4-yl)-1H-benzo[d]imidazole-5-carboxylic acid (Synthesis Example No. 97)

Prepared from 4-chloro-2-(5-chlorothiophen-2-yl)-6,7-dihydro-5H-cyclopenta[d]pyrimidine and methyl 1H-benzo[d]imidazole-5-carboxylate in two steps, namely a Buchwald-Hartwig reaction and an ester saponification with lithium hydroxide in THF/water. The two regioisomers obtained were separated after the last step by means of HPLC. The structures were assigned based on the compounds activity in the primary assays.

Example 96 (peak 1): White solid. Yield: 28 mg
1H NMR (400 MHz, DMSO-d6, δ ppm): 13.0 (bs, 1H), 9.08 (s, 1H), 8.96 (s, 1H), 8.01-7.99 (m, 1H), 7.89-7.86 (m, 2H), 7.29 (d, 1H, J=3.36 Hz), 3.3-3.28 (m, 2H, obscured by water peak), 3.1 (t, 2H, J=7.84 Hz), 2.18 (m, 2H).

Example 97 (peak 2): White solid. Yield: 0.05 g
1H NMR (400 MHz, DMSO-d6, δ ppm): 13.0 (bs, 1H), 8.92 (s, 1H), 8.38-8.35 (m, 2H), 8.07 (d, 1H, J=8.12 Hz), 7.88 (d, 1H, J=3.84 Hz), 7.28 (d, 1H, J=3.8 Hz), 3.27-3.26 (m, 2H, obscured by water peak), 3.1 (t, 2H, J=7.24 Hz), 2.1 (m, 2H).

The following compounds were obtained applying analogues synthesis routes as described for synthesis example Nos. 21-23:

Compound No. 1-5

2-(1-(2-(3-Chloro-4-methoxyphenyl)-5,7-dihydrothieno[3,4-d]pyrimidin-4-yl)indolin-5-yl)acetic acid (Synthesis Example No. 98)

Yield: 0.09 g. Light yellow solid.
1H NMR (400 MHz, DMSO-d6, δ ppm): 12.32 (bs, 1H), 8.29 (d, 1H, J=1.28 Hz), 8.23 (d, 1H, J=8.68 Hz), 7.97 (d, 1H, J=8.24 Hz), 7.28 (d, 1H, J=8.72 Hz), 7.17 (s, 1H), 7.08 (d, 1H, J=8.16 Hz), 4.49 (s, 2H), 4.37 (t, 2H, J=8.24 Hz), 4.2 (s, 2H), 3.92 (s, 3H), 3.53 (s, 2H), 3.15 (2H, J=8.16 Hz).

Compound No. 1-8

2-(1-(2-(3-Chloro-4-methoxyphenyl)-6-oxido-5,7-dihydrothieno[3,4-d]pyrimidin-4-yl)indolin-5-yl)acetic acid (Synthesis Example No. 99)

Yellow solid. Yield: 60 mg (19% of theory)
1H NMR (400 MHz, DMSO-d6, δ ppm): 12.3 (bs, 1H), 8.34 (d, 1H, J=1.64 Hz), 8.28 (d, 1H, J=1.72 Hz), 7.98 (d, 1H, J=8.24 Hz), 7.32 (d, 1H, J=8.72 Hz), 7.2 (s, 1H), 7.12 (d, 1H, J=8.32 Hz), 4.74 (d, 1H, J=16.32 Hz), 4.52-4.43 (m, 2H), 4.38-4.27 (m, 2H), 4.02 (d, 1H, J=16.84 Hz), 3.94 (s, 3H), 3.55 (s, 2H), 3.24-3.11 (m, 2H).

Compound No. 1-23

2-(1-(2-(5-Fluorothiophen-2-yl)-5,7-dihydrothieno[3,4-d]pyrimidin-4-yl)indolin-5-yl)acetic acid (Synthesis Example No. 100)

Yellow solid. Yield: 1.7 g
1H NMR (400 MHz, DMSO-d6, δ ppm): 8.01 (d, 1H, J=8.32 Hz), 7.56 (t, 1H, J=3.52 Hz), 7.16-7.11 (m, 2H), 6.83 (d, 1H, J=3.08 Hz), 4.51 (s, 2H), 4.39 (t, 2H, J=8.16 Hz), 4.16 (s, 2H), 3.53 (s, 2H), 3.15 (t, 2H, J=7.88 Hz).

Compound No. 1-24

2-(1-(2-(5-Fluorothiophen-2-yl)-6-oxido-5,7-dihydrothieno[3,4-d]pyrimidin-4-yl)indolin-5-yl)acetic acid (Synthesis Example No. 101)

Yellow solid. Yield: 52 mg
1H NMR (400 MHz, DMSO-d6, δ ppm): 12.29 (s, 1H), 8.01 (d, 1H, J=8.24 Hz), 7.61 (t, 1H, J=3.8 Hz), 7.18-7.14 (m, 2H), 6.85 (d, 1H, J=2.84 Hz), 4.72 (d, 1H, J=16.28 Hz), 4.48-4.27 (m, 4H), 3.96 (d, 1H, J=16.88 Hz), 3.54 (s, 2H), 3.25-3.1 (m, 2H).

Compound No. 1-80

2-(1-(2-(Benzo[b]thiophen-2-yl)-6-oxido-5,7-dihydrothieno[3,4-d]pyrimidin-4-yl)indolin-5-yl)acetic acid (Synthesis Example No. 102)

Light yellow solid. Yield: 77 mg (15% of theory)
1H NMR (400 MHz, DMSO-d6, δ ppm): 8.26 (s, 1H), 8.2 (d, 1H, J=8.48 Hz), 8.0 (d, 1H, J=6.25 Hz), 8.05-7.98 (m, 2H), 7.44-7.42 (m, 2H), 7.22-7.2 (m, 2H), 4.76 (d, 1H, J=16.44 Hz), 4.54-4.44 (m, 3H), 4.34-4.3 (m, 1H), 4.02 (d, 1H, J=16.76 Hz), 3.56 (s, 2H), 3.15-3.16 (m, 2H).

Compound No. 1-81

2-(1-(2-(Benzofuran-5-yl)-6-oxido-5,7-dihydrothieno[3,4-d]pyrimidin-4-yl)indolin-5-yl)acetic acid (Synthesis Example No. 103)

White solid. Yield: 51 mg (19% of theory)
1H NMR (400 MHz, DMSO-d6, δ ppm): 12.26 (s, 1H), 8.68 (s, 1H), 8.36 (d, 1H, J=8.68 Hz), 8.07-8.05 (m, 2H), 7.73 (d, 1H, J=8.64 Hz), 7.2-7.16 (m, 2H), 7.11 (d, 1H, J=1.28 Hz), 4.75 (d, 1H, J=16.28 Hz), 4.54-4.46 (m, 2H), 4.39-4.29 (m, 2H), 4.03 (d, 1H, J=16.68 Hz), 3.56 (s, 2H), 3.26-3.13 (m, 2H).

Compound No. 1-18

2-(1-(2-(4-Chlorothiophen-2-yl)-6,7-dihydro-5H-cyclopenta[d]pyrimidin-4-yl)indolin-5-yl)acetic acid (Synthesis Example No. 104)

The synthesis route described for synthesis example No. 5 was applied in the preparation of the target compound. Yellow solid. Yield: 0.09 g
1H NMR (400 MHz, DMSO-d6, δ ppm): 12.23 (bs, 1H), 8.14 (d, 1H, J=8.24 Hz), 7.7-7.67 (m, 2H), 7.14-7.1 (m, 2H), 4.38 (t, 2H, J=8.36 Hz), 3.52 (s, 2H), 3.21 (t, 2H, J=7.12 Hz), 3.15 (t, 2H, J=8.24 Hz), 2.85 (t, 2H, J=7.64 Hz), 2.05-2.0 (m, 2H).

Compound No. 1-19

2-(1-(2-(5-Chlorothiophen-3-yl)-6,7-dihydro-5H-cyclopenta[d]pyrimidin-4-yl)indolin-5-yl)acetic acid (Synthesis Example No. 105)

Synthesized in analogy to synthesis example No. 5. White solid. Yield: 0.12 g
1H NMR (400 MHz, DMSO-d6, δ ppm): 12.24 (bs, 1H), 8.12-8.08 (m, 2H), 7.62 (s, 1H), 7.14-7.1 (m, 2H), 4.36 (t, 2H, J=7.52 Hz), 3.51 (s, 2H), 3.21-3.12 (m, 4H), 2.85 (t, 2H, J=7.6 Hz), 2.03-1.99 (m, 2H).

Compound No. 1-16

2-(1-(2-(5-Cyanothiophen-2-yl)-6,7-dihydro-5H-cyclopenta[d]pyrimidin-4-yl)indolin-5-yl)acetic acid (Synthesis Example No. 106)

Prepared in three steps from 2,4-dichloro-6,7-dihydro-5H-cyclopenta[d]pyrimidine and methyl 2-(indolin-5-yl)acetate in analogy to example No. 20. Yellow solid. Yield: 0.12 g 1H NMR (400 MHz, DMSO-d6, δ ppm): 12.26 (bs, 1H), 8.11 (d, 1H, J=8.64 Hz), 7.99 (d, 1H, J=3.76 Hz), 7.86 (d, 1H, J=3.8 Hz), 7.16-7.14 (m, 2H), 4.0 (t, 2H, J=8.4 Hz), 3.52 (s, 2H), 3.25 (t, 2H, J=7.36 Hz), 3.16 (t, 2H, J=8.28 Hz), 2.88 (t, 2H, J=7.56 Hz), 2.05-2.01 (m, 2H)

Compound No. 1-75

2-(1-(2-(5-Carbamoylthiophen-2-yl)-6,7-dihydro-5H-cyclopenta[d]pyrimidin-4-yl)indolin-5-yl)acetic acid (Synthesis Example No. 107)

Sodium hydroxide (0.086 g, 2.16 mmol) in water (5 mL) was added to a cooled solution of synthesis example No. 105 (0.18 g, 0.43 mmol) in THF (5 mL) and the mixture was stirred at room temperature for 4 h. The solvent was evaporated and the residue was diluted with water (15 mL) and washed with ethyl acetate (2×15 mL). The aqueous phase was then acidified with sodium hydrogen sulphate, and brine (30 mL) and THF (20 mL) were added. The organic layer was separated, dried over sodium sulfate and concentrated. The remnant was finally washed with methanol/dichloromethane=1:100 (3×20 mL). Yellow solid. Yield: 95 mg (52% of theory)

1H NMR (400 MHz, DMSO-d6, δ ppm): 12.28 (bs, 1H), 8.18 (d, 1H, J=8.12 Hz), 8.1 (bs, 1H), 7.8-7.74 (m, 2H), 7.5 (bs, 1H), 7.14-7.11 (m, 2H), 4.37 (t, 2H, J=8.32 Hz), 3.53 (s, 2H), 3.23-3.13 (m, 4H), 2.86 (t, 2H, J=7.76 Hz), 2.03-1.99 (m, 2H).

SYNTHESIS EXAMPLE NO. 108

2-(1-(2-(Thiazol-5-yl)-6,7-dihydro-5H-cyclopenta[d]pyrimidin-4-yl)indolin-5-yl)acetic acid (Compound No. 1-17)

108a) Methyl 2-(1-(2-(thiazol-5-yl)-6,7-dihydro-5H-cyclopenta[d]pyrimidin-4-yl)indolin-5-yl)acetate Bis(triphenylphosphine)palladium(II) dichloride (18.38 mg, 0.026 mmol) was added to a solution of methyl 2-(1-(2-chloro-6,7-dihydro-5H-cyclopenta[d]pyrimidin-4-yl)indolin-5-yl)acetate (0.18 g, 0.52 mmol) and 5-tributylstannanyl-thiazole (0.235 g, 0.629 mmol) in DMF (2 mL) and the resulting mixture was stirred at 120° C. for 16 h. The mixture was diluted with saturated potassium fluoride solution (10 mL), stirred for 10 min and then extracted with ethyl acetate (3×20 mL). The combined organic layers were dried over sodium sulfate and evaporated. The residue was purified by flash column chromatography [silica containing 10% potassium fluoride; ethyl acetate/hexane=3:10]. White solid. Yield: 0.08 g (39% of theory)

108b) 2-(1-(2-(Thiazol-5-yl)-6,7-dihydro-5H-cyclopenta[d]pyrimidin-4-yl)indolin-5-yl)acetic acid Ester hydrolysis of 107a) via stirring with sodium hydroxide in methanol at 75° C. Light yellow solid. Yield: 0.05 g 1H NMR (400 MHz, DMSO-d6, δ ppm): 12.24 (bs, 1H), 9.16 (s, 1H), 8.51 (s, 1H), 8.15 (d, 1H, J=8.24 Hz), 7.15-7.11 (m, 2H), 4.38 (t, 2H, J=8.36 Hz), 3.52 (s, 2H), 3.24 (t, 2H, J=7.2 Hz), 3.15 (t, 2H, J=8.4 Hz), 2.87 (t, 2H, J=7.88 Hz), 2.05-1.9 (m, 2H).

SYNTHESIS EXAMPLE NO. 109

2-((1-(2-(4-Cyano-3-fluorophenyl)-6-oxido-5,7-dihydrothieno[3,4-d]pyrimidin-4-yl)indolin-6-yl)oxy)-N,N-dimethylacetamide (Compound No. 2-77)

109a) Ethyl 2-((1-(2-chloro-5,7-dihydrothieno[3,4-d]pyrimidin-4-yl)indolin-6-yl)oxy)acetate Caesium carbonate (5.19 g, 15.95 mmol), BINAP (0.54 g, 0.87 mmol) and palladium(II) acetate (0.16 g, 0.72 mmol) were added under an argon atmosphere and at room temperature to a solution of 2,4-dichloro-5,7-dihydro-thieno[3,4-d]pyrimidine (3 g, 14.5 mmol) and ethyl 2-(indolin-6-yloxy)acetate (2.5 g, 11.6 mmol) in dry dioxane (80 mL). The reaction mixture was heated at 95° C. for 16 h, then cooled to ambient temperature and filtered. The filtrate was concentrated and the residue purified first by flash column chromatography [dichloromethane with 0-10% ethyl acetate] and finally by trituration in acetone/THF=1:2. White solid. Yield: 2.3 g (40% of theory)

109b) 2-((1-(2-Chloro-5,7-dihydrothieno[3,4-d]pyrimidin-4-yl)indolin-6-yl)oxy)acetic acid 1N sodium hydroxide solution (50.6 mL, 50.63 mmol) was added to the ethyl ester 109a) (6.6 g, 16.87 mmol) in 1,4-dioxane/ethanol (1:1; 120 mL) and the mixture was stirred at room temperature for 2 h. The solvents were distilled off and the remnant was diluted with water and acidified with saturated sodium hydrogen sulfate solution at 0° C. After stirring for 15 min, the precipitate was removed by filtration, repeatedly co-distilled with toluene and dried. Light yellow solid. Yield: 5.8 g (94% of theory)

109c) 2-((1-(2-Chloro-6-oxido-5,7-dihydrothieno[3,4-d]pyrimidin-4-yl)indolin-6-yl)oxy)acetic acid m-Chloroperoxybenzoic acid (77%, 2.94 g, 13.1 mmol) in THF (20 mL) was added at 0° C. to a solution of 109b) (5.6 g, 15.4 mmol) in dry THF (1000 mL). The reaction mixture was stirred at room temperature for 3 h, then poured onto brine and stirred for further 15 min. The organic layer was separated, dried over sodium sulfate and concentrated. The residue was triturated with acetone/hexane and finally co-distilled with toluene. White solid. Yield: 4.5 g (77% of theory)

109d) 2-((1-(2-Chloro-6-oxido-5,7-dihydrothieno[3,4-d]pyrimidin-4-yl)indolin-6-yl)oxy)-N,N-dimethylacetamide HATU (6.0 g, 15.82 mmol), diisopropylethylamine (9.4 mL, 52.76 mmol) and dimethylamine (2M in THF, 13.2 mL, 26.38 mmol) were added to a solution of acetic acid 109c) (5.0 g, 13.2 mmol) in THF/DMF=100:1 (252.5 mL). The resulting mixture was stirred at room temperature for 2 h, then diluted with dichloromethane (100 mL) and washed with saturated ammonium chloride solution, saturated sodium hydrogen carbonate solution, and brine. The organic layer was dried over sodium sulfate, the solvent was removed under vacuum and the residue was purified by flash column chromatography [methanol/dichloromethane=1:30]. White solid. Yield: 3.2 g (60% of theory)

109e) 2-((1-(2-(4-Cyano-3-fluorophenyl)-6-oxido-5,7-dihydrothieno[3,4-d]pyrimidin-4-yl)indolin-6-yl)oxy)-N,N-dimethylacetamide The pyrimidine chloride 109d) (100 mg, 0.25 mmol) and 4-cyano-3-fluoro phenyl boronic acid (50 mg, 0.32 mmol) were submitted to a Suzuki reaction in analogy to the procedure for synthesis example No. 70. Light brown solid. Yield: 81 mg (65% of theory)

1H NMR (400 MHz, DMSO-d6, δ ppm): 8.35 (d, 1H, J=8.2 Hz), 8.27 (d, 1H, J=10.6 Hz), 8.1 (t, 1H, J=7.4 Hz), 7.59 (s, 1H), 7.18 (d, 1H, J=8.1 Hz), 6.6 (dd, 1H, J=1.8 and 7.84 Hz), 4.77-4.73 (m, 3H), 4.58-4.49 (m, 2H), 4.4-4.31 (m, 2H), 4.06 (d, 1H, J=16.92 Hz), 3.16-3.07 (m, 2H), 2.94 (s, 3H), 2.79 (s, 3H).

The following compounds were obtained in an analogous manner

Compound No. 1-38

2-((1-(2-(2-Fluoropyridin-4-yl)-6-oxido-5,7-dihydrothieno[3,4-d]pyrimidin-4-yl)indolin-6-yl)oxy)-N,N-dimethylacetamide (Synthesis Example No. 110)

Yellow solid. Yield: 40 mg

1H NMR (400 MHz, DMSO-d6, δ ppm): 8.43 (d, 1H, J=5.1 Hz), 8.18 (d, 1H, J=4.9 Hz), 7.87 (s, 1H), 7.63 (d, 1H, J=2.1 Hz), 7.19 (d, 1H, J=8.3 Hz), 6.6 (dd, 1H, J=2.2 and 8.1 Hz), 4.78-4.74 (m, 3H), 4.59-4.48 (m, 2H), 4.42-4.3 (m, 2H), 4.06 (d, 1H, J=17 Hz), 3.2-3.08 (m, 2H), 2.94 (s, 3H), 2.79 (s, 3H).

Compound No. 2-139

2-((1-(2-(6-Methoxypyridin-3-yl)-6-oxido-5,7-dihydrothieno[3,4-d]pyrimidin-4-yl)indolin-6-yl)oxy)-N,N-dimethylacetamide (Synthesis Example No. 111)

Yellowish solid. Yield: 45 mg

1H NMR (400 MHz, DMSO-d6, δ ppm): 9.11 (d, 1H, J=2 Hz), 8.56 (dd, 1H, J=2.3 and 8.7 Hz), 7.63 (d, 1H, J=2 Hz), 7.17 (d, 1H, J=8.1 Hz), 6.96 (d, 1H, J=8.7 Hz), 6.57 (dd, 1H, J=2.2 and 8.1 Hz), 4.78 (s, 2H), 4.72 (d, 1H, J=16.3 Hz), 4.53-4.43 (m, 2H), 4.37-4.26 (m, 2H), 4.02 (d, 1H, J=16 Hz), 3.94 (s, 3H), 3.18-3.07 (m, 2H), 2.96 (s, 3H), 2.81 (s, 3H).

Compound No. 2-78

2-((1-(2-(4-Chloro-3-fluorophenyl)-6-oxido-5,7-dihydrothieno[3,4-d]pyrimidin-4-yl)indolin-6-yl)oxy)-N,N-dimethylacetamide (Synthesis Example No. 112)

Light orange solid. Yield: 58 mg

1H NMR (400 MHz, DMSO-d6, δ ppm): 8.23-8.2 (m, 2H), 7.76 (t, 1H, J=8.2 Hz), 7.6 (s, 1H), 7.18 (d, 1H, J=8.2 Hz), 6.6-6.58 (m, 1H), 4.77-4.71 (m, 3H), 4.56-4.44 (m, 2H), 4.38-4.18 (m, 2H), 4.04 (d, 1H, J=16.8 Hz), 3.18-3.05 (m, 2H), 2.93 (s, 3H), 2.79 (s, 3H).

Compound No. 2-140

N,N-Dimethyl-2-((1-(2-(2-methylthiazol-5-yl)-6-oxido-5,7-dihydrothieno[3,4-d]pyrimidin-4-yl)indolin-6-yl)oxy)acetamide (Synthesis Example No. 113)

Light yellow solid. Yield: 66 mg

1H NMR (400 MHz, DMSO-d6, δ ppm): 8.31 (s, 1H), 7.68 (s, 1H), 7.16 (d, 1H, J=8.1 Hz), 6.59-6.57 (m, 1H), 4.82 (s, 2H), 4.71 (d, 1H, J=16.3 Hz), 4.52-4.46 (m, 2H), 4.37 (d, 1H, J=16.4 Hz), 4.32-4.26 (m, 1H), 3.99 (d, 1H, J=16.8 Hz), 3.15-3.11 (m, 2H), 2.98 (s, 3H), 2.82 (s, 3H), 2.71 (s, 3H).

Compound No. 2-79

2-((1-(2-(3-Fluoro-4-hydroxyphenyl)-6-oxido-5,7-dihydrothieno[3,4-d]pyrimidin-4-yl)indolin-6-yl)oxy)-N,N-dimethylacetamide (Synthesis Example No. 114)

Yellow solid. Yield: 70 mg

1H NMR (400 MHz, DMSO-d6, δ ppm): 10.44 (s, 1H), 8.05-8.02 (m, 2H), 7.62 (d, 1H, J=2.1 Hz), 7.16 (d, 1H, J=8.2 Hz), 7.07 (t, 1H, J=9.1 Hz), 6.57 (dd, 1H, J=2.2 and 8.2 Hz), 4.71-4.67 (m, 3H), 4.51-4.45 (m, 2H), 4.35-4.28 (m, 2H), 3.99 (d, 1H, J=16.9 Hz), 3.12-3.06 (m, 2H), 2.94 (s, 3H), 2.8 (s, 3H).

Compound No. 2-80

5-(4-(6-(2-(Dimethylamino)-2-oxoethoxy)indolin-1-yl)-6-oxido-5,7-dihydrothieno[3,4-d]pyrimidin-2-yl)thiophene-2-carboxamide (Synthesis Example No. 115)

Light yellow solid. Yield: 45 mg

1H NMR (400 MHz, DMSO-d6, δ ppm): 8.09 (bs, 1H), 7.86 (d, 1H, J=3.28 Hz), 7.77 (d, 1H, J=3.44 Hz), 7.70 (s, 1H), 7.54 (bs, 1H), 7.16 (d, 1H, J=7.92 Hz), 6.59 (d, 1H, J=7.84 Hz), 4.81 (s, 2H), 4.74-4.7 (m, 1H), 4.52-4.47 (m, 2H), 4.4-4.29 (m, 2H), 3.99 (d, 1H, 16 Hz), 3.15-3.07 (m, 2H), 2.96 (s, 3H), 2.81 (s, 3H).

Compound No. 2-81

5-(4-(6-(2-(Dimethylamino)-2-oxoethoxy)indolin-1-yl)-6,6-dioxido-5,7-dihydrothieno[3,4-d]pyrimidin-2-yl)thiophene-2-carboxamide (Synthesis Example No. 116)

White solid. Yield: 0.04 g

1H NMR (400 MHz, DMSO-d6, δ ppm): 8.1 (bs, 1H), 7.84 (d, 1H, J=3.8 Hz), 7.77 (d, 1H, J=3.8 Hz), 7.69 (d, 1H, J=1.68 Hz), 7.55 (bs, 1H), 7.17 (d, 1H, J=8.08 Hz), 6.62 (dd, 1H, J=8.24 and 1.88 Hz), 4.87 (s, 2H), 4.81 (s, 2H), 4.6 (s, 2H), 4.34 (t, 2H, J=8.12 Hz), 3.08 (t, 2H, J=8.04 Hz), 2.98 (s, 3H), 2.81 (s, 3H).

Compound No. 2-82

2-((1-(2-(5-Cyanothiophen-2-yl)-6-oxido-5,7-dihydrothieno[3,4-d]pyrimidin-4-yl)indolin-6-yl)oxy)-N,N-dimethylacetamide (Synthesis Example No. 117)

Yellow solid. Yield: 95 mg
1H NMR (400 MHz, DMSO-d6, δ ppm): 8.04 (d, 1H, J=3.92 Hz), 7.94 (d, 1H, J=3.92 Hz), 7.66 (d, 1H, J=1.92 Hz), 7.16 (d, 1H, J=8.44 Hz), 6.6 (dd, 1H, J=8.12 and 2.12 Hz), 4.81 (s, 2H, 4.74 (d, 1H, J=16.48 Hz), 4.54-4.5 (m, 2H), 4.48-4.28 (m, 2H), 4.02 (d, 1H, J=16 Hz), 3.16-3.04 (2H, m), 2.98 (s, 3H), 2.82 (s, 3H).

Compound No. 2-83

2-((1-(2-(5-Cyanothiophen-2-yl)-6,6-dioxido-5,7-dihydrothieno[3,4-d]pyrimidin-4-yl)indolin-6-yl)oxy)-N,N-dimethylacetamide (Synthesis Example No. 118)

Yellow solid. Yield: 0.17 g
1H NMR (400 MHz, DMSO-d6, δ ppm): 8.03 (d, 1H, J=3.88 Hz), 7.91 (d, 1H, J=3.88 Hz), 7.65 (s, 1H), 7.17 (d, 1H, J=8.16 Hz), 6.64-6.62 (m, 1H), 4.9 (s, 2H), 4.81 (s, 2H), 4.63 (s, 2H), 4.36 (t, 2H, J=8 Hz), 3.08 (t, 2H, J=8 Hz), 2.97 (s, 3H), 2.82 (s, 3H).

Compound No. 2-84

2-((1-(2-(5-Cyanothiophen-2-yl)-6,7-dihydro-5H-cyclopenta[d]pyrimidin-4-yl)indolin-6-yl)oxy)-N,N-dimethylacetamide (Synthesis Example No. 119)

Light yellow solid. Yield: 43 mg
1H NMR (400 MHz, DMSO-d6, δ ppm): 8.0 (d, 1H, J=3.88 Hz), 7.87 (d, 1H, J=3.92 Hz), 7.76 (d, 1H, J=2.04 Hz), 7.13 (d, 1H, J=8.1 Hz), 6.55 (dd, 1H, J=8.12 and 2.16 Hz), 4.8 (s, 2H), 4.39 (t, 2H, J=8.2 Hz), 3.24 (t, 2H, J=7.24 Hz), 3.08 (t, 2H, J=8.2 Hz), 2.99 (s, 3H), 2.89 (t, 2H, J=7.8 Hz), 2.82 (s, 3H), 2.03 (m, 2H).

Compound No. 2-55

5-(4-(6-(2-(Dimethylamino)-2-oxoethoxy)indolin-1-yl)-6,7-dihydro-5H-cyclopenta[d]pyrimidin-2-yl)thiophene-2-carboxamide (Synthesis Example No. 120)

Light yellow solid. Yield: 45 mg
1H NMR (400 MHz, DMSO-d6, δ ppm): 8.05 (bs, 1H), 7.83-7.74 (m, 3H), 7.49 (bs, 1H), 7.12 (d, 1H, J=8.12 Hz), 6.53 (d, 1H, J=8.04 Hz), 4.8 (s, 2H), 4.38 (t, 2H, J=8.4 Hz), 3.2 (t, 2H, J=7.28 Hz), 3.08 (t, 2H, J=8.16 Hz), 2.97 (s, 3H), 2.87 (t, 2H, J=7.68 Hz), 2.81 (s, 3H), 2.02 (m, 2H).

Compound No. 2-46

2-((1-(2-(5-Fluorothiophen-2-yl)-6,7-dihydro-5H-cyclopenta[d]pyrimidin-4-yl)indolin-6-yl)oxy)-N,N-dimethylacetamide (Synthesis Example No. 121)

White solid. Yield: 0.08 g
1H NMR (400 MHz, DMSO-d6, δ ppm): 7.76 (d, 1H, J=2.0 Hz), 7.54 (t, 1H, J=4.08 Hz), 7.11 (d, 1H, J=8.16 Hz), 6.82 (d, 1H, J=2.84 Hz), 6.51 (dd, 1H, J=8.08 Hz and 2.0 Hz), 4.79 (s, 2H), 4.36 (t, 2H, J=8.28 Hz), 3.18 (t, 2H, J=7.16 Hz), 3.07 (t, 2H, J=8.51 Hz), 2.97 (s, 3H), 2.85-2.81 (m, 5H), 2.0 (m, 2H).

Compound No.-34

2-((1-(2-(3-Fluoro-4-methoxyphenyl)-6,7-dihydro-5H-cyclopenta[d]pyrimidin-4-yl)indolin-6-yl)oxy)-N,N-dimethylacetamide (Synthesis Example No. 122)

White solid. Yield: 0.12 g
1H NMR (400 MHz, DMSO-d6, δ ppm): 8.15 (d, 1H, J=8.12 Hz), 8.05 (d, 1H, J=12.88 Hz), 7.75 (s, 1H), 7.28 (t, 1H, J=8.72 Hz), 7.12 (d, 1H, J=8.08 Hz), 6.53-6.50 (m, 1H), 4.75 (s, 2H), 4.37 (t, 2H, J=8.36 Hz), 3.91 (s, 3H), 3.18 (t, 2H, J=7.12 Hz), 3.08 (t, 2H, J=7.96 Hz), 2.94 (s, 3H), 2.89 (t, 2H, J=7.92 Hz), 2.66 (s, 3H), 2.03 (m, 2H).

Compound No. 2-86

2-((1-(2-(4-Bromo-3-fluorophenyl)-6-oxido-5,7-dihydrothieno[3,4-d]pyrimidin-4-yl)indolin-6-yl)oxy)-N,N-dimethylacetamide (Synthesis Example No. 123)

The target compound was obtained applying the same synthesis strategy as for the preparation of examples 21/22.
Yellow solid. Yield: 93 mg
1H NMR (400 MHz, DMSO-d6, δ ppm): 8.18-8.14 (m, 2H), 7.9-7.87 (m, 1H), 7.6 (s, 1H), 7.18 (d, 1H, J=7.64 Hz), 6.6-6.58 (m, 1H), 4.77-4.7 (m, 3H), 4.56-4.48 (m, 2H), 4.38-4.34 (m, 2H), 4.04 (d, 1H, J=17.2 Hz), 3.15-3.1 (m, 2H), 2.93 (s, 3H), 2.66 (s, 3H).

Compound No. 2-34

2-((1-(2-(5-Fluorothiophen-2-yl)-6-oxido-5,7-dihydrothieno[3,4-d]pyrimidin-4-yl)indolin-6-yl)oxy)-N,N-dimethylacetamide (Synthesis Example No. 124)

Prepared according to the synthesis strategy applied for the examples 21/22. Light yellow solid. Yield: 0.08 g
1H NMR (400 MHz, DMSO-d6, δ ppm): 7.65-7.62 (m, 2H), 7.14 (d, 1H, J=8.16 Hz), 6.87 (t, 1H, J=1.52 Hz), 6.56 (dd, 1H, J=8.2 and 2.1 Hz), 4.81 (s, 2H), 4.68-4.37 (m, 5H), 3.99 (d, 1H, J=16.56 Hz), 3.31-3.05 (m, 2H), 2.97 (s, 3H), 2.81 (s, 3H).

Compound No. 2-36

2-((1-(2-(3-Fluoro-4-methoxyphenyl)-6-oxido-5,7-dihydrothieno[3,4-d]pyrimidin-4-yl)indolin-6-yl)oxy)-N,N-dimethylacetamide (Synthesis Example No. 125)

The same synthesis strategy as for the preparation of compounds according to synthesis examples Nos. 21/22 was used. White solid. Yield: 75 mg
1H NMR (400 MHz, DMSO-d6, δ ppm): 8.19 (d, 1H, J=8.88 Hz), 8.07 (dd, 1H, J=12.8 and 1.8 Hz), 7.61 (d, 1H, J=2.12 Hz), 7.32 (t, 1H, J=8.72 Hz), 7.17 (d, 1H, J=8.24 Hz), 6.57 (dd, 1H, J=8.2 and 2.25 Hz), 4.77 (s, 2H), 4.7 (d, 1H, J=16.36 Hz), 4.53-4.44 (m, 2H), 4.35-4.26 (m, 2H), 4.01 (d, 1H, J=16.92 Hz), 3.93 (s, 3H), 3.17-3.07 (m, 2H), 2.94 (s, 3H), 2.8 (s, 3H).

The examples in table 4 were synthesized according to the following general procedure:

Tetrakis(triphenylphosphine)-palladium(0) (3 μmol, 0.03 eq) was added under an argon atmosphere to a mixture of 2-((1-(2-chloro-6-oxido-5,7-dihydrothieno[3,4-d]pyrimidin-4-yl)indolin-6-yl)oxy)-N,N-dimethylacetamide (100 μmol, 1.0 eq.), a boronic acid (150 μmol, 1.5 eq) and 2N sodium hydroxide solution (610 μmol, 6.1 eq) in DME (3.0 mL). The mixture was heated to 120° C. for 1 h in a sealed tube under microwave irradiation. The reaction mixture was then cooled to room temperature, diluted with water (2.5 mL) and extracted with dichloromethane (2 mL×3). The combined organic layers were concentrated under reduced pressure and finally purified by preparative HPLC.

TABLE 4

| Compound No. | Name | Mass peak [M + H]+ |
|---|---|---|
| 2-87 | N,N-Dimethyl-2-[[1-(6-oxo-2-p-tolyl-5,7-dihydro-thieno[3,4-d]pyrimidin-4-yl)-2,3-dihydro-1H-indol-6-yl]oxy]-acetamide | 463.2 |
| 2-88 | 2-[[1-[2-(2-Methoxyphenyl)-6-oxo-5,7-dihydro-thieno[3,4-d]pyrimidin-4-yl]-2,3-dihydro-1H-indol-6-yl]oxy]-N,N-dimethyl-acetamide | 479.2 |
| 2-89 | 2-[[1-[2-(3-Chlorophenyl)-6-oxo-5,7-dihydro-thieno[3,4-d]pyrimidin-4-yl]-2,3-dihydro-1H-indol-6-yl]oxy]-N,N-dimethyl-acetamide | 483.1 |
| 2-90 | 2-[[1-[2-(4-Chlorophenyl)-6-oxo-5,7-dihydro-thieno[3,4-d]pyrimidin-4-yl]-2,3-dihydro-1H-indol-6-yl]oxy]-N,N-dimethyl-acetamide | 483.1 |
| 2-91 | 2-[[1-[2-(3-Methoxyphenyl)-6-oxo-5,7-dihydro-thieno[3,4-d]pyrimidin-4-yl]-2,3-dihydro-1H-indol-6-yl]oxy]-N,N-dimethyl-acetamide | 479.2 |
| 2-92 | 2-[[1-[2-(4-Cyano-phenyl)-6-oxo-5,7-dihydro-thieno[3,4-d]pyrimidin-4-yl]-2,3-dihydro-1H-indol-6-yl]oxy]-N,N-dimethyl-acetamide | 474.2 |
| 2-93 | N,N-Dimethyl-2-[[1-(6-oxo-2-phenyl-5,7-dihydro-thieno[3,4-d]pyrimidin-4-yl)-2,3-dihydro-1H-indol-6-yl]oxy]-acetamide | 449.2 |
| 2-94 | N,N-Dimethyl-2-[[1-(2-o-tolyl-6-oxo-5,7-dihydro-thieno[3,4-d]pyrimidin-4-yl)-2,3-dihydro-1H-indol-6-yl]oxy]-acetamide | 463.2 |
| 2-95 | N,N-Dimethyl-2-[[1-(2-m-tolyl-6-oxo-5,7-dihydro-thieno[3,4-d]pyrimidin-4-yl)-2,3-dihydro-1H-indol-6-yl]oxy]-acetamide | 463.2 |
| 2-96 | 2-[[1-[2-(2-Chlorophenyl)-6-oxo-5,7-dihydro-thieno[3,4-d]pyrimidin-4-yl]-2,3-dihydro-1H-indol-6-yl]oxy]-N,N-dimethyl-acetamide | 483.1 |
| 2-97 | N,N-Dimethyl-2-[[1-[6-oxo-2-[2-(trifluoromethyl)-phenyl]-5,7-dihydro-thieno[3,4-d]pyrimidin-4-yl]-2,3-dihydro-1H-indol-6-yl]oxy]-acetamide | 517.1 |
| 2-98 | 2-[[1-[2-(3-Cyano-phenyl)-6-oxo-5,7-dihydro-thieno[3,4-d]pyrimidin-4-yl]-2,3-dihydro-1H-indol-6-yl]oxy]-N,N-dimethyl-acetamide | 474.2 |
| 2-99 | 2-[[1-[2-(4-Fluorophenyl)-6-oxo-5,7-dihydro-thieno[3,4-d]pyrimidin-4-yl]-2,3-dihydro-1H-indol-6-yl]oxy]-N,N-dimethyl-acetamide | 467.2 |
| 2-100 | 2-[[1-[2-(2-Fluorophenyl)-6-oxo-5,7-dihydro-thieno[3,4-d]pyrimidin-4-yl]-2,3-dihydro-1H-indol-6-yl]oxy]-N,N-dimethyl-acetamide | 467.2 |
| 2-24 | 2-[[1-[2-(3-Fluorophenyl)-6-oxo-5,7-dihydro-thieno[3,4-d]pyrimidin-4-yl]-2,3-dihydro-1H-indol-6-yl]oxy]-N,N-dimethyl-acetamide | 467.2 |
| 2-20 | 2-[[1-[2-(4-Methoxyphenyl)-6-oxo-5,7-dihydro-thieno[3,4-d]pyrimidin-4-yl]-2,3-dihydro-1H-indol-6-yl]oxy]-N,N-dimethyl-acetamide | 479.2 |
| 2-101 | N,N-Dimethyl-2-[[1-[6-oxo-2-[3-(trifluoromethyl)phenyl]-5,7-dihydro-thieno[3,4-d]pyrimidin-4-yl]-2,3-dihydro-1H-indol-6-yl]oxy]-acetamide | 517.1 |
| 2-102 | 2-[[1-[2-(Furan-3-yl)-6-oxo-5,7-dihydro-thieno[3,4-d]pyrimidin-4-yl]-2,3-dihydro-1H-indol-6-yl]oxy]-N,N-dimethyl-acetamide | 439.1 |
| 2-145 | 2-[[1-[2-(1,3-Benzodioxol-5-yl)-6-oxo-5,7-dihydro-thieno[3,4-d]pyrimidin-4-yl]-2,3-dihydro-1H-indol-6-yl]oxy]-N,N-dimethyl-acetamide | 493.2 |
| 2-146 | N,N-Dimethyl-2-[[1-(6-oxo-2-quinolin-3-yl-5,7-dihydro-thieno[3,4-d]pyrimidin-4-yl)-2,3-dihydro-1H-indol-6-yl]oxy]-acetamide | 500.2 |
| 2-144 | N,N-Dimethyl-2-[[1-(6-oxo-2-pyrimidin-5-yl-5,7-dihydro-thieno[3,4-d]pyrimidin-4-yl)-2,3-dihydro-1H-indol-6-yl]oxy]-acetamide | 451.2 |
| 2-103 | 2-[[1-[2-(2-Cyano-phenyl)-6-oxo-5,7-dihydro-thieno[3,4-d]pyrimidin-4-yl]-2,3-dihydro-1H-indol-6-yl]oxy]-N,N-dimethyl-acetamide | 474.2 |
| 2-104 | 2-[[1-[2-[2-(Methanesulfonamido)-phenyl]-6-oxo-5,7-dihydro-thieno[3,4-d]pyrimidin-4-yl]-2,3-dihydro-1H-indol-6-yl]oxy]-N,N-dimethyl-acetamide | 542.2 |
| 2-105 | 2-[[1-[2-(2-Methoxy-pyridin-3-yl)-6-oxo-5,7-dihydro-thieno[3,4-d]pyrimidin-4-yl]-2,3-dihydro-1H-indol-6-yl]oxy]-N,N-dimethyl-acetamide | 480.2 |
| 2-106 | N,N-Dimethyl-2-[[1-[2-(4-methylsulfonyl-phenyl)-6-oxo-5,7-dihydro-thieno[3,4-d]pyrimidin-4-yl]-2,3-dihydro-1H-indol-6-yl]oxy]-acetamide | 527.1 |
| 2-107 | N,N-Dimethyl-2-[[1-[2-(3-methylsulfonyl-phenyl)-6-oxo-5,7-dihydro-thieno[3,4-d]pyrimidin-4-yl]-2,3-dihydro-1H-indol-6-yl]oxy]-acetamide | 527.1 |
| 2-147 | 2-[[1-[2-(1H-Indol-6-yl)-6-oxo-5,7-dihydro-thieno[3,4-d]pyrimidin-4-yl]-2,3-dihydro-1H-indol-6-yl]oxy]-N,N-dimethyl-acetamide | 488.2 |
| 2-148 | 2-[[1-(2-Isoquinolin-6-yl-6-oxo-5,7-dihydro-thieno[3,4-d]pyrimidin-4-yl)-2,-dihydro-1H-indol-6-yl]oxy]-N,N-dimethyl-acetamide | 500.2 |

TABLE 4-continued

| Compound No. | Name | Mass peak [M + H]+ |
|---|---|---|
| 2-149 | N,N-Dimethyl-2-[[1-(6-oxo-2-quinolin-7-yl-5,7-dihydro-thieno[3,4-d]pyrimidin-4-yl)-2,3-dihydro-1H-indol-6-yl]oxy]-acetamide | 500.2 |
| 1-150 | 2-[[1-(2-Isoquinolin-7-yl-6-oxo-5,7-dihydro-thieno[3,4-d]pyrimidin-4-yl)-2,3-dihydro-1H-indol-6-yl]oxy]-N,N-dimethyl-acetamide | 500.2 |
| 2-108 | 3-[4-[6-[(Dimethyl-carbamoyl)-methoxy]-2,3-dihydro-1H-indol-1-yl]-6-oxo-5,7-dihydro-thieno[3,4-d]pyrimidin-2-yl]-benzamide | 492.2 |
| 2-109 | 2-[[1-[2-(4-Acetylamino-phenyl)-6-oxo-5,7-dihydro-thieno[3,4-d]pyrimidin-4-yl]-2,3-dihydro-1H-indol-6-yl]oxy]-N,N-dimethyl-acetamide | 506.2 |
| 2-151 | 2-[[1-[2-(1H-Indol-4-yl)-6-oxo-5,7-dihydro-thieno[3,4-d]pyrimidin-4-yl]-2,3-dihydro-1H-indol-6-yl]oxy]-N,N-dimethyl-acetamide | 488.2 |
| 2-152 | 2-[[1-[2-(1H-Indol-5-yl)-6-oxo-5,7-dihydro-thieno[3,4-d]pyrimidin-4-yl]-2,3-dihydro-1H-indol-6-yl]oxy]-N,N-dimethyl-acetamide | 488.2 |
| 2-110 | 2-[[1-[2-(4-Ethoxyphenyl)-6-oxo-5,7-dihydro-thieno[3,4-d]pyrimidin-4-yl]-2,3-dihydro-1H-indol-6-yl]oxy]-N,N-dimethyl-acetamide | 493.2 |
| 2-111 | 2-[[1-[2-(4-Chloro-3-methoxy-phenyl)-6-oxo-5,7-dihydro-thieno[3,4-d]pyrimidin-4-yl]-2,3-dihydro-1H-indol-6-yl]oxy]-N,N-dimethyl-acetamide | 513.1 |
| 2-153 | 2-[[1-[2-(2,3-Dihydro-benzofuran-5-yl)-6-oxo-5,7-dihydro-thieno[3,4-d]pyrimidin-4-yl]-2,3-dihydro-1H-indol-6-yl]oxy]-N,N-dimethyl-acetamide | 491.2 |
| 2-154 | 2-[[1-[2-(Benzofuran-5-yl)-6-oxo-5,7-dihydro-thieno[3,4-d]pyrimidin-4-yl]-2,3-dihydro-1H-indol-6-yl]oxy]-N,N-dimethyl-acetamide | 489.2 |
| 2-155 | 2-[[1-[2-(Benzo[b]thiophen-5-yl)-6-oxo-5,7-dihydro-thieno[3,4-d]pyrimidin-4-yl]-2,3-dihydro-1H-indol-6-yl]oxy]-N,N-dimethyl-acetamide | 505.1 |
| 2-112 | 2-[[1-[2-(4-Fluoro-2-methoxy-phenyl)-6-oxo-5,7-dihydro-thieno[3,4-d]pyrimidin-4-yl]-2,3-dihydro-1H-indol-6-yl]oxy]-N,N-dimethyl-acetamide | 497.2 |
| 2-113 | 2-[[1-[2-(2,5-Difluoro-phenyl)-6-oxo-5,7-dihydro-thieno[3,4-d]pyrimidin-4-yl]-2,3-dihydro-1H-indol-6-yl]oxy]-N,N-dimethyl-acetamide | 485.1 |

SYNTHESIS EXAMPLE 167

2-((1-(2-(5-Chlorothiophen-2-yl)-6,7-dihydro-5H-cyclopenta[d]-pyrimidin-4-yl)indolin-6-yl)oxy)-N-cyclopropylacetamide (Compound No. 2-114)

Cyclopropanamine (0.14 mL, 2.04 mmol) was added to a stirred solution of methyl 2-((1-(2-(5-chlorothiophen-2-yl)-6,7-dihydro-5H-cyclopenta[d]pyrimidin-4-yl)indolin-6-yl)oxy)acetate (300 mg, 0.68 mmol) in DMF/methanol (1:1; 10 mL) and the mixture was stirred at room temperature for 16 h. A precipitating solid was filtered off, washed with ethyl acetate, and dried under vacuum. White solid. Yield: 200 mg (45% of theory). Melting range: 190-194° C.

LC-MS (method 3): $R_t$=7.94 min, m/z: [M+H]$^+$=466.8

Compound No. 2-142

2-((1-(2-(5-Chlorothiophen-2-yl)-6,7-dihydro-5H-cyclopenta[d]pyrimidin-4-yl)indolin-6-yl)oxy)-1-(pyrrolidin-1-yl)ethanone (Synthesis Example No. 168)

Compound No. 2-142 was prepared analogously to synthesis example No. 167. White solid. Yield: 70 mg. Melting range: 209-212° C.

LC-MS (method 3): $R_t$=8.47 min, m/z: [M+H]$^+$=481.2

SYNTHESIS EXAMPLE NO. 169

2-((1-(2-(5-Chlorothiophen-2-yl)-6,7-dihydro-5H-cyclopenta[d]-pyrimidin-4-yl)indolin-6-yl)oxy)-N,N-dimethylethanamine (Compound No. 3-7)

169a) 1-(2-(5-Chlorothiophen-2-yl)-6,7-dihydro-5H-cyclopenta[d]pyrimidin-4-yl)indolin-6-ol A solution of 4-chloro-2-(5-chlorothiophen-2-yl)-6,7-dihydro-5H-cyclopenta[d]pyrimidine (10 g, 37.03 mmol, 1 eq), indolin-6-ol (5 g, 37.03 mmol, 1 eq) and sulfuric acid (6 mL, 111.0 mmol, 3 eq) in n-butanol (100 mL) was stirred at 120° C. for 5 h. The solvent was evaporated under vacuum, ethyl acetate (50 mL) was added, and the precipitate was filtered off. Yield: 10 g (75% of theory)

Mass spectroscopy: m/z: [M+H]$^+$=470.5

169b) 2-((1-(2-(5-Chlorothiophen-2-yl)-6,7-dihydro-5H-cyclopenta[d]pyrimidin-4-yl)indolin-6-yl)oxy)-N,N-dimethylethanamine A mixture containing the alcohol 169a) (300 mg, 0.81 mmol, 1 eq), cesium carbonate (789 mg, 2.43 mmol, 3.0 eq) and 2-chloro-N,N-dimethylethanamine hydrochloride (291 mg, 2.0 mmol, 2.5 eq) in DMF (10 mL) was stirred at 120° C. for 3 h. The reaction mixture was diluted with water and the precipitating solid was filtered off, washed with water (2×10 mL), dried and finally purified by preparative TLC [methanol dichloromethane=1:20]. White solid. Yield: 100 mg (28% of theory) Melting range: 155-158° C.

LC-MS (method 3): $R_t$=10.11 min, m/z: [M+H]$^+$=441.1

SYNTHESIS EXAMPLE NO. 170

2-((1-(2-(3-Fluoro-4-methoxyphenyl)-6-imino-6-oxido-5,7-dihydrothieno[3,4-d]pyrimidin-4-yl)indolin-6-yl)oxy)-N,N-dimethylacetamide (Compound No. 2-115)

170a) 2,2,2-Trifluoro-N-(2-(3-fluoro-4-methoxyphenyl)-4-hydroxy-6-oxido-5,7-dihydrothieno[3,4-d]pyrimidin-6-ylidene)acetamide Iodobenzene diacetate (1.09 g, 3.40 mmol) was added to a stirred suspension of 2-(3-fluoro-4-methoxyphenyl)-4-hydroxy-5,7-dihydrothieno[3,4-d]pyrimidine 6-oxide (500 mg, 1.70 mmol), 2,2,2-trifluoroacetamide (423 mg, 3.74 mmol), rhodium(II) acetate dimer (75.0 mg, 0.17 mmol) and magnesium oxide (309 mg, 7.48 mmol) in dry 1,4-dioxane (7 mL) at 40° C. The reaction mixture was stirred at 40° C. for 30 minutes and then cooled to room temperature. Silica (70-200 μm, ~1 g) was added and the solvent was carefully removed under reduced pressure. The absorbed material was loaded on a silica flash column and purified [heptane with 0%-100% ethyl acetate] Pale blue solid. Yield: 457 mg (66% of theory)

Mass spectroscopy: m/z: [M+H]$^+$=406

170b) 2-(3-Fluoro-4-methoxyphenyl)-6-oxido-6-((2,2,2-trifluoroacetyl)imino)-5,7-dihydrothieno[3,4-d]pyrimidin-4-yl trifluoromethanesulfonate A solution of triflic anhydride (0.17 mL, 1.00 mmol) in dichloromethane (0.5 mL) was added dropwise to a cooled (0° C.) solution of 170a) (325 mg, 0.80 mmol) and triethylamine (0.17 mL, 1.20 mmol) in dichloromethane (2.5 mL). The reaction mixture was stirred at room temperature for 1 h and then directly chromatographed on a silica flash column [heptane with 25%-100% ethyl acetate]. Pale solid. Yield: 252 mg (58% of theory)

Mass spectroscopy: m/z: [M+H]$^+$=538

170c) N-(4-(6-(2-(Dimethylamino)-2-oxoethoxy)indolin-1-yl)-2-(3-fluoro-4-methoxyphenyl)-6-oxido-5,7-dihydrothieno[3,4-d]pyrimidin-6-ylidene)-2,2,2-trifluoroacetamide A solution of 170b) (250 mg, 0.47 mmol) and 2-(indolin-6-yloxy)-N,N-dimethylacetamide (204 mg, purity=76%, 0.71 mmol) in dry acetonitril (10 mL) was stirred at room temperature for 18 h. Silica (1 g) was added and the solvent was carefully removed under reduced pressure. The absorbed material was loaded on a silica flash column and purified [heptane with 0%-100% ethyl acetate]. Pale solid. Yield 159 mg (56% of theory)

Mass spectroscopy: m/z: [M+H]$^+$=608

170d) 2-((1-(2-(3-Fluoro-4-methoxyphenyl)-6-imino-6-oxido-5,7-dihydrothieno[3,4-d]pyrimidin-4-yl)indolin-6-yl)oxy)-N,N-dimethylacetamide Potassium carbonate (70.5 mg, 0.51 mmol) was added to a stirred suspension of 170c) (155 mg, 0.26 mmol) in a blend of acetonitril (2.5 mL) and methanol (2.5 mL) at room temperature. The mixture was stirred for 1 h and then slowly poured into water (20 mL). After 5 minutes stirring, the solid was filtered off, washed with water (1 mL) and dried in a vacuum-oven at 40° C. Pale solid. Yield 107 mg (82% of theory)

Mass spectroscopy: m/z: [M+H]$^+$=512

1H NMR (400 MHz, DMSO-d6, δ ppm): 8.15 (d, J=8.6 Hz, 1H), 8.04 (dd, J=12.8, 1.7 Hz, 1H), 7.58 (d, J=2.0 Hz, 1H), 7.32 (t, J=8.7 Hz, 1H), 7.17 (d, J=8.2 Hz, 1H), 6.59 (dd, J=8.2, 2.2 Hz, 1H), 4.78 (s, 2H), 4.69 (q, J=15.2 Hz, 2H), 4.54-4.46 (m, 2H), 4.39 (d, J=15.9 Hz, 1H), 4.33 (t, J=8.3 Hz, 2H), 3.92 (s, 3H), 3.08 (t, J=8.1 Hz, 2H), 2.94 (s, 3H), 2.80 (s, 3H).

SYNTHESIS EXAMPLE NO. 171

2-((1-(2-(3,4-Difluorophenyl)-6-oxido-5,7-dihydrothieno[3,4-d]pyrimidin-4-yl)indolin-6-yl)oxy)-N,N-dimethylacetamide (Compound No. 2-40)

171a) 2-((1-(2-(3,4-Difluorophenyl)-5,7-dihydrothieno[3,4-d]pyrimidin-4-yl)indolin-6-yl)oxy)-N,N-dimethylacetamide Caesium carbonate (0.50 g, 1.54 mmol), BINAP (53 mg, 0.08 mmol) and palladium (II)acetate (16 mg, 0.07 mmol) were added under an argon atmosphere and at room temperature to a solution of 4-chloro-2-(3,4-difluorophenyl)-5,7-dihydrothieno[3,4-d]pyrimidine 6,6-dioxide (0.40 g, 1.40 mmol) and 2-(indolin-6-yloxy)-N,N-dimethylacetamide (0.30 g, 1.40 mmol) in dry dioxane (50 mL). The reaction mixture was stirred for 16 h at 100° C., then cooled and filtered through a pad of Celite®. The filtrate was concentrated and purified by flash column chromatography [dichloromethane with 0.5% methanol]. Brownish solid. Yield: 0.48 g (72% of theory)

171b) 2-((1-(2-(3,4-Difluorophenyl)-6-oxido-5,7-dihydrothieno[3,4-d]pyrimidin-4-yl)indolin-6-yl)oxy)-N,N-dimethylacetamide m-Chloroperoxybenzoic acid (77%, 53 mg, 0.24 mmol) in THF (2 mL) was added at 0° C. to a solution of the thioether 171a) (150 mg, 0.32 mmol) in THF (30 mL) and the mixture was stirred for 1 h at room temperature. The reaction mixture was diluted with brine and the aqueous phase was separated and extracted with ethyl acetate (2×10 mL). The combined organic layers were dried over sodium sulfate, the solvents were removed under vacuum, and the remnant was purified by flash column chromatography [dichloromethane with 2% methanol]. Light yellow solid. Yield: 72 mg (46% of theory)

1H NMR (400 MHz, DMSO-d6, δ ppm): 8.27-8.23 (m, 2H), 7.64-7.57 (m, 2H), 7.18 (d, 1H, J=8.1 Hz), 6.59 (dd, 1H, J=2.3 and 8.2 Hz), 4.77 (s, 2H), 4.72 (d, 1H, J=16.4 Hz), 4.55-4.45 (m, 2H), 4.37-4.25 (m, 2H), 4.03 (d, 1H, J=16.8 Hz), 3.17-3.07 (m, 2H), 2.94 (s, 3H), 2.79 (s, 3H).

Compound Nos. 2-18 and 2-141 were prepared analogously:

Compound No. 2-52

2-((1-(2-(4-Methoxyphenyl)-6-oxido-5,7-dihydrothieno[3,4-d]pyrimidin-4-yl)indolin-6-yl)oxy)-N,N-dimethylacetamide (Synthesis Example No. 172)

Light yellow solid. Yield: 110 mg

1H NMR (400 MHz, DMSO-d6, δ ppm): 8.33 (d, 2H, J=8.7 Hz), 7.64 (bs, 1H), 7.16 (d, 1H, J=8.2 Hz), 7.06 (d, 2H, J=8.7 Hz), 6.56 (dd, 1H, J=2.1 and 8.1 Hz), 4.77 (s, 2H), 4.69 (d, 1H, J=16.3 Hz), 4.51-4.43 (m, 2H), 4.35-4.26 (m, 2H), 4.0 (d, 1H, J=16.9 Hz), 3.16-3.07 (m, 2H), 2.93 (s, 3H), 2.80 (s, 3H).

Compound No. 2-141

2-((1-(2-(5-Methoxypyridin-2-yl)-6-oxido-5,7-dihydrothieno[3,4-d]pyrimidin-4-yl)indolin-6-yl)oxy)-N,N-dimethylacetamide (Synthesis Example No. 173)

White solid. Yield: 50 mg
1H NMR (400 MHz, DMSO-d6, δ ppm): 8.46-8.37 (m, 3H), 7.54 (dd, 1H, J=2.9 and 8.8 Hz), 7.14 (d, 1H, J=8.2 Hz), 6.57 (dd, 1H, J=2.3 and 8.1 Hz), 4.86 (s, 2H), 4.78 (d, 1H, J=16.3 Hz), 4.55-4.48 (m, 3H), 4.37-4.33 (m, 1H), 4.03 (d, 1H, J=16.9 Hz), 3.91 (s, 3H), 3.16-3.12 (m, 2H), 2.95 (s, 3H), 2.82 (s, 3H).

SYNTHESIS EXAMPLE NO. 174

2-((1-(2-(3,4-Difluorophenyl)-6,6-dioxido-5,7-dihydrothieno[3,4-d]pyrimidin-4-yl)indolin-6-yl)oxy)-N,N-dimethylacetamide (Compound No. 2-41)

m-Chloroperoxybenzoic acid (77%, 0.15 g, 0.70 mmol) in THF (2 mL) was added at 0° C. to a solution of the thioether 171a) (0.15 g, 0.32 mmol) in THF (30 mL) and the mixture was stirred for 1 h at room temperature. The reaction mixture was quenched with brine and the aqueous phase was separated and extracted with ethyl acetate (2×10 mL). The combined organic layers were dried over sodium sulfate, the solvent was evaporated and the residue purified by flash column chromatography [dichloromethane with 1% methanol]. Light yellow solid. Yield: 0.11 g (68% of theory)
1H NMR (400 MHz, DMSO-d6, δ ppm): 8.23-8.18 (m, 2H), 7.61-7.59 (m, 2H), 7.18 (d, 1H, J=8.1 Hz), 6.61 (dd, 1H, J=2.0 and 8.2 Hz), 4.87 (s, 2H), 4.77 (s, 2H), 4.63 (s, 2H), 4.35 (t, 2H, J=8 Hz), 3.08 (t, 2H, J=8.0 Hz), 2.93 (s, 3H), 2.79 (s, 3H).
Compound No. 2-21 was prepared analogously:

Compound No. 2-21

2-((1-(2-(4-Methoxyphenyl)-6,6-dioxido-5,7-dihydrothieno[3,4-d]pyrimidin-4-yl)indolin-6-yl)oxy)-N,N-dimethylacetamide (Synthesis Example No. 175)

Light yellow solid. Yield: 55 mg
1H NMR (400 MHz, DMSO-d6, δ ppm): 8.29 (d, 2H, J=8.6 Hz), 7.65 (bs, 1H), 7.16 (d, 1H, J=8.3 Hz), 7.06 (d, 2H, J=8.7 Hz), 6.59 (d, 1H, J=6.1 Hz), 4.82 (s, 2H), 4.78 (s, 2H), 4.59 (s, 2H), 4.33 (t, 2H, J=8.3 Hz), 3.83 (s, 3H), 3.08 (t, 2H, J=8 Hz), 2.92 (s, 3H), 2.8 (s, 3H).

Compound No. 2-143

2-((1-(2-(5-Methoxypyridin-2-yl)-6,6-dioxido-5,7-dihydrothieno[3,4-d]pyrimidin-4-yl)indolin-6-yl)oxy)-N,N-dimethylacetamide (Synthesis Example No. 176)

The target compound was synthesized analogously to synthesis example No. 174 with the difference that MMPP was used as oxidation reagent in the last step (see also procedure 63f). Light yellow solid. Yield: 25 mg
1H NMR (400 MHz, DMSO-d6, δ ppm): 8.45-8.33 (m, 3H), 7.55 (d, 1H, J=2.8 Hz), 7.14 (d, 1H, J=8.1 Hz), 6.59 (d, 1H, J=8.1 Hz), 4.94 (s, 2H), 4.86 (s, 2H), 4.62 (s, 2H), 4.39 (t, 2H, J=8.4 Hz), 3.91 (s, 3H), 3.1 (t, 2H, J=8.3 Hz), 2.95 (s, 3H), 2.82 (s, 3H).

cAMP HTRF® Assay to Determine the Activity of hPDE4B1

The inhibiting effect of the compounds on the enzyme activity of human PDE4B1 was measured by the quantification of 5'-adenosine monophosphate (5'-AMP), which is formed from 3',5'-cyclic adenosine monophosphate (cAMP). Human recombinant enzyme, expressed in Sf9 cells, and the HTRF (homogeneous time-resolved fluorescence) detection method were used in the assay.

The test compound or water (control) was mixed with the human recombinant PDE4B1 enzyme (4.8 U) in a buffer consisting of 44.4 mM tris-HCl, 5.28 mM MgCl2, 2.64 mM DTT and 0.044% Tween 20 (pH 7.8). After adding the cAMP enzyme substrate (final concentration 40 nM), the mixture was incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) were added. After 60 minutes the fluorescence transfer, which correlates with the amount of remaining cAMP, was measured with a microplate reader (Rubystar, BMG) at λex=337 nm, λem=620 nm and λem=665 nm. The enzyme activity was calculated from the quotient formed from the measured signal at 665 nm and that at 620 nm. The result was expressed as the percentage inhibition of enzyme activity of the control (without PDE4 inhibitor). The enzyme was omitted for measurement of the basal control.

IC50 values (IC50=concentration causing a half-maximal inhibition of control specific activity) were derived from dose response measurements with eight different concentrations (n=2; N=1-2).

Literature: N. Saldou et al., Comparison of recombinant human PDE4 isoforms: interaction with substrate and inhibitors, Cell. Signal. Vol. 10, No. 6, 427-440, 1998

Several compounds according to the invention are tested with above mentioned assay. The results are given below

TABLE 5

Percentage inhibition of PDE4B at a test substrate concentration of 1 μmM):

| Compound No. | Inhibition at 1 μM test concentration [%] |
| --- | --- |
| 1-1 | 102 |
| 1-2 | 91 |
| 1-3 | 83 |
| 1-5 | 98 |
| 1-8 | 102 |
| 1-10 | 96 |
| 1-11 | 100 |
| 1-12 | 108 |
| 1-13 | 78 |
| 1-15 | 100 |
| 1-16 | 95 |
| 1-17 | 83 |
| 1-18 | 92 |
| 1-19 | 85 |
| 1-20 | 92 |
| 1-21 | 88 |
| 1-22 | 115 |
| 1-23 | 93 |
| 1-24 | 111 |
| 1-25 | 103 |
| 1-39 | 63 |
| 1-50 | 76 |
| 1-59 | 38 |
| 1-60 | 67 |
| 1-61 | 82 |
| 1-63 | 35 |
| 1-64 | 28 |
| 1-65 | 34 |

TABLE 5-continued

Percentage inhibition of PDE4B at a test substrate concentration of 1 μmM):

| Compound No. | Inhibition at 1 μM test concentration [%] |
|---|---|
| 1-66 | 61 |
| 1-68 | 34 |
| 1-69 | 61 |
| 1-70 | 61 |
| 1-71 | 64 |
| 1-72 | 59 |
| 1-73 | 80 |
| 1-74 | 31 |
| 1-75 | 101 |
| 1-77 | 62 |
| 1-78 | 25 |
| 1-79 | 88 |
| 1-80 | 108 |
| 1-81 | 106 |
| 2-18 | 105 |
| 2-20 | 98 |
| 2-21 | 88 |
| 2-24 | 115 |
| 2-33 | 100 |
| 2-34 | 73 |
| 2-36 | 98 |
| 2-37 | 96 |
| 2-40 | 119 |
| 2-41 | 85 |
| 2-42 | 79 |
| 2-45 | 105 |
| 2-46 | 94 |
| 2-48 | 94 |
| 2-49 | 127 |
| 2-54 | 54 |
| 2-55 | 52 |
| 2-56 | 68 |
| 2-57 | 89 |
| 2-58 | 70 |
| 2-59 | 76 |
| 2-60 | 75 |
| 2-61 | 60 |
| 2-62 | 91 |
| 3-8 | 32 |
| 2-64 | 65 |
| 2-65 | 5 |
| 2-66 | 32 |
| 2-67 | 6 |
| 2-68 | 2 |
| 2-69 | 4 |
| 2-70 | 23 |
| 2-71 | 14 |
| 2-72 | 102 |
| 2-73 | 116 |
| 2-74 | 80 |
| 2-75 | 39 |
| 2-76 | 62 |
| 2-77 | 92 |
| 2-78 | 105 |
| 2-79 | 92 |
| 2-80 | (101% inh. at 0.1 μM) |
| 2-81 | (113% inh. at 0.1 μM) |
| 2-82 | 99 |
| 2-83 | 97 |
| 2-84 | 91 |
| 2-85 | 99 |
| 2-86 | 111 |
| 2-87 | 112 |
| 2-88 | 73 |
| 2-89 | 119 |
| 2-90 | 117 |
| 2-91 | 117 |
| 2-92 | 97 |
| 2-93 | 121 |
| 2-94 | 91 |
| 2-95 | 113 |
| 2-96 | 107 |
| 2-97 | 93 |
| 2-98 | 98 |
| 2-99 | 104 |
| 2-100 | 100 |
| 2-101 | 120 |
| 2-102 | 110 |
| 2-103 | 91 |
| 2-104 | 85 |
| 2-105 | 77 |
| 2-106 | 104 |
| 2-107 | 113 |
| 2-108 | 62 |
| 2-109 | 98 |
| 2-110 | 119 |
| 2-111 | 72 |
| 2-112 | 64 |
| 2-113 | 99 |
| 2-114 | 38 |
| 2-115 | 106 |
| 2-116 | 121 |
| 2-117 | 88 |
| 2-118 | 93 |
| 2-119 | 107 |
| 2-120 | 116 |
| 2-121 | 111 |
| 2-122 | 40 |
| 2-123 | 95 |
| 2-124 | 104 |
| 2-125 | 85 |
| 2-126 | 104 |
| 2-127 | 43 |
| 2-128 | 85 |
| 2-129 | 48 |
| 2-130 | 87 |
| 2-131 | 90 |
| 2-132 | 91 |
| 2-133 | 94 |
| 2-134 | 77 |
| 2-135 | 97 |
| 2-136 | 98 |
| 2-137 | 97 |
| 2-138 | 102 |
| 2-138 | 101 |
| 2-140 | 95 |
| 2-141 | 98 |
| 2-142 | 61 |
| 2-143 | 87 |
| 2-144 | 92 |
| 2-145 | 95 |
| 2-146 | 104 |
| 2-147 | 86 |
| 2-148 | 100 |
| 2-149 | 92 |
| 2-150 | 126 |
| 2-151 | 108 |
| 2-152 | 88 |
| 2-153 | 97 |
| 2-154 | 104 |
| 2-155 | 102 |
| 3-6 | 103 |
| 3-7 | 48 |

The following compounds according to the invention showed an 1050 value in the following ranges:

IC50 in the range from 0.1 until 1 μM: Compound Nos. 1-17, 1-39, 1-50, 1-60, 1-61, 1-66, 1-69, 1-70, 1-71, 1-72, 1-73, 1-77, 1-79, 2-34, 2-54, 2-56, 2-58, 2-59, 2-60, 2-64, 2-74, 2-76, 2-86, 2-88, 2-94, 2-97, 2-103, 2-104, 2-105, 2-111, 2-112, 2-128, 2-142, 2-143, 2-144, 3-1, 3-3, 3-4, and 3-5.

IC50 below 0.1 μM: Compound Nos. 1-1, 1-2, 1-3, 1-5, 1-8, 1-10, 1-11, 1-12, 1-13, 1-15, 1-16, 1-18, 1-19, 2-18, 1-20, 1-21, 1-22, 1-23, 1-24, 1-25, 1-75, 1-80, 1-81, 2-18, 2-20, 2-21, 2-24, 2-31, 2-33, 2-36, 2-37, 2-40, 2-41, 2-42, 2-45, 2-46, 2-48, 2-49, 2-57, 2-61, 2-62, 2-72, 2-73, 2-77, 2-78, 2-79, 2-80, 2-81, 2-82, 2-83, 2-84, 2-85, 2-87, 2-89, 2-90, 2-91, 2-92, 2-93, 2-95, 2-96, 2-98, 2-99, 2-100, 2-101, 2-102, 2-106, 2-107, 2-109, 2-110, 2-113, 2-115, 2-116 to 2-121, 2-123, 2-124, 2-125, 2-126, 2-130, 2-131, 2-132, 2-133, 2-134, 2-135, 2-136, 2-137, 2-138, 2-139, 2-140, 2-141, 2-143, 2-145, 2-146, 2-147, 2-148, 2-149, 2-150, 2-151, 2-152, 2-153, 2-154, 2-155, and 3-6.
The invention claimed is:
1. A pyrimidine compound of formula (I):
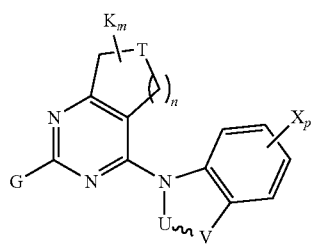
(I)
in which
G is selected from the following groups G1 to G47:
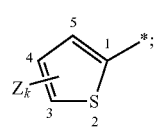
G1
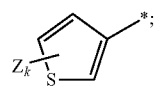
G2
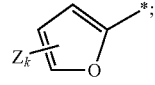
G3
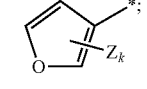
G4
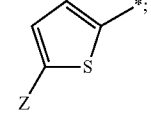
G5
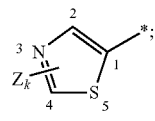
G6
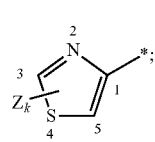
G7
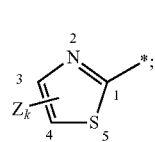
G8
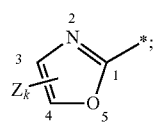
G9
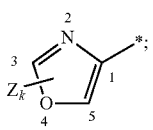
G10
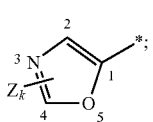
G11
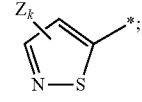
G12
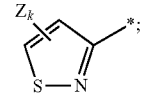
G13
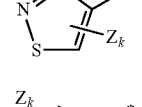
G14
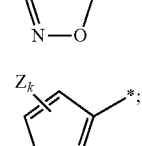
G15
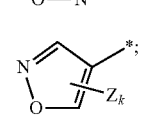
G16
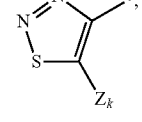
G17
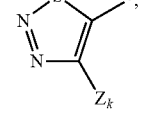
G18
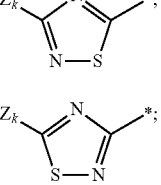
G19
G20
G21

-continued
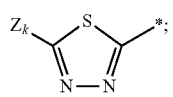 G22
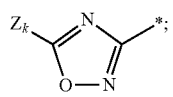 G23
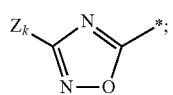 G24
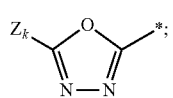 G25
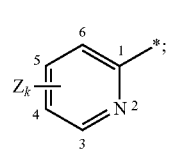 G26
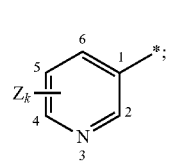 G27
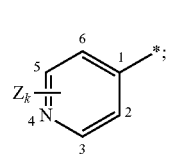 G28
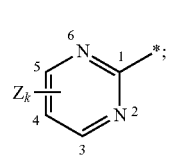 G29
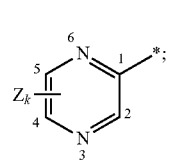 G30
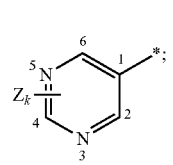 G31
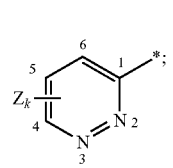 G32
-continued
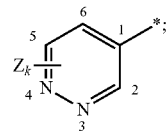 G33
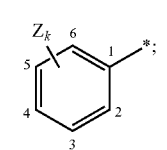 G34
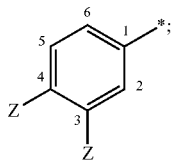 G35
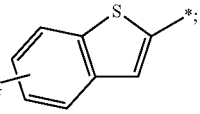 G36
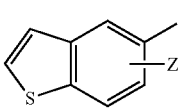 G37
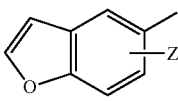 G38
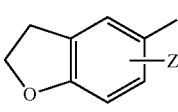 G39
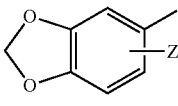 G40
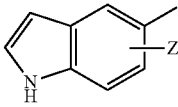 G41
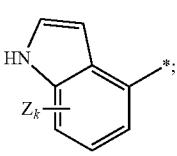 G42
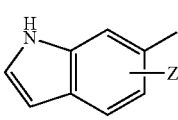 G43
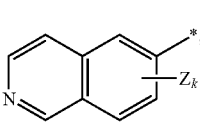 G44

-continued

G45

G46

G47 in which the site marked with an asterisk (*) indicates the binding site at position 2 of the pyrimidine ring;

Z independently of one another is $(C_1\text{-}C_6)$ alkyl, $(C_1\text{-}C_6)$ hydroxyalkyl, $(C_1\text{-}C_6)$ alkoxy, $(C_1\text{-}C_6)$ haloalkyl, $(C_1\text{-}C_6)$ haloalkoxy, —S$(C_1\text{-}C_6)$ alkyl, halogen, hydroxyl or cyano or is $SO_2(C_1\text{-}C_6)$alkyl, $CONH_2$,$NHSO_2(C_1\text{-}C_6)$ alkyl, $NHCO(C_1\text{-}C_6)$alkyl wherein the aforementioned alkyls are branched or straight-chain and is optionally substituted;

T is $CR^1R^2$ or $S(O)_X$ or $S(O)=NH$;

x is 0, 1 or 2;

$R^1$ and $R^2$ independently of one another are hydrogen, $(C_1\text{-}C_6)$ alkyl, $(C_1\text{-}C_6)$ alkoxy, $(C_1\text{-}C_6)$ haloalkyl, halogen, hydroxyl or cyano, wherein the aforementioned alkyl chains are branched or straight-chain and is optionally substituted;

n is 1 or 2;

K is $(C_1\text{-}C_6)$ alkyl, $(C_1\text{-}C_6)$ alkoxy, $(C_1\text{-}C_6)$ haloalkyl, halogen, hydroxyl or cyano, wherein the aforementioned alkyl chains are branched or straight-chain and is optionally substituted;

m is 0, 1, 2, 3 or 4;

X independently of one another is $(C_1\text{-}C_6)$ alkyl, $(C_3\text{-}C_6)$ cycloalkyl, $(C_1\text{-}C_6)$ alkoxy, $(C_3\text{-}C_6)$ cycloalkoxy, $(C_1\text{-}C_6)$ haloalkyl, $(C_1\text{-}C_6)$ haloalkoxy, halogen, hydroxyl, cyano, carboxyl, $C(O)$—$NH_2$, $C(O)$—$NH(C_1\text{-}C_6)$alkyl, $C(O)$—$N((C_1\text{-}C_6)$ alkyl$)_2$, $NH_2$, $NH(C_1\text{-}C_6)$alkyl, $N((C_1\text{-}C_6)$ alkyl$)_2$, N-pyrrolidinyl, N-piperidinyl, N-morpholinyl, NH—CHO, NH—$C(O)$—$(C_1\text{-}C_6)$ alkyl, $S(O)_2$—$NH_2$, $S(C_1\text{-}C_6)$alkyl, $S(O)$—$(C_1\text{-}C_6)$ alkyl, $S(O)_2$—$(C_1\text{-}C_6)$alkyl, O—$(C_1\text{-}C_4)$alkyl-CN, O—$(C_1\text{-}C_4)$alkyl-NH—CHO, O—$(C_1\text{-}C_4)$alkyl-NH—$C(O)$—$(C_1\text{-}C_6)$alkyl, or O—$(C_1\text{-}C_4)$ alkyl-N$((C_1\text{-}C_6)$ alkyl$)_2$, or is O—$(C_1\text{-}C_4)$alkyl-O—$(C_1\text{-}C_4)$alkyl, wherein the aforementioned alkyl chains are branched or straight-chain and is optionally substituted, or is a chemical grouping L—$CO_2R^3$ or O—$(C_1\text{-}C_4)$alkyl-CO—$R^4$ or $LCONR^4$ ;

$R^3$ is hydrogen, branched or straight-chain $(C_1\text{-}C_6)$alkyl;

$R^4$ is $NH_2$, $NHR^5$, $NR^5R^6$, $(C_1\text{-}C_6)$ alkoxy;

$R^5$ and $R^6$ independently of one another is $(C_1\text{-}C_6)$ alkyl, $(C_1\text{-}C_6)$ hydroxyalkyl, $(C_3\text{-}C_6)$ cycloalkyl, $(C_1\text{-}C_6)$ alkyl$(C_3\text{-}C_6)$cycloalkyl, $(C_3\text{-}C_6)$ heterocycloalkyl, or $R^5$ and $R^6$, together with the nitrogen atom to which they are bound form a saturated 3- to 6-membered heterocycle, optionally substituted with branched or straight-chain $(C_1\text{-}C_6)$ alkyl or hydroxyl groups, which heterocycle can optionally have at least one further heteroatom selected from O, S, and N;

L is a bond, $(C_1\text{-}C_6)$ alkylene, $(C_2\text{-}C_6)$ alkenylene, —O—$(C_1\text{-}C_4)$ alkylene, —NH—$(C_1\text{-}C_4)$ alkylene, or -$NR^3$—$(C_1\text{-}C_4)$ alkylene, wherein aforementioned alkylenes or alkenylenes can each be substituted with one or more halogen atoms or wherein aforementioned alkylenes or alkenylenes is optionally substituted with one or more $(C_1\text{-}C_6)$ alkyl groups, or wherein in aforementioned alkylenes or alkenylenes a $CH_2$ unit is optionally replaced by an oxygen atom;

p is 1, 2, 3 or 4;

U~V is selected from $CR^7R^8$—$CR^7R^8$; $CR^7=CR^7$, $N=CR^7$, $CR^7=N$, $N=N$, $C(=O)$—$CR^7R^8$, and $C(=O)$—O; and $R^7$ and $R^8$ independently of one another are hydrogen, $(C_1\text{-}C_4)$ alkyl, $(C_1\text{-}C_4)$ alkoxy, CHF, $CH_2F$ or $CF_3$, $(C_1\text{-}C_4)$ hydroxyalkyl, F, Cl, Br, hydroxyl or cyano;

or a pharmacologically tolerable salt, diastereomer, enantiomer, racemate, hydrate or solvate thereof.

2. The pyrimidine compound according to claim 1, wherein

X is O—$(C_1\text{-}C_4)$alkyl-CN, O—$(C_1\text{-}C_4)$alkyl-NH—$C(O)$—$(C_1\text{-}C_6)$alkyl, O—$(C_1\text{-}C_4)$alkyl-O—$(C_1\text{-}C_4)$ alkyl, L—$CO_2R^3$, O—$(C_1\text{-}C_4)$ alkyl-CO—$R^4$, or $LCONR^4$;

$R^3$ is hydrogen, branched or straight-chain $(C_1\text{-}C_4)$ alkyl;

$R^4$ is $NH_2$, $NHCH_3$, $N(CH_3)_2$, $NHC_2H_5$, $NHCH(CH_3)_2$, $NHCH_2CH_2OH$, $OCH_3$ or one of the following groups:

L is a bond or methylene, wherein the methylene is optionally substituted with one or two halogen atoms.

3. The pyrimidine compound according to claim 1, wherein

T is $CH_2$, S, SO, $SO_2$, or SONH.

4. The pyrimidine compound according to claim 1, wherein

U~V is selected from $CH_2$-$CH_2$, CH=CH, N=CH, CH=N, N=N, $C(=O)$—$CH_2$, and $C(=O)$—O.

5. The pyrimidine compound according to claim 1, wherein

X is O—$(C_1\text{-}C_4)$alkyl-CN, O—$(C_1\text{-}C_4)$alkyl-NH—$C(O)$—$(C_1\text{-}C_6)$alkyl, O—$(C_1\text{-}C_4)$alkyl- O—$(C_1\text{-}C_4)$ alkyl, L—$CO_2R^3$, O—$(C_1\text{-}C_4)$ alkyl-CO—$R^4$, or $LCONR^4$;

$R^3$ is hydrogen, branched or straight-chain $(C_1\text{-}C_4)$ alkyl;

$R^4$ is $NH_2$, $NHR^5$, $NR^5R^6$, $(C_1\text{-}C_6)$ alkoxy;

$R^5$ and $R^6$ independently of one another is $(C_1\text{-}C_6)$ alkyl, $(C_1\text{-}C_6)$ hydroxyalkyl, $(C_3\text{-}C_6)$ cycloalkyl, $(C_1\text{-}C_6)$ alkyl$(C_3\text{-}C_6)$cycloalkyl, $(C_3\text{-}C_6)$ heterocycloalkyl, or $R^5$ and $R^6$, together with the nitrogen atom to which they are bound form a saturated 3—to 6-membered heterocycle, optionally substituted with branched or straight-chain ($C_1$-$C_6$) alkyl or hydroxyl groups, which heterocycle can optionally have at least one further heteroatom selected from O, S, and N;

L is a bond or methylene, wherein the methylene is optionally substituted with one or two halogen atoms.

6. The pyrimidine compound according to claim 1, wherein n is 1.

7. The pyrimidine compound according to claim 1, wherein n is 2.

8. The pyrimidine compound according to claim 1, wherein if G is any one of G1 -G8, G26-G29 or G36-G47 then k is 0 or 1 and if G is phenyl, then k is 1 or 2.

9. The pyrimidine compound according to claim 1, wherein p is 1 or 2.

10. A pharmaceutical composition comprising at least one compound as defined in claim 1.

\* \* \* \* \*

UNITED STATES PATENT AND TRADEMARK OFFICE
CERTIFICATE OF CORRECTION

PATENT NO. : 9,527,832 B2
APPLICATION NO. : 14/883986
DATED : December 27, 2016
INVENTOR(S) : Ingo Konetzki et al.

Page 1 of 1

It is certified that error appears in the above-identified patent and that said Letters Patent is hereby corrected as shown below:

In the Specification

Column 15, Line 34, "carbocylces" -- should read -- carbocycles --.

Column 73, Line 62, "theory) 61b) Ethyl" -- should read -- theory) ¶ 61b) --.

Column 82, Line 16, "HOBT.NH3" -- should read -- HOBT NH3 --.

Column 83, Line 25, "theory) 1H" -- should read -- theory) ¶ 1H --.

Column 102, Line 54, "1050 value" -- should read -- 1C50 value --.

In the Claims

Column 107, Line 7, "G46" -- should read -- G46; or --.

Signed and Sealed this
Second Day of July, 2019

Andrei Iancu
*Director of the United States Patent and Trademark Office*